(12) United States Patent
Smith et al.

(10) Patent No.: US 11,545,263 B2
(45) Date of Patent: *Jan. 3, 2023

(54) MULTIPLE WAVELENGTH SENSOR EMITTERS

(71) Applicant: Cercacor Laboratories, Inc., Irvine, CA (US)

(72) Inventors: Robert A. Smith, Lake Forest, CA (US); David Dalke, Rancho Santa Margarita, CA (US); Ammar Al-Ali, San Juan Capistrano, CA (US); Mohamed K. Diab, Ladera Ranch, CA (US); Marcelo M. Lamego, Cupertino, CA (US)

(73) Assignee: Cercacor Laboratories, Inc., Irvine, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/224,833

(22) Filed: Apr. 7, 2021

(65) Prior Publication Data

US 2021/0241903 A1 Aug. 5, 2021

Related U.S. Application Data

(63) Continuation of application No. 16/437,611, filed on Jun. 11, 2019, which is a continuation of application
(Continued)

(51) Int. Cl.
*A61B 5/1455* (2006.01)
*G16H 40/67* (2018.01)
(Continued)

(52) U.S. Cl.
CPC .......... *G16H 40/67* (2018.01); *A61B 5/0022* (2013.01); *A61B 5/0205* (2013.01);
(Continued)

(58) Field of Classification Search
CPC .............. A61B 5/1455; A61B 5/14551; A61B 5/14552; A61B 5/14553; A61B 5/14546;
(Continued)

(56) References Cited

U.S. PATENT DOCUMENTS 3,316,395 A 4/1967 Lavin
3,316,396 A 4/1967 Lavin
(Continued)

FOREIGN PATENT DOCUMENTS

DE 3244695 C2 10/1985
EP 0102816 3/1984
(Continued)

OTHER PUBLICATIONS

US 8,845,543 B2, 09/2014, Diab et al. (withdrawn)
(Continued)

*Primary Examiner* — Chu Chuan Liu
(74) *Attorney, Agent, or Firm* — Knobbe, Martens, Olson & Bear, LLP

(57) ABSTRACT

A physiological sensor has light emitting sources, each activated by addressing at least one row and at least one column of an electrical grid. The light emitting sources are capable of transmitting light of multiple wavelengths and a detector is responsive to the transmitted light after attenuation by body tissue.

30 Claims, 48 Drawing Sheets

Related U.S. Application Data

No. 15/694,541, filed on Sep. 1, 2017, now Pat. No. 10,327,683, which is a continuation of application No. 14/472,760, filed on Aug. 29, 2014, now Pat. No. 9,750,443, which is a continuation of application No. 13/776,065, filed on Feb. 25, 2013, now Pat. No. 8,849,365, which is a continuation of application No. 12/422,915, filed on Apr. 13, 2009, now Pat. No. 8,385,996, which is a continuation of application No. 11/367,013, filed on Mar. 1, 2006, now Pat. No. 7,764,982.

(60) Provisional application No. 60/657,759, filed on Mar. 1, 2005, provisional application No. 60/657,268, filed on Mar. 1, 2005, provisional application No. 60/657,596, filed on Mar. 1, 2005, provisional application No. 60/657,281, filed on Mar. 1, 2005.

(51) Int. Cl.
*G16H 10/40* (2018.01)
*A61B 5/0205* (2006.01)
*A61B 5/145* (2006.01)
*A61B 5/00* (2006.01)
*A61B 5/026* (2006.01)
*A61B 5/0295* (2006.01)
*A61B 5/024* (2006.01)
*A61B 5/1495* (2006.01)
*A61B 1/00* (2006.01)

(52) U.S. Cl.
CPC .......... *A61B 5/0261* (2013.01); *A61B 5/0295* (2013.01); *A61B 5/02416* (2013.01); *A61B 5/1455* (2013.01); *A61B 5/1495* (2013.01); *A61B 5/14532* (2013.01); *A61B 5/14546* (2013.01); *A61B 5/14551* (2013.01); *A61B 5/14552* (2013.01); *A61B 5/6815* (2013.01); *A61B 5/6826* (2013.01); *A61B 5/6829* (2013.01); *A61B 5/6832* (2013.01); *A61B 5/6838* (2013.01); *A61B 5/7221* (2013.01); *A61B 5/7246* (2013.01); *A61B 5/7275* (2013.01); *A61B 5/7278* (2013.01); *A61B 5/742* (2013.01); *A61B 5/7405* (2013.01); *A61B 5/746* (2013.01); *A61B 5/7475* (2013.01); *G16H 10/40* (2018.01); *H05K 999/99* (2013.01); *A61B 1/00* (2013.01); *A61B 5/02427* (2013.01); *A61B 2562/08* (2013.01); *A61B 2562/085* (2013.01); *A61B 2562/185* (2013.01); *A61B 2562/222* (2013.01); *Y10S 439/909* (2013.01)

(58) Field of Classification Search
CPC ... A61B 5/6832; A61B 5/6826; A61B 5/1495; A61B 5/6838; A61B 5/14532; A61B 5/0205; A61B 5/02416
See application file for complete search history.

(56) References Cited

U.S. PATENT DOCUMENTS

| | | |
|---|---|---|
| 3,452,215 A | 6/1969 | Alessio |
| 3,740,570 A | 6/1973 | Kaelin |
| 3,760,582 A | 9/1973 | Thiess et al. |
| 3,789,601 A | 2/1974 | Bergey |
| 3,910,701 A | 10/1975 | Henderson et al. |
| 3,998,550 A | 12/1976 | Konishi et al. |
| 4,014,321 A | 3/1977 | March |
| 4,015,595 A | 4/1977 | Benjamin |
| 4,051,522 A | 9/1977 | Healy et al. |
| 4,134,678 A | 1/1979 | Brown et al. |
| 4,157,708 A | 6/1979 | Imura |
| 4,163,290 A | 7/1979 | Sutherlin et al. |
| 4,167,331 A | 9/1979 | Nielsen |
| 4,224,948 A | 9/1980 | Cramer et al. |
| 4,266,554 A | 5/1981 | Hamaguri |
| 4,267,844 A | 5/1981 | Yamanishi |
| 4,295,475 A | 10/1981 | Torzala |
| 4,305,059 A | 12/1981 | Benton |
| 4,331,161 A | 5/1982 | Patel |
| 4,399,824 A | 8/1983 | Davidson |
| 4,409,470 A | 10/1983 | Shepard et al. |
| 4,446,871 A | 5/1984 | Imura |
| 4,447,150 A | 5/1984 | Heinemann |
| 4,491,725 A | 1/1985 | Pritchard |
| 4,531,527 A | 7/1985 | Reinhold, Jr. et al. |
| 4,547,075 A | 10/1985 | Fei |
| 4,561,440 A | 12/1985 | Kubo et al. |
| 4,586,513 A | 5/1986 | Hamaguri |
| 4,603,700 A | 8/1986 | Nichols et al. |
| 4,621,643 A | 11/1986 | New et al. |
| 4,653,498 A | 3/1987 | New, Jr. et al. |
| 4,655,225 A | 4/1987 | Dahne et al. |
| 4,685,464 A | 8/1987 | Goldberger et al. |
| 4,694,833 A | 9/1987 | Hamaguri |
| 4,695,955 A | 9/1987 | Faisandier |
| 4,700,708 A | 10/1987 | New et al. |
| 4,714,341 A | 12/1987 | Hamaguri et al. |
| 4,759,369 A | 7/1988 | Taylor |
| 4,770,179 A | 9/1988 | New et al. |
| 4,773,422 A | 9/1988 | Isaacson et al. |
| 4,781,195 A | 11/1988 | Martin |
| 4,800,885 A | 1/1989 | Johnson |
| 4,802,486 A | 2/1989 | Goodman et al. |
| 4,805,623 A | 2/1989 | Jobsis |
| 4,822,997 A | 4/1989 | Fuller et al. |
| 4,832,484 A | 5/1989 | Aoyagi et al. |
| 4,846,183 A | 7/1989 | Martin |
| 4,854,328 A | 8/1989 | Pollack |
| 4,859,057 A | 8/1989 | Taylor et al. |
| 4,863,265 A | 9/1989 | Flower et al. |
| 4,865,038 A | 9/1989 | Rich et al. |
| 4,867,557 A | 9/1989 | Takatani et al. |
| 4,867,571 A | 9/1989 | Frick et al. |
| 4,868,476 A | 9/1989 | Respaut |
| 4,869,253 A | 9/1989 | Craig, Jr. et al. |
| 4,869,254 A | 9/1989 | Stone et al. |
| 4,890,306 A | 12/1989 | Noda |
| 4,903,701 A | 2/1990 | Moore et al. |
| 4,907,876 A | 3/1990 | Suzuki et al. |
| 4,911,167 A | 3/1990 | Corenman et al. |
| 4,928,692 A | 5/1990 | Goodman et al. |
| 4,933,545 A | 6/1990 | Saaski et al. |
| 4,934,372 A | 6/1990 | Corenman et al. |
| 4,938,218 A | 7/1990 | Goodman et al. |
| 4,941,236 A | 7/1990 | Sherman et al. |
| 4,942,877 A | 7/1990 | Sakai et al. |
| 4,945,239 A | 7/1990 | Wist et al. |
| 4,955,379 A | 9/1990 | Hall |
| 4,960,126 A | 10/1990 | Conlon et al. |
| 4,960,128 A | 10/1990 | Gordon et al. |
| 4,960,314 A | 10/1990 | Smith et al. |
| 4,964,010 A | 10/1990 | Miyasaka et al. |
| 4,964,408 A | 10/1990 | Hink et al. |
| 4,967,571 A | 11/1990 | Sporri |
| 4,975,581 A | 12/1990 | Robinson et al. |
| 4,975,647 A | 12/1990 | Downer et al. |
| 4,986,665 A | 1/1991 | Yamanishi et al. |
| 4,996,975 A | 3/1991 | Nakamura |
| 4,997,769 A | 3/1991 | Lundsgaard |
| 5,003,979 A | 4/1991 | Merickel et al. |
| 5,007,423 A | 4/1991 | Branstetter et al. |
| 5,025,791 A | 6/1991 | Niwa |
| RE33,643 E | 7/1991 | Isaacson et al. |
| 5,028,787 A | 7/1991 | Rosenthal et al. |
| 5,033,472 A | 7/1991 | Sato et al. |
| 5,041,187 A | 8/1991 | Hink et al. |
| 5,054,495 A | 10/1991 | Uemura et al. |
| 5,058,588 A | 10/1991 | Kaestle et al. |

(56) References Cited

U.S. PATENT DOCUMENTS

| | | |
|---|---|---|
| 5,069,213 A | 12/1991 | Hink et al. |
| 5,069,680 A | 12/1991 | Grandjean |
| 5,077,476 A | 12/1991 | Rosenthal |
| 5,078,136 A | 1/1992 | Stone et al. |
| 5,101,825 A | 4/1992 | Gravensetin et al. |
| 5,137,023 A | 8/1992 | Mendelson et al. |
| 5,155,697 A | 10/1992 | Bunsen |
| 5,158,082 A | 10/1992 | Jones |
| 5,162,725 A | 11/1992 | Hodson et al. |
| 5,163,438 A | 11/1992 | Gordon et al. |
| 5,176,137 A | 1/1993 | Erickson et al. |
| 5,188,108 A | 2/1993 | Secker |
| 5,189,609 A | 2/1993 | Tivig et al. |
| 5,190,038 A | 3/1993 | Polson et al. |
| 5,190,040 A | 3/1993 | Aoyagi |
| 5,203,329 A | 4/1993 | Takatani et al. |
| 5,209,230 A | 5/1993 | Swedlow et al. |
| 5,218,962 A | 6/1993 | Mannheimer et al. |
| 5,226,053 A | 7/1993 | Cho et al. |
| 5,226,417 A | 7/1993 | Swedlow et al. |
| 5,246,002 A | 9/1993 | Prosser |
| 5,247,931 A | 9/1993 | Norwood |
| 5,251,011 A | 10/1993 | Fujiwara et al. |
| 5,254,388 A | 10/1993 | Melby et al. |
| 5,254,992 A | 10/1993 | Keen et al. |
| 5,259,381 A | 11/1993 | Chung |
| 5,267,562 A | 12/1993 | Ukawa et al. |
| 5,267,563 A | 12/1993 | Swedlow et al. |
| 5,278,627 A | 1/1994 | Aoyagi |
| 5,297,548 A | 3/1994 | Pologe |
| 5,313,940 A | 5/1994 | Fuse et al. |
| 5,319,355 A | 6/1994 | Russek |
| 5,331,549 A | 7/1994 | Crawford, Jr. |
| 5,335,659 A | 8/1994 | Pologe et al. |
| 5,337,744 A | 8/1994 | Branigan |
| 5,337,745 A | 8/1994 | Benaron |
| 5,341,805 A | 8/1994 | Stavridi et al. |
| 5,348,004 A | 9/1994 | Hollub |
| 5,351,685 A | 10/1994 | Potratz |
| 5,355,129 A | 10/1994 | Baumann |
| 5,355,242 A | 10/1994 | Eastmond et al. |
| 5,355,880 A | 10/1994 | Thomas et al. |
| 5,355,882 A | 10/1994 | Ukawa et al. |
| 5,361,758 A | 11/1994 | Hall et al. |
| 5,368,041 A | 11/1994 | Shambroom |
| 5,368,224 A | 11/1994 | Richardson et al. |
| D353,195 S | 12/1994 | Savage et al. |
| D353,196 S | 12/1994 | Savage et al. |
| 5,370,114 A | 12/1994 | Wong et al. |
| 5,372,135 A | 12/1994 | Mendelson et al. |
| 5,372,136 A | 12/1994 | Steuer et al. |
| 5,377,676 A | 1/1995 | Vari et al. |
| 5,383,874 A | 1/1995 | Jackson et al. |
| 5,385,143 A | 1/1995 | Aoyagi |
| 5,387,122 A | 2/1995 | Goldberger et al. |
| 5,392,777 A | 2/1995 | Swedlow et al. |
| 5,400,267 A | 3/1995 | Denen et al. |
| 5,413,101 A | 5/1995 | Sugiura |
| D359,546 S | 6/1995 | Savage et al. |
| 5,421,329 A | 6/1995 | Casciani et al. |
| 5,424,545 A | 6/1995 | Block et al. |
| 5,425,362 A | 6/1995 | Siker et al. |
| 5,425,375 A | 6/1995 | Chin et al. |
| 5,427,093 A | 6/1995 | Ogawa et al. |
| 5,429,128 A | 7/1995 | Cadell et al. |
| 5,431,170 A | 7/1995 | Mathews |
| 5,435,309 A | 7/1995 | Thomas et al. |
| 5,436,499 A | 7/1995 | Namavar et al. |
| D361,840 S | 8/1995 | Savage et al. |
| D362,063 S | 9/1995 | Savage et al. |
| 5,452,717 A | 9/1995 | Branigan et al. |
| D363,120 S | 10/1995 | Savage et al. |
| 5,456,252 A | 10/1995 | Vari et al. |
| 5,469,845 A | 11/1995 | DeLonzor et al. |
| RE35,122 E | 12/1995 | Corenman et al. |
| 5,479,934 A | 1/1996 | Imran |
| 5,482,036 A | 1/1996 | Diab et al. |
| 5,487,386 A | 1/1996 | Wakabayashi et al. |
| 5,490,505 A | 2/1996 | Diab et al. |
| 5,490,523 A | 2/1996 | Isaacson et al. |
| 5,494,032 A | 2/1996 | Robinson et al. |
| 5,494,043 A | 2/1996 | O'Sullivan et al. |
| 5,503,148 A | 4/1996 | Pologe et al. |
| 5,520,177 A | 5/1996 | Ogawa |
| 5,528,519 A | 6/1996 | Ohkura et al. |
| 5,533,507 A | 7/1996 | Potratz |
| 5,533,511 A | 7/1996 | Kaspari et al. |
| 5,534,851 A | 7/1996 | Russek |
| 5,542,146 A | 8/1996 | Hoekstra et al. |
| 5,551,423 A | 9/1996 | Sugiura |
| 5,553,615 A | 9/1996 | Carim et al. |
| 5,555,882 A | 9/1996 | Richardson et al. |
| 5,561,275 A | 10/1996 | Savage et al. |
| 5,562,002 A | 10/1996 | Lalin |
| 5,575,284 A | 11/1996 | Athan et al. |
| 5,577,500 A | 11/1996 | Potratz |
| 5,581,069 A | 12/1996 | Shepard et al. |
| 5,584,296 A | 12/1996 | Cui et al. |
| 5,584,299 A | 12/1996 | Sakai et al. |
| 5,588,427 A | 12/1996 | Tien |
| 5,590,649 A | 1/1997 | Caro et al. |
| 5,590,652 A | 1/1997 | Inai |
| 5,595,176 A | 1/1997 | Yamaura |
| 5,596,992 A | 1/1997 | Haaland et al. |
| 5,602,924 A | 2/1997 | Durand et al. |
| 5,603,323 A | 2/1997 | Pflugrath et al. |
| 5,603,623 A | 2/1997 | Nishikawa et al. |
| 5,615,672 A | 4/1997 | Braig et al. |
| 5,617,857 A | 4/1997 | Chader et al. |
| 5,630,413 A | 5/1997 | Thomas et al. |
| 5,632,272 A | 5/1997 | Diab et al. |
| 5,635,700 A | 6/1997 | Fazekas |
| 5,638,816 A | 6/1997 | Kiani-Azarbayjany et al. |
| 5,638,818 A | 6/1997 | Diab et al. |
| 5,645,059 A | 7/1997 | Fein et al. |
| 5,645,060 A | 7/1997 | Yorkey |
| 5,645,440 A | 7/1997 | Tobler et al. |
| 5,651,780 A | 7/1997 | Jackson et al. |
| 5,658,248 A | 8/1997 | Klein et al. |
| 5,660,567 A | 8/1997 | Nierlich et al. |
| 5,662,106 A | 9/1997 | Swedlow et al. |
| 5,671,914 A | 9/1997 | Kalkhoran et al. |
| 5,676,139 A | 10/1997 | Goldberger et al. |
| 5,676,141 A | 10/1997 | Hollub |
| 5,678,544 A | 10/1997 | Delonzor et al. |
| 5,685,299 A | 11/1997 | Diab et al. |
| 5,685,301 A | 11/1997 | Klomhaus |
| 5,687,719 A | 11/1997 | Sato et al. |
| 5,687,722 A | 11/1997 | Tien et al. |
| 5,690,104 A | 11/1997 | Kanemoto et al. |
| 5,692,503 A | 12/1997 | Kuenstner |
| 5,697,371 A | 12/1997 | Aoyagi |
| 5,702,429 A | 12/1997 | King |
| 5,713,355 A | 2/1998 | Richardson et al. |
| 5,719,557 A | 2/1998 | Rattman et al. |
| 5,719,589 A | 2/1998 | Norman et al. |
| 5,720,284 A | 2/1998 | Aoyagi et al. |
| 5,720,293 A | 2/1998 | Quinn et al. |
| 5,726,440 A | 3/1998 | Kalkhoran et al. |
| 5,730,125 A | 3/1998 | Prutchi et al. |
| D393,830 S | 4/1998 | Tobler et al. |
| 5,742,718 A | 4/1998 | Harman et al. |
| 5,743,262 A | 4/1998 | Lepper, Jr. et al. |
| 5,743,263 A | 4/1998 | Baker, Jr. |
| 5,746,206 A | 5/1998 | Mannheimer |
| 5,746,697 A | 5/1998 | Swedlow et al. |
| 5,747,806 A | 5/1998 | Khalil et al. |
| 5,750,994 A | 5/1998 | Schlager |
| 5,752,914 A | 5/1998 | Delonzor et al. |
| 5,755,226 A | 5/1998 | Carim et al. |
| 5,758,644 A | 6/1998 | Diab et al. |
| 5,760,910 A | 6/1998 | Lepper, Jr. et al. |
| 5,769,785 A | 6/1998 | Diab et al. |
| 5,772,587 A | 6/1998 | Gratton et al. |

(56) References Cited

U.S. PATENT DOCUMENTS

| | | |
|---|---|---|
| 5,772,589 A | 6/1998 | Bernreuter |
| 5,779,630 A | 7/1998 | Fein et al. |
| 5,782,237 A | 7/1998 | Casciani et al. |
| 5,782,756 A | 7/1998 | Mannheimer |
| 5,782,757 A | 7/1998 | Diab et al. |
| 5,785,659 A | 7/1998 | Caro et al. |
| 5,790,729 A | 8/1998 | Pologe et al. |
| 5,791,347 A | 8/1998 | Flaherty et al. |
| 5,792,052 A | 8/1998 | Isaacson et al. |
| 5,793,485 A | 8/1998 | Gourley |
| 5,797,841 A | 8/1998 | Delonzor et al. |
| 5,800,348 A | 9/1998 | Kaestle et al. |
| 5,800,349 A | 9/1998 | Isaacson et al. |
| 5,803,910 A | 9/1998 | Potratz |
| 5,807,246 A | 9/1998 | Sakaguchi et al. |
| 5,807,247 A | 9/1998 | Merchant et al. |
| 5,810,723 A | 9/1998 | Aldrich |
| 5,810,724 A | 9/1998 | Gronvall |
| 5,810,734 A | 9/1998 | Caro et al. |
| 5,817,008 A | 10/1998 | Rafert et al. |
| 5,817,010 A | 10/1998 | Hibi |
| 5,818,985 A | 10/1998 | Merchant et al. |
| 5,823,950 A | 10/1998 | Diab et al. |
| 5,823,952 A | 10/1998 | Levinson et al. |
| 5,827,182 A | 10/1998 | Raley et al. |
| 5,830,121 A | 11/1998 | Enomoto et al. |
| 5,830,131 A | 11/1998 | Caro et al. |
| 5,830,135 A | 11/1998 | Bosque et al. |
| 5,830,137 A | 11/1998 | Sharf |
| 5,833,602 A | 11/1998 | Osemwota |
| 5,833,618 A | 11/1998 | Caro et al. |
| 5,839,439 A | 11/1998 | Nierlich et al. |
| RE36,000 E | 12/1998 | Swedlow et al. |
| 5,842,979 A | 12/1998 | Jarman |
| 5,846,190 A | 12/1998 | Woehrle |
| 5,850,443 A | 12/1998 | Van Oorschot et al. |
| 5,851,178 A | 12/1998 | Aronow |
| 5,851,179 A | 12/1998 | Ritson et al. |
| 5,853,364 A | 12/1998 | Baker, Jr. et al. |
| 5,854,706 A | 12/1998 | Alb |
| 5,857,462 A | 1/1999 | Thomas et al. |
| 5,860,099 A | 1/1999 | Milios et al. |
| 5,860,919 A | 1/1999 | Kiani-Azarbayjany et al. |
| 5,860,932 A | 1/1999 | Goto et al. |
| 5,865,736 A | 2/1999 | Baker, Jr. et al. |
| 5,876,348 A | 3/1999 | Sugo |
| 5,885,213 A | 3/1999 | Richardson et al. |
| 5,890,929 A | 4/1999 | Mills et al. |
| 5,891,022 A | 4/1999 | Pologe |
| 5,891,024 A | 4/1999 | Jarman et al. |
| 5,900,632 A | 5/1999 | Sterling et al. |
| 5,904,654 A | 5/1999 | Wohltmann et al. |
| 5,910,108 A | 6/1999 | Solenberger |
| 5,911,689 A | 6/1999 | Smith et al. |
| 5,916,154 A | 6/1999 | Hobbs et al. |
| 5,919,133 A | 7/1999 | Taylor |
| 5,919,134 A | 7/1999 | Diab |
| 5,921,921 A | 7/1999 | Potratz et al. |
| 5,923,021 A | 7/1999 | Dvorkis et al. |
| 5,924,979 A | 7/1999 | Swedlow |
| 5,934,277 A | 8/1999 | Mortz |
| 5,934,925 A | 8/1999 | Tobler et al. |
| 5,936,986 A | 8/1999 | Cantatore et al. |
| 5,939,609 A | 8/1999 | Knapp et al. |
| 5,940,182 A | 8/1999 | Lepper, Jr. et al. |
| 5,954,644 A | 9/1999 | Dettling |
| 5,976,466 A | 11/1999 | Ratner et al. |
| 5,978,691 A | 11/1999 | Mills |
| 5,983,122 A | 11/1999 | Jarman et al. |
| 5,987,343 A | 11/1999 | Kinast |
| 5,991,355 A | 11/1999 | Dahlke |
| 5,991,467 A | 11/1999 | Kamiko |
| 5,995,855 A | 11/1999 | Kiani et al. |
| 5,995,856 A | 11/1999 | Mannheimer et al. |
| 5,995,859 A | 11/1999 | Takahashi |
| 5,997,343 A | 12/1999 | Mills et al. |
| 5,999,841 A | 12/1999 | Aoyagi et al. |
| 6,002,952 A | 12/1999 | Diab et al. |
| 6,006,119 A | 12/1999 | Soller et al. |
| 6,010,937 A | 1/2000 | Karam et al. |
| 6,011,986 A | 1/2000 | Diab et al. |
| 6,014,576 A | 1/2000 | Raley |
| 6,018,403 A | 1/2000 | Shirakura et al. |
| 6,018,673 A | 1/2000 | Chin et al. |
| 6,018,674 A | 1/2000 | Aronow |
| 6,022,321 A | 2/2000 | Amano et al. |
| 6,023,541 A | 2/2000 | Merchant et al. |
| 6,027,452 A | 2/2000 | Flaherty et al. |
| 6,035,223 A | 3/2000 | Baker, Jr. |
| 6,036,642 A | 3/2000 | Diab et al. |
| 6,040,578 A | 3/2000 | Malin et al. |
| 6,041,247 A | 3/2000 | Weckstrom et al. |
| 6,045,509 A | 4/2000 | Caro et al. |
| 6,058,331 A | 5/2000 | King |
| 6,064,898 A | 5/2000 | Aldrich |
| 6,066,204 A | 5/2000 | Haven |
| 6,067,462 A | 5/2000 | Diab et al. |
| 6,068,594 A | 5/2000 | Schloemer et al. |
| 6,073,037 A | 6/2000 | Alam et al. |
| 6,081,735 A | 6/2000 | Diab et al. |
| 6,083,172 A | 7/2000 | Baker, Jr. et al. |
| 6,088,607 A | 7/2000 | Diab et al. |
| 6,094,592 A | 7/2000 | Yorkey et al. |
| 6,104,938 A | 8/2000 | Huiku |
| 6,110,522 A | 8/2000 | Lepper, Jr. et al. |
| 6,112,107 A | 8/2000 | Hannula |
| 6,115,673 A | 9/2000 | Malin et al. |
| 6,122,042 A | 9/2000 | Wunderman et al. |
| 6,124,597 A | 9/2000 | Shehada et al. |
| 6,126,595 A | 10/2000 | Amano et al. |
| 6,128,521 A | 10/2000 | Marro et al. |
| 6,129,675 A | 10/2000 | Jay |
| 6,132,363 A | 10/2000 | Freed et al. |
| 6,133,871 A | 10/2000 | Krasner |
| 6,144,868 A | 11/2000 | Parker |
| 6,149,588 A | 11/2000 | Noda et al. |
| 6,151,516 A | 11/2000 | Kiani-Azarbayjany et al. |
| 6,151,518 A | 11/2000 | Hayashi |
| 6,152,754 A | 11/2000 | Gerhardt et al. |
| 6,154,667 A | 11/2000 | Miura et al. |
| 6,157,041 A | 12/2000 | Thomas et al. |
| 6,157,850 A | 12/2000 | Diab et al. |
| 6,163,715 A | 12/2000 | Larsen et al. |
| 6,165,005 A | 12/2000 | Mills et al. |
| 6,165,173 A | 12/2000 | Kamdar et al. |
| 6,167,303 A | 12/2000 | Thompson |
| 6,174,283 B1 | 1/2001 | Nevo et al. |
| 6,175,752 B1 | 1/2001 | Say et al. |
| 6,178,343 B1 | 1/2001 | Bindszus et al. |
| 6,184,521 B1 | 2/2001 | Coffin, IV et al. |
| 6,185,454 B1 | 2/2001 | Thompson |
| 6,192,261 B1 | 2/2001 | Gratton et al. |
| 6,198,951 B1 | 3/2001 | Kosuda et al. |
| 6,206,830 B1 | 3/2001 | Diab et al. |
| 6,223,063 B1 | 4/2001 | Chaiken et al. |
| 6,226,539 B1 | 5/2001 | Potratz |
| 6,229,856 B1 | 5/2001 | Diab et al. |
| 6,230,035 B1 | 5/2001 | Aoyagi et al. |
| 6,232,609 B1 | 5/2001 | Snyder et al. |
| 6,236,872 B1 | 5/2001 | Diab et al. |
| 6,237,604 B1 | 5/2001 | Burnside et al. |
| 6,241,683 B1 | 6/2001 | Macklem et al. |
| 6,248,083 B1 | 6/2001 | Smith et al. |
| 6,253,097 B1 | 6/2001 | Aronow et al. |
| 6,255,708 B1 | 7/2001 | Sudharsanan et al. |
| 6,256,523 B1 | 7/2001 | Diab et al. |
| 6,262,698 B1 | 7/2001 | Blum |
| 6,263,222 B1 | 7/2001 | Diab et al. |
| 6,266,551 B1 | 7/2001 | Osadchy et al. |
| 6,270,223 B1 | 8/2001 | Del Bon et al. |
| 6,272,363 B1 | 8/2001 | Casciani et al. |
| 6,278,522 B1 | 8/2001 | Lepper, Jr. et al. |
| 6,280,213 B1 | 8/2001 | Tobler et al. |
| 6,280,381 B1 | 8/2001 | Malin et al. |

(56) References Cited

U.S. PATENT DOCUMENTS

| | | |
|---|---|---|
| 6,285,895 B1 | 9/2001 | Ristolainen et al. |
| 6,285,896 B1 | 9/2001 | Tobler et al. |
| 6,293,915 B1 | 9/2001 | Amano et al. |
| 6,295,330 B1 | 9/2001 | Skog et al. |
| 6,297,906 B1 | 10/2001 | Allen et al. |
| 6,298,252 B1 | 10/2001 | Kovach et al. |
| 6,298,255 B1 | 10/2001 | Cordero et al. |
| 6,301,493 B1 | 10/2001 | Marro et al. |
| 6,304,675 B1 | 10/2001 | Osbourn et al. |
| 6,304,767 B1 | 10/2001 | Soller et al. |
| 6,308,089 B1 | 10/2001 | von der Ruhr et al. |
| 6,317,627 B1 | 11/2001 | Ennen et al. |
| 6,321,100 B1 | 11/2001 | Parker |
| 6,325,761 B1 | 12/2001 | Jay |
| 6,330,468 B1 | 12/2001 | Scharf |
| 6,334,065 B1 | 12/2001 | Al-Ali et al. |
| 6,336,900 B1 | 1/2002 | Alleckson et al. |
| 6,339,715 B1 | 1/2002 | Bahr et al. |
| 6,341,257 B1 | 1/2002 | Haaland |
| 6,343,224 B1 | 1/2002 | Parker |
| 6,349,228 B1 | 2/2002 | Kiani et al. |
| 6,351,217 B1 | 2/2002 | Kuhn |
| 6,351,658 B1 | 2/2002 | Middleman et al. |
| 6,356,774 B1 | 3/2002 | Bernstein et al. |
| 6,360,113 B1 | 3/2002 | Dettling |
| 6,360,114 B1 | 3/2002 | Diab et al. |
| 6,363,269 B1 | 3/2002 | Hanna et al. |
| 6,368,283 B1 | 4/2002 | Xu et al. |
| 6,371,921 B1 | 4/2002 | Caro et al. |
| 6,374,129 B1 | 4/2002 | Chin et al. |
| 6,377,828 B1 | 4/2002 | Chaiken et al. |
| 6,377,829 B1 | 4/2002 | Al-Ali |
| 6,388,240 B2 | 5/2002 | Schulz et al. |
| 6,393,310 B1 | 5/2002 | Kuenstner |
| 6,393,311 B1 | 5/2002 | Edgar et al. |
| 6,396,873 B1 | 5/2002 | Goldstein et al. |
| 6,397,091 B2 | 5/2002 | Diab et al. |
| 6,397,092 B1 | 5/2002 | Norris et al. |
| 6,397,093 B1 | 5/2002 | Aldrich |
| 6,398,727 B1 | 6/2002 | Bui et al. |
| 6,402,690 B1 | 6/2002 | Rhee et al. |
| 6,408,198 B1 | 6/2002 | Hanna et al. |
| 6,411,373 B1 | 6/2002 | Garside et al. |
| 6,411,833 B1 | 6/2002 | Baker, Jr. et al. |
| 6,415,166 B1 | 7/2002 | Van Hoy et al. |
| 6,415,167 B1 | 7/2002 | Blank et al. |
| 6,415,233 B1 | 7/2002 | Haaland |
| 6,415,236 B2 | 7/2002 | Kobayashi et al. |
| 6,421,549 B1 | 7/2002 | Jacques |
| 6,430,423 B2 | 8/2002 | DeLonzor et al. |
| 6,430,437 B1 | 8/2002 | Marro |
| 6,430,525 B1 | 8/2002 | Weber et al. |
| 6,434,408 B1 | 8/2002 | Heckel |
| 6,441,388 B1 | 8/2002 | Thomas et al. |
| 6,453,184 B1 | 9/2002 | Hyogo et al. |
| 6,455,340 B1 | 9/2002 | Chua et al. |
| 6,463,310 B1 | 10/2002 | Swedlow et al. |
| 6,463,311 B1 | 10/2002 | Diab |
| 6,466,824 B1 | 10/2002 | Struble |
| 6,470,199 B1 | 10/2002 | Kopotic et al. |
| 6,473,008 B2 | 10/2002 | Kelly et al. |
| 6,480,729 B2 | 11/2002 | Stone |
| 6,487,429 B2 | 11/2002 | Hockersmith et al. |
| 6,490,466 B1 | 12/2002 | Fein et al. |
| 6,490,684 B1 | 12/2002 | Fenstemaker et al. |
| 6,497,659 B1 | 12/2002 | Rafert |
| 6,501,974 B2 | 12/2002 | Huiku |
| 6,501,975 B2 | 12/2002 | Diab et al. |
| 6,504,943 B1 | 1/2003 | Sweatt et al. |
| 6,505,059 B1 | 1/2003 | Kollias et al. |
| 6,505,060 B1 | 1/2003 | Norris |
| 6,505,061 B2 | 1/2003 | Larson |
| 6,505,133 B1 | 1/2003 | Hanna |
| 6,510,329 B2 | 1/2003 | Heckel |
| 6,515,273 B2 | 2/2003 | Al-Ali |
| 6,519,486 B1 | 2/2003 | Edgar, Jr. et al. |
| 6,519,487 B1 | 2/2003 | Parker |
| 6,522,398 B2 | 2/2003 | Cadell et al. |
| 6,525,386 B1 | 2/2003 | Mills et al. |
| 6,526,300 B1 | 2/2003 | Kiani et al. |
| 6,526,301 B2 | 2/2003 | Larsen et al. |
| 6,527,729 B1 | 3/2003 | Turcott |
| 6,528,809 B1 | 3/2003 | Thomas et al. |
| 6,534,012 B1 | 3/2003 | Hazen et al. |
| 6,537,225 B1 | 3/2003 | Mills |
| 6,541,756 B2 | 4/2003 | Schulz et al. |
| 6,542,763 B1 | 4/2003 | Yamashita et al. |
| 6,542,764 B1 | 4/2003 | Al-Ali et al. |
| 6,545,652 B1 | 4/2003 | Tsuji |
| 6,546,267 B1 | 4/2003 | Sugiura |
| 6,553,241 B2 | 4/2003 | Mannheimer et al. |
| 6,553,242 B1 | 4/2003 | Sarussi |
| 6,556,852 B1 | 4/2003 | Schulz et al. |
| 6,564,077 B2 | 5/2003 | Mortara |
| 6,571,113 B1 | 5/2003 | Fein et al. |
| 6,580,086 B1 | 6/2003 | Schulz et al. |
| 6,582,964 B1 | 6/2003 | Samsoondar et al. |
| 6,584,336 B1 | 6/2003 | Ali et al. |
| 6,584,413 B1 | 6/2003 | Keenan et al. |
| 6,587,196 B1 | 7/2003 | Stippick et al. |
| 6,587,199 B1 | 7/2003 | Luu |
| 6,591,123 B2 | 7/2003 | Fein et al. |
| 6,594,511 B2 | 7/2003 | Stone et al. |
| 6,594,518 B1 | 7/2003 | Benaron et al. |
| 6,595,316 B2 | 7/2003 | Cybulski et al. |
| 6,596,016 B1 | 7/2003 | Vreman et al. |
| 6,597,932 B2 | 7/2003 | Tian et al. |
| 6,597,933 B2 | 7/2003 | Kiani et al. |
| 6,600,940 B1 | 7/2003 | Fein et al. |
| 6,606,509 B2 | 8/2003 | Schmitt |
| 6,606,510 B2 | 8/2003 | Swedlow et al. |
| 6,606,511 B1 | 8/2003 | Ali et al. |
| 6,609,016 B1 | 8/2003 | Lynn |
| 6,611,698 B1 | 8/2003 | Yamashita et al. |
| 6,614,521 B2 | 9/2003 | Samsoondar et al. |
| 6,615,064 B1 | 9/2003 | Aldrich |
| 6,615,151 B1 | 9/2003 | Scecina et al. |
| 6,618,602 B2 | 9/2003 | Levin |
| 6,622,095 B2 | 9/2003 | Kobayashi et al. |
| 6,628,975 B1 | 9/2003 | Fein et al. |
| 6,631,281 B1 | 10/2003 | Kastle |
| 6,632,181 B2 | 10/2003 | Flaherty et al. |
| 6,635,559 B2 | 10/2003 | Greenwald et al. |
| 6,639,668 B1 | 10/2003 | Trepagnier |
| 6,640,116 B2 | 10/2003 | Diab |
| 6,640,117 B2 | 10/2003 | Makarewicz et al. |
| 6,643,530 B2 | 11/2003 | Diab et al. |
| 6,645,142 B2 | 11/2003 | Braig et al. |
| 6,650,917 B2 | 11/2003 | Diab et al. |
| 6,654,623 B1 | 11/2003 | Kastle |
| 6,654,624 B2 | 11/2003 | Diab et al. |
| 6,657,717 B2 | 12/2003 | Cadell et al. |
| 6,658,276 B2 | 12/2003 | Kiani et al. |
| 6,658,277 B2 | 12/2003 | Wasserman |
| 6,661,161 B1 | 12/2003 | Lanzo et al. |
| 6,662,033 B2 | 12/2003 | Casciani et al. |
| 6,665,551 B1 | 12/2003 | Suzuki |
| 6,668,183 B2 | 12/2003 | Hicks et al. |
| 6,671,526 B1 | 12/2003 | Aoyagi et al. |
| 6,671,531 B2 | 12/2003 | Al-Ali |
| 6,675,031 B1 | 1/2004 | Porges et al. |
| 6,675,106 B1 | 1/2004 | Keenan et al. |
| 6,676,600 B1 | 1/2004 | Conero et al. |
| 6,678,543 B2 | 1/2004 | Diab et al. |
| 6,681,126 B2 | 1/2004 | Solenberger |
| 6,684,090 B2 | 1/2004 | Ali et al. |
| 6,684,091 B2 | 1/2004 | Parker |
| 6,687,620 B1 | 2/2004 | Haaland et al. |
| 6,690,466 B2 | 2/2004 | Miller et al. |
| 6,694,157 B1 | 2/2004 | Stone et al. |
| 6,697,655 B2 | 2/2004 | Sueppel et al. |
| 6,697,656 B1 | 2/2004 | Al-Ali |
| 6,697,657 B1 | 2/2004 | Shehada et al. |
| 6,697,658 B2 | 2/2004 | Al-Ali |

(56) References Cited

U.S. PATENT DOCUMENTS

| | | |
|---|---|---|
| RE38,476 E | 3/2004 | Diab et al. |
| 6,699,194 B1 | 3/2004 | Diab et al. |
| 6,701,170 B2 | 3/2004 | Stetson |
| 6,708,049 B1 | 3/2004 | Berson et al. |
| 6,711,503 B2 | 3/2004 | Haaland |
| 6,714,803 B1 | 3/2004 | Mortz |
| 6,714,804 B2 | 3/2004 | Al-Ali et al. |
| 6,714,805 B2 | 3/2004 | Jeon et al. |
| RE38,492 E | 4/2004 | Diab et al. |
| 6,719,705 B2 | 4/2004 | Mills |
| 6,720,734 B2 | 4/2004 | Norris |
| 6,721,582 B2 | 4/2004 | Trepagnier et al. |
| 6,721,584 B2 | 4/2004 | Baker, Jr. et al. |
| 6,721,585 B1 | 4/2004 | Parker |
| 6,725,074 B1 | 4/2004 | Kastle |
| 6,725,075 B2 | 4/2004 | Al-Ali |
| 6,726,634 B2 | 4/2004 | Freeman |
| 6,728,560 B2 | 4/2004 | Kollias et al. |
| 6,735,459 B2 | 5/2004 | Parker |
| 6,738,652 B2 | 5/2004 | Mattu et al. |
| 6,741,875 B1 | 5/2004 | Pawluczyk et al. |
| 6,741,876 B1 | 5/2004 | Scecina et al. |
| 6,743,172 B1 | 6/2004 | Blike |
| 6,745,060 B2 | 6/2004 | Diab et al. |
| 6,745,061 B1 | 6/2004 | Hicks et al. |
| 6,748,253 B2 | 6/2004 | Norris et al. |
| 6,748,254 B2 | 6/2004 | O'Neil et al. |
| 6,754,515 B1 | 6/2004 | Pologe |
| 6,754,516 B2 | 6/2004 | Mannheimer |
| 6,760,607 B2 | 7/2004 | Al-Ali |
| 6,760,609 B2 | 7/2004 | Jacques |
| 6,770,028 B1 | 8/2004 | Ali et al. |
| 6,771,994 B2 | 8/2004 | Kiani et al. |
| 6,773,397 B2 | 8/2004 | Kelly |
| 6,778,923 B2 | 8/2004 | Norris et al. |
| 6,780,158 B2 | 8/2004 | Yarita |
| 6,788,849 B1 | 9/2004 | Pawluczyk |
| 6,788,965 B2 | 9/2004 | Ruchti et al. |
| 6,792,300 B1 | 9/2004 | Diab et al. |
| 6,800,373 B2 | 10/2004 | Gorczyca |
| 6,801,797 B2 | 10/2004 | Mannheimer et al. |
| 6,801,799 B2 | 10/2004 | Mendelson |
| 6,810,277 B2 | 10/2004 | Edgar, Jr. et al. |
| 6,813,511 B2 | 11/2004 | Diab et al. |
| 6,816,241 B2 | 11/2004 | Grubisic |
| 6,816,741 B2 | 11/2004 | Diab |
| 6,819,950 B2 | 11/2004 | Mills |
| 6,822,564 B2 | 11/2004 | Al-Ali |
| 6,825,619 B2 | 11/2004 | Norris |
| 6,826,419 B2 | 11/2004 | Diab et al. |
| 6,829,496 B2 | 12/2004 | Nagai et al. |
| 6,829,501 B2 | 12/2004 | Nielsen et al. |
| 6,830,711 B2 | 12/2004 | Mills et al. |
| 6,836,679 B2 | 12/2004 | Baker, Jr. et al. |
| 6,839,579 B1 | 1/2005 | Chin |
| 6,839,580 B2 | 1/2005 | Zonios et al. |
| 6,839,582 B2 | 1/2005 | Heckel |
| 6,842,702 B2 | 1/2005 | Haaland et al. |
| 6,845,256 B2 | 1/2005 | Chin et al. |
| 6,847,835 B1 | 1/2005 | Yamanishi |
| 6,850,787 B2 | 2/2005 | Weber et al. |
| 6,850,788 B2 | 2/2005 | Al-Ali |
| 6,852,083 B2 | 2/2005 | Caro et al. |
| 6,853,304 B2 | 2/2005 | Reisman |
| 6,861,639 B2 | 3/2005 | Al-Ali |
| 6,861,641 B1 | 3/2005 | Adams |
| 6,869,402 B2 | 3/2005 | Arnold |
| 6,871,089 B2 | 3/2005 | Korzinov et al. |
| 6,876,931 B2 | 4/2005 | Lorenz et al. |
| 6,882,874 B2 | 4/2005 | Huiku |
| 6,898,452 B2 | 5/2005 | Al-Ali et al. |
| 6,912,049 B2 | 6/2005 | Pawluczyk et al. |
| 6,912,413 B2 | 6/2005 | Rantala et al. |
| 6,917,422 B2 | 7/2005 | Samsoondar et al. |
| 6,919,566 B1 | 7/2005 | Cadell |
| 6,920,345 B2 | 7/2005 | Al-Ali et al. |
| 6,921,367 B2 | 7/2005 | Mills |
| 6,922,645 B2 | 7/2005 | Haaland et al. |
| 6,928,311 B1 | 8/2005 | Pawluczyk et al. |
| 6,931,268 B1 | 8/2005 | Kiani-Azarbayjany et al. |
| 6,931,269 B2 | 8/2005 | Terry |
| 6,934,570 B2 | 8/2005 | Kiani et al. |
| 6,939,305 B2 | 9/2005 | Flaherty et al. |
| 6,943,348 B1 | 9/2005 | Coffin, IV |
| 6,944,487 B2 | 9/2005 | Maynard et al. |
| 6,950,687 B2 | 9/2005 | Al-Ali |
| 6,956,572 B2 | 10/2005 | Zaleski |
| 6,956,649 B2 | 10/2005 | Acosta et al. |
| 6,961,598 B2 | 11/2005 | Diab |
| 6,970,792 B1 | 11/2005 | Diab |
| 6,975,891 B2 | 12/2005 | Pawluczyk |
| 6,979,812 B2 | 12/2005 | Al-Ali |
| 6,985,764 B2 | 1/2006 | Mason et al. |
| 6,987,994 B1 | 1/2006 | Mortz |
| 6,990,364 B2 | 1/2006 | Ruchti et al. |
| 6,993,371 B2 | 1/2006 | Kiani et al. |
| 6,996,427 B2 | 2/2006 | Ali et al. |
| 6,998,247 B2 | 2/2006 | Monfre et al. |
| 6,999,685 B1 | 2/2006 | Kawase et al. |
| 6,999,904 B2 | 2/2006 | Weber et al. |
| 7,001,337 B2 | 2/2006 | Dekker |
| 7,003,338 B2 | 2/2006 | Weber et al. |
| 7,003,339 B2 | 2/2006 | Diab et al. |
| 7,006,856 B2 | 2/2006 | Baker, Jr. et al. |
| 7,015,451 B2 | 3/2006 | Dalke et al. |
| 7,024,233 B2 | 4/2006 | Ali et al. |
| 7,027,849 B2 | 4/2006 | Al-Ali |
| 7,030,749 B2 | 4/2006 | Al-Ali |
| 7,031,728 B2 | 4/2006 | Beyer, Jr. |
| 7,039,449 B2 | 5/2006 | Al-Ali |
| 7,041,060 B2 | 5/2006 | Flaherty et al. |
| 7,044,918 B2 | 5/2006 | Diab |
| 7,067,893 B2 | 6/2006 | Mills et al. |
| D526,719 S | 8/2006 | Richie, Jr. et al. |
| 7,088,040 B1 | 8/2006 | Ducharme et al. |
| 7,092,735 B2 | 8/2006 | Osann, Jr. |
| 7,096,052 B2 | 8/2006 | Mason et al. |
| 7,096,054 B2 | 8/2006 | Abdul-Hafiz et al. |
| 7,107,706 B1 | 9/2006 | Bailey, Sr. et al. |
| D529,616 S | 10/2006 | Deros et al. |
| 7,130,672 B2 | 10/2006 | Pewzner et al. |
| 7,132,641 B2 | 11/2006 | Schulz et al. |
| 7,133,710 B2 | 11/2006 | Acosta et al. |
| 7,142,901 B2 | 11/2006 | Kiani et al. |
| 7,149,561 B2 | 12/2006 | Diab |
| 7,186,966 B2 | 3/2007 | Al-Ali |
| 7,190,261 B2 | 3/2007 | Al-Ali |
| 7,215,984 B2 | 5/2007 | Diab et al. |
| 7,215,986 B2 | 5/2007 | Diab et al. |
| 7,221,971 B2 | 5/2007 | Diab et al. |
| 7,225,006 B2 | 5/2007 | Al-Ali et al. |
| 7,225,007 B2 | 5/2007 | Al-Ali et al. |
| RE39,672 E | 6/2007 | Shehada et al. |
| 7,230,227 B2 | 6/2007 | Wilcken et al. |
| 7,239,905 B2 | 7/2007 | Kiani-Azarbayjany et al. |
| 7,245,953 B1 | 7/2007 | Parker |
| 7,251,513 B2 | 7/2007 | Kondoh et al. |
| 7,254,429 B2 | 8/2007 | Schurman et al. |
| 7,254,431 B2 | 8/2007 | Al-Ali et al. |
| 7,254,433 B2 | 8/2007 | Diab et al. |
| 7,254,434 B2 | 8/2007 | Schulz et al. |
| 7,272,425 B2 | 9/2007 | Al-Ali |
| 7,274,955 B2 | 9/2007 | Kiani et al. |
| D554,263 S | 10/2007 | Al-Ali |
| 7,280,858 B2 | 10/2007 | Al-Ali et al. |
| 7,289,835 B2 | 10/2007 | Mansfield et al. |
| 7,292,883 B2 | 11/2007 | De Felice et al. |
| 7,295,866 B2 | 11/2007 | Al-Ali |
| 7,299,080 B2 | 11/2007 | Acosta et al. |
| 7,328,053 B1 | 2/2008 | Diab et al. |
| 7,332,784 B2 | 2/2008 | Mills et al. |
| 7,340,287 B2 | 3/2008 | Mason et al. |
| 7,341,559 B2 | 3/2008 | Schulz et al. |
| 7,343,186 B2 | 3/2008 | Lamego et al. |

(56) References Cited

U.S. PATENT DOCUMENTS

| | | |
|---|---|---|
| D566,282 S | 4/2008 | Al-Ali et al. |
| 7,355,512 B1 | 4/2008 | Al-Ali |
| 7,356,365 B2 | 4/2008 | Schurman |
| 7,371,981 B2 | 5/2008 | Abdul-Hafiz |
| 7,373,193 B2 | 5/2008 | Al-Ali et al. |
| 7,373,194 B2 | 5/2008 | Weber et al. |
| 7,376,453 B1 | 5/2008 | Diab et al. |
| 7,377,794 B2 | 5/2008 | Al-Ali et al. |
| 7,377,899 B2 | 5/2008 | Weber et al. |
| 7,383,070 B2 | 6/2008 | Diab et al. |
| 7,395,158 B2 | 7/2008 | Monfre et al. |
| 7,415,297 B2 | 8/2008 | Al-Ali et al. |
| 7,428,432 B2 | 9/2008 | Ali et al. |
| 7,438,683 B2 | 10/2008 | Al-Ali et al. |
| 7,440,787 B2 | 10/2008 | Diab |
| 7,454,240 B2 | 11/2008 | Diab et al. |
| 7,457,652 B2 | 11/2008 | Porges et al. |
| 7,467,002 B2 | 12/2008 | Weber et al. |
| 7,469,157 B2 | 12/2008 | Diab et al. |
| 7,471,969 B2 | 12/2008 | Diab et al. |
| 7,471,971 B2 | 12/2008 | Diab et al. |
| 7,483,729 B2 | 1/2009 | Al-Ali et al. |
| 7,483,730 B2 | 1/2009 | Diab et al. |
| 7,489,958 B2 | 2/2009 | Diab et al. |
| 7,496,391 B2 | 2/2009 | Diab et al. |
| 7,496,393 B2 | 2/2009 | Diab et al. |
| D587,657 S | 3/2009 | Al-Ali et al. |
| 7,499,741 B2 | 3/2009 | Diab et al. |
| 7,499,835 B2 | 3/2009 | Weber et al. |
| 7,500,950 B2 | 3/2009 | Al-Ali et al. |
| 7,509,153 B2 | 3/2009 | Blank et al. |
| 7,509,154 B2 | 3/2009 | Diab et al. |
| 7,509,494 B2 | 3/2009 | Al-Ali |
| 7,510,849 B2 | 3/2009 | Schurman et al. |
| 7,514,725 B2 | 4/2009 | Wojtczuk et al. |
| 7,519,406 B2 | 4/2009 | Blank et al. |
| 7,526,328 B2 | 4/2009 | Diab et al. |
| D592,507 S | 5/2009 | Wachman et al. |
| 7,530,942 B1 | 5/2009 | Diab |
| 7,530,949 B2 | 5/2009 | Al Ali et al. |
| 7,530,955 B2 | 5/2009 | Diab et al. |
| 7,558,622 B2 | 7/2009 | Tran |
| 7,563,110 B2 | 7/2009 | Al-Ali et al. |
| 7,593,230 B2 | 9/2009 | Abul-Haj et al. |
| 7,596,398 B2 | 9/2009 | Al-Ali et al. |
| 7,606,608 B2 | 10/2009 | Blank et al. |
| 7,606,861 B2 | 10/2009 | Killcommons et al. |
| 7,618,375 B2 | 11/2009 | Flaherty et al. |
| 7,620,674 B2 | 11/2009 | Ruchti et al. |
| D606,659 S | 12/2009 | Flaherty et al. |
| 7,629,039 B2 | 12/2009 | Eckerbom et al. |
| 7,640,140 B2 | 12/2009 | Ruchti et al. |
| 7,647,083 B2 | 1/2010 | Al-Ali et al. |
| D609,193 S | 2/2010 | Al-Ali et al. |
| 7,656,393 B2 | 2/2010 | King et al. |
| 7,658,613 B1 | 2/2010 | Griffin et al. |
| 7,670,726 B2 | 3/2010 | Lu |
| 7,676,253 B2 | 3/2010 | Raridan, Jr. |
| 7,679,519 B2 | 3/2010 | Lindner et al. |
| 7,683,926 B2 | 3/2010 | Schechterman et al. |
| D614,305 S | 4/2010 | Al-Ali et al. |
| 7,697,966 B2 | 4/2010 | Monfre et al. |
| 7,698,105 B2 | 4/2010 | Ruchti et al. |
| 7,698,909 B2 | 4/2010 | Hannula et al. |
| RE41,317 E | 5/2010 | Parker |
| RE41,333 E | 5/2010 | Blank et al. |
| 7,729,733 B2 | 6/2010 | Al-Ali et al. |
| 7,734,320 B2 | 6/2010 | Al-Ali |
| 7,761,127 B2 | 7/2010 | Al-Ali et al. |
| 7,761,128 B2 | 7/2010 | Al-Ali et al. |
| 7,764,982 B2 | 7/2010 | Dalke et al. |
| D621,516 S | 8/2010 | Kiani et al. |
| 7,791,155 B2 | 9/2010 | Diab |
| 7,801,581 B2 | 9/2010 | Diab |
| 7,822,452 B2 | 10/2010 | Schurman et al. |
| RE41,912 E | 11/2010 | Parker |
| 7,844,313 B2 | 11/2010 | Kiani et al. |
| 7,844,314 B2 | 11/2010 | Al-Ali |
| 7,844,315 B2 | 11/2010 | Al-Ali |
| 7,865,222 B2 | 1/2011 | Weber et al. |
| 7,869,849 B2 | 1/2011 | Ollerdessen et al. |
| 7,873,497 B2 | 1/2011 | Weber et al. |
| 7,880,606 B2 | 2/2011 | Al-Ali |
| 7,880,626 B2 | 2/2011 | Al-Ali et al. |
| 7,891,355 B2 | 2/2011 | Al-Ali et al. |
| 7,894,868 B2 | 2/2011 | Al-Ali et al. |
| 7,899,507 B2 | 3/2011 | Al-Ali et al. |
| 7,899,518 B2 | 3/2011 | Trepagnier et al. |
| 7,904,130 B2 | 3/2011 | Raridan, Jr. |
| 7,904,132 B2 | 3/2011 | Weber et al. |
| 7,909,772 B2 | 3/2011 | Popov et al. |
| 7,910,875 B2 | 3/2011 | Al-Ali |
| 7,918,779 B2 | 4/2011 | Haber et al. |
| 7,919,713 B2 | 4/2011 | Al-Ali et al. |
| 7,937,128 B2 | 5/2011 | Al-Ali |
| 7,937,129 B2 | 5/2011 | Mason et al. |
| 7,937,130 B2 | 5/2011 | Diab et al. |
| 7,941,199 B2 | 5/2011 | Kiani |
| 7,951,086 B2 | 5/2011 | Flaherty et al. |
| 7,957,780 B2 | 6/2011 | Lamego et al. |
| 7,962,188 B2 | 6/2011 | Kiani et al. |
| 7,962,190 B1 | 6/2011 | Diab et al. |
| 7,976,472 B2 | 7/2011 | Kiani |
| 7,988,637 B2 | 8/2011 | Diab |
| 7,990,382 B2 | 8/2011 | Kiani |
| 7,991,446 B2 | 8/2011 | Ali et al. |
| 8,000,761 B2 | 8/2011 | Al-Ali |
| 8,008,088 B2 | 8/2011 | Bellott et al. |
| RE42,753 E | 9/2011 | Kiani-Azarbayjany et al. |
| 8,019,400 B2 | 9/2011 | Diab et al. |
| 8,028,701 B2 | 10/2011 | Al-Ali et al. |
| 8,029,765 B2 | 10/2011 | Bellott et al. |
| 8,036,727 B2 | 10/2011 | Schurman et al. |
| 8,036,728 B2 | 10/2011 | Diab et al. |
| 8,040,758 B1 | 10/2011 | Dickinson |
| 8,046,040 B2 | 10/2011 | Ali et al. |
| 8,046,041 B2 | 10/2011 | Diab et al. |
| 8,046,042 B2 | 10/2011 | Diab et al. |
| 8,048,040 B2 | 11/2011 | Kiani |
| 8,050,728 B2 | 11/2011 | Al-Ali et al. |
| RE43,169 E | 2/2012 | Parker |
| 8,116,837 B2 | 2/2012 | Huang |
| 8,118,620 B2 | 2/2012 | Al-Ali et al. |
| 8,126,528 B2 | 2/2012 | Diab et al. |
| 8,128,572 B2 | 3/2012 | Diab et al. |
| 8,130,105 B2 | 3/2012 | Al-Ali et al. |
| 8,145,287 B2 | 3/2012 | Diab et al. |
| 8,150,487 B2 | 4/2012 | Diab et al. |
| 8,175,672 B2 | 5/2012 | Parker |
| 8,177,720 B2 | 5/2012 | Nanba et al. |
| 8,180,420 B2 | 5/2012 | Diab et al. |
| 8,182,443 B1 | 5/2012 | Kiani |
| 8,185,180 B2 | 5/2012 | Diab et al. |
| 8,190,223 B2 | 5/2012 | Al-Ali et al. |
| 8,190,227 B2 | 5/2012 | Diab et al. |
| 8,203,438 B2 | 6/2012 | Kiani et al. |
| 8,203,704 B2 | 6/2012 | Merritt et al. |
| 8,204,566 B2 | 6/2012 | Schurman et al. |
| 8,219,172 B2 | 7/2012 | Schurman et al. |
| 8,224,411 B2 | 7/2012 | Al-Ali et al. |
| 8,228,181 B2 | 7/2012 | Al-Ali |
| 8,229,532 B2 | 7/2012 | Davis |
| 8,229,533 B2 | 7/2012 | Diab et al. |
| 8,233,955 B2 | 7/2012 | Al-Ali et al. |
| 8,244,325 B2 | 8/2012 | Al-Ali et al. |
| 8,255,026 B1 | 8/2012 | Al-Ali |
| 8,255,027 B2 | 8/2012 | Al-Ali et al. |
| 8,255,028 B2 | 8/2012 | Al-Ali et al. |
| 8,260,577 B2 | 9/2012 | Weber et al. |
| 8,265,723 B1 | 9/2012 | McHale et al. |
| 8,274,360 B2 | 9/2012 | Sampath et al. |
| 8,280,473 B2 | 10/2012 | Al-Ali |
| 8,301,217 B2 | 10/2012 | Al-Ali et al. |
| 8,306,596 B2 | 11/2012 | Schurman et al. |

(56) References Cited

U.S. PATENT DOCUMENTS

| | | |
|---|---|---|
| 8,310,336 B2 | 11/2012 | Muhsin et al. |
| 8,315,683 B2 | 11/2012 | Al-Ali et al. |
| RE43,860 E | 12/2012 | Parker |
| 8,337,403 B2 | 12/2012 | Al-Ali et al. |
| 8,343,026 B2 | 1/2013 | Gardiner et al. |
| 8,346,330 B2 | 1/2013 | Lamego |
| 8,353,842 B2 | 1/2013 | Al-Ali et al. |
| 8,355,766 B2 | 1/2013 | MacNeish, III et al. |
| 8,359,080 B2 | 1/2013 | Diab et al. |
| 8,364,223 B2 | 1/2013 | Al-Ali et al. |
| 8,364,226 B2 | 1/2013 | Diab et al. |
| 8,374,665 B2 | 2/2013 | Lamego |
| 8,374,825 B2 | 2/2013 | Vock et al. |
| 8,385,995 B2 | 2/2013 | Al-Ali et al. |
| 8,385,996 B2 | 2/2013 | Smith et al. |
| 8,388,353 B2 | 3/2013 | Kiani et al. |
| 8,399,822 B2 | 3/2013 | Al-Ali |
| 8,401,602 B2 | 3/2013 | Kiani |
| 8,405,608 B2 | 3/2013 | Al-Ali et al. |
| 8,414,499 B2 | 4/2013 | Al-Ali et al. |
| 8,418,524 B2 | 4/2013 | Al-Ali |
| 8,423,106 B2 | 4/2013 | Lamego et al. |
| 8,428,967 B2 | 4/2013 | Olsen et al. |
| 8,430,817 B1 | 4/2013 | Al-Ali et al. |
| 8,437,825 B2 | 5/2013 | Dalvi et al. |
| 8,455,290 B2 | 6/2013 | Siskavich |
| 8,457,703 B2 | 6/2013 | Al-Ali |
| 8,457,707 B2 | 6/2013 | Kiani |
| 8,463,349 B2 | 6/2013 | Diab et al. |
| 8,466,286 B2 | 6/2013 | Bellott et al. |
| 8,471,713 B2 | 6/2013 | Poeze et al. |
| 8,473,020 B2 | 6/2013 | Kiani et al. |
| 8,483,787 B2 | 7/2013 | Al-Ali et al. |
| 8,487,256 B2 | 7/2013 | Kwong et al. |
| 8,489,364 B2 | 7/2013 | Weber et al. |
| 8,498,684 B2 | 7/2013 | Weber et al. |
| 8,504,128 B2 | 8/2013 | Blank et al. |
| 8,509,867 B2 | 8/2013 | Workman et al. |
| 8,515,509 B2 | 8/2013 | Bruinsma et al. |
| 8,515,511 B2 | 8/2013 | Boutelle |
| 8,515,515 B2 | 8/2013 | McKenna et al. |
| 8,523,781 B2 | 9/2013 | Al-Ali |
| 8,529,301 B2 | 9/2013 | Al-Ali et al. |
| 8,532,727 B2 | 9/2013 | Ali et al. |
| 8,532,728 B2 | 9/2013 | Diab et al. |
| D692,145 S | 10/2013 | Al-Ali et al. |
| 8,547,209 B2 | 10/2013 | Kiani et al. |
| 8,548,548 B2 | 10/2013 | Al-Ali |
| 8,548,549 B2 | 10/2013 | Schurman et al. |
| 8,548,550 B2 | 10/2013 | Al-Ali et al. |
| 8,560,032 B2 | 10/2013 | Al-Ali et al. |
| 8,560,034 B1 | 10/2013 | Diab et al. |
| 8,570,167 B2 | 10/2013 | Al-Ali |
| 8,570,503 B2 | 10/2013 | Vo et al. |
| 8,571,617 B2 | 10/2013 | Reichgott et al. |
| 8,571,618 B1 | 10/2013 | Lamego et al. |
| 8,571,619 B2 | 10/2013 | Al-Ali et al. |
| 8,577,431 B2 | 11/2013 | Lamego et al. |
| 8,581,732 B2 | 11/2013 | Al-Ali et al. |
| 8,584,345 B2 | 11/2013 | Al-Ali et al. |
| 8,588,880 B2 | 11/2013 | Abdul-Hafiz et al. |
| 8,600,467 B2 | 12/2013 | Al-Ali et al. |
| 8,600,494 B2 | 12/2013 | Schroeppel et al. |
| 8,606,342 B2 | 12/2013 | Diab |
| 8,611,095 B2 | 12/2013 | Kwong et al. |
| 8,626,255 B2 | 1/2014 | Al-Ali et al. |
| 8,630,691 B2 | 1/2014 | Lamego et al. |
| 8,634,889 B2 | 1/2014 | Al-Ali et al. |
| 8,641,631 B2 | 2/2014 | Sierra et al. |
| 8,652,060 B2 | 2/2014 | Al-Ali |
| 8,663,107 B2 | 3/2014 | Kiani |
| 8,666,468 B1 | 3/2014 | Al-Ali |
| 8,667,967 B2 | 3/2014 | Al-Ali et al. |
| 8,668,643 B2 | 3/2014 | Kinast |
| 8,670,811 B2 | 3/2014 | O'Reilly |
| 8,670,814 B2 | 3/2014 | Diab et al. |
| 8,676,286 B2 | 3/2014 | Weber et al. |
| 8,682,407 B2 | 3/2014 | Al-Ali |
| RE44,823 E | 4/2014 | Parker |
| RE44,875 E | 4/2014 | Kiani et al. |
| 8,688,183 B2 | 4/2014 | Bruinsma et al. |
| 8,690,799 B2 | 4/2014 | Telfort et al. |
| 8,700,112 B2 | 4/2014 | Kiani |
| 8,702,627 B2 | 4/2014 | Telfort et al. |
| 8,706,179 B2 | 4/2014 | Parker |
| 8,712,494 B1 | 4/2014 | MacNeish, III et al. |
| 8,715,206 B2 | 5/2014 | Telfort et al. |
| 8,718,735 B2 | 5/2014 | Lamego et al. |
| 8,718,737 B2 | 5/2014 | Diab et al. |
| 8,718,738 B2 | 5/2014 | Blank et al. |
| 8,720,249 B2 | 5/2014 | Al-Ali |
| 8,721,541 B2 | 5/2014 | Al-Ali et al. |
| 8,721,542 B2 | 5/2014 | Al-Ali et al. |
| 8,723,677 B1 | 5/2014 | Kiani |
| 8,740,792 B1 | 6/2014 | Kiani et al. |
| 8,754,776 B2 | 6/2014 | Poeze et al. |
| 8,755,535 B2 | 6/2014 | Telfort et al. |
| 8,755,856 B2 | 6/2014 | Diab et al. |
| 8,755,872 B1 | 6/2014 | Marinow |
| 8,761,850 B2 | 6/2014 | Lamego |
| 8,764,671 B2 | 7/2014 | Kiani |
| 8,768,423 B2 | 7/2014 | Shakespeare et al. |
| 8,771,204 B2 | 7/2014 | Telfort et al. |
| 8,777,634 B2 | 7/2014 | Kiani et al. |
| 8,781,543 B2 | 7/2014 | Diab et al. |
| 8,781,544 B2 | 7/2014 | Al-Ali et al. |
| 8,781,549 B2 | 7/2014 | Al-Ali et al. |
| 8,788,003 B2 | 7/2014 | Schurman et al. |
| 8,790,268 B2 | 7/2014 | Al-Ali |
| 8,801,613 B2 | 8/2014 | Al-Ali et al. |
| 8,821,397 B2 | 9/2014 | Al-Ali et al. |
| 8,821,415 B2 | 9/2014 | Al-Ali et al. |
| 8,830,449 B1 | 9/2014 | Lamego et al. |
| 8,831,700 B2 | 9/2014 | Schurman et al. |
| 8,840,549 B2 | 9/2014 | Al-Ali et al. |
| 8,847,740 B2 | 9/2014 | Kiani et al. |
| 8,849,365 B2 | 9/2014 | Smith et al. |
| 8,852,094 B2 | 10/2014 | Al-Ali et al. |
| 8,852,994 B2 | 10/2014 | Wojtczuk et al. |
| 8,868,147 B2 | 10/2014 | Stippick et al. |
| 8,868,150 B2 | 10/2014 | Al-Ali et al. |
| 8,870,792 B2 | 10/2014 | Al-Ali et al. |
| 8,886,271 B2 | 11/2014 | Kiani et al. |
| 8,888,539 B2 | 11/2014 | Al-Ali et al. |
| 8,888,701 B2 | 11/2014 | LeBoeuf et al. |
| 8,888,708 B2 | 11/2014 | Diab et al. |
| 8,892,180 B2 | 11/2014 | Weber et al. |
| 8,897,847 B2 | 11/2014 | Al-Ali |
| 8,909,310 B2 | 12/2014 | Lamego et al. |
| 8,911,377 B2 | 12/2014 | Al-Ali |
| 8,912,909 B2 | 12/2014 | Al-Ali et al. |
| 8,920,317 B2 | 12/2014 | Al-Ali et al. |
| 8,921,699 B2 | 12/2014 | Al-Ali et al. |
| 8,922,382 B2 | 12/2014 | Al-Ali et al. |
| 8,929,964 B2 | 1/2015 | Al-Ali et al. |
| 8,929,967 B2 | 1/2015 | Mao et al. |
| 8,942,777 B2 | 1/2015 | Diab et al. |
| 8,948,834 B2 | 2/2015 | Diab et al. |
| 8,948,835 B2 | 2/2015 | Diab |
| 8,965,471 B2 | 2/2015 | Lamego |
| 8,983,564 B2 | 3/2015 | Al-Ali |
| 8,989,831 B2 | 3/2015 | Al-Ali et al. |
| 8,996,085 B2 | 3/2015 | Kiani et al. |
| 8,998,809 B2 | 4/2015 | Kiani |
| 9,005,129 B2 | 4/2015 | Venkatraman et al. |
| 9,028,429 B2 | 5/2015 | Telfort et al. |
| 9,037,207 B2 | 5/2015 | Al-Ali et al. |
| 9,060,721 B2 | 6/2015 | Reichgott et al. |
| 9,063,160 B2 | 6/2015 | Stamler et al. |
| 9,066,666 B2 | 6/2015 | Kiani |
| 9,066,680 B1 | 6/2015 | Al-Ali et al. |
| 9,072,474 B2 | 7/2015 | Al-Ali et al. |
| 9,078,560 B2 | 7/2015 | Schurman et al. |
| 9,084,569 B2 | 7/2015 | Weber et al. |

(56) References Cited

U.S. PATENT DOCUMENTS

| | | |
|---|---|---|
| 9,095,316 B2 | 8/2015 | Welch et al. |
| 9,106,038 B2 | 8/2015 | Telfort et al. |
| 9,107,625 B2 | 8/2015 | Telfort et al. |
| 9,107,626 B2 | 8/2015 | Al-Ali et al. |
| 9,113,831 B2 | 8/2015 | Al-Ali |
| 9,113,832 B2 | 8/2015 | Al-Ali |
| 9,119,595 B2 | 9/2015 | Lamego |
| 9,131,881 B2 | 9/2015 | Diab et al. |
| 9,131,882 B2 | 9/2015 | Al-Ali et al. |
| 9,131,883 B2 | 9/2015 | Al-Ali |
| 9,131,917 B2 | 9/2015 | Telfort et al. |
| 9,138,180 B1 | 9/2015 | Coverston et al. |
| 9,138,182 B2 | 9/2015 | Al-Ali et al. |
| 9,138,192 B2 | 9/2015 | Weber et al. |
| 9,142,117 B2 | 9/2015 | Muhsin et al. |
| 9,153,112 B1 | 10/2015 | Kiani et al. |
| 9,153,121 B2 | 10/2015 | Kiani et al. |
| 9,161,696 B2 | 10/2015 | Al-Ali et al. |
| 9,161,713 B2 | 10/2015 | Al-Ali et al. |
| 9,167,995 B2 | 10/2015 | Lamego et al. |
| 9,176,141 B2 | 11/2015 | Al-Ali et al. |
| 9,186,102 B2 | 11/2015 | Bruinsma et al. |
| 9,192,312 B2 | 11/2015 | Al-Ali |
| 9,192,329 B2 | 11/2015 | Al-Ali |
| 9,192,351 B1 | 11/2015 | Telfort et al. |
| 9,195,385 B2 | 11/2015 | Al-Ali et al. |
| 9,211,072 B2 | 12/2015 | Kiani |
| 9,211,095 B1 | 12/2015 | Al-Ali |
| 9,218,454 B2 | 12/2015 | Kiani et al. |
| 9,226,696 B2 | 1/2016 | Kiani |
| 9,241,662 B2 | 1/2016 | Al-Ali et al. |
| 9,245,668 B1 | 1/2016 | Vo et al. |
| 9,259,185 B2 | 2/2016 | Abdul-Hafiz et al. |
| 9,267,572 B2 | 2/2016 | Barker et al. |
| 9,277,880 B2 | 3/2016 | Poeze et al. |
| 9,289,167 B2 | 3/2016 | Diab et al. |
| 9,295,421 B2 | 3/2016 | Kiani et al. |
| 9,307,928 B1 | 4/2016 | Al-Ali et al. |
| 9,323,894 B2 | 4/2016 | Kiani |
| D755,392 S | 5/2016 | Hwang et al. |
| 9,326,712 B1 | 5/2016 | Kiani |
| 9,333,316 B2 | 5/2016 | Kiani |
| 9,339,220 B2 | 5/2016 | Lamego et al. |
| 9,341,565 B2 | 5/2016 | Lamego et al. |
| 9,351,673 B2 | 5/2016 | Diab et al. |
| 9,351,675 B2 | 5/2016 | Al-Ali et al. |
| 9,364,181 B2 | 6/2016 | Kiani et al. |
| 9,368,671 B2 | 6/2016 | Wojtczuk et al. |
| 9,370,325 B2 | 6/2016 | Al-Ali et al. |
| 9,370,326 B2 | 6/2016 | McHale et al. |
| 9,370,335 B2 | 6/2016 | Al-Ali et al. |
| 9,375,185 B2 | 6/2016 | Ali et al. |
| 9,386,953 B2 | 7/2016 | Al-Ali |
| 9,386,961 B2 | 7/2016 | Al-Ali et al. |
| 9,392,945 B2 | 7/2016 | Al-Ali et al. |
| 9,397,448 B2 | 7/2016 | Al-Ali et al. |
| 9,408,542 B1 | 8/2016 | Kinast et al. |
| 9,436,645 B2 | 9/2016 | Al-Ali et al. |
| 9,445,759 B1 | 9/2016 | Lamego et al. |
| 9,466,919 B2 | 10/2016 | Kiani et al. |
| 9,474,474 B2 | 10/2016 | Lamego et al. |
| 9,480,422 B2 | 11/2016 | Al-Ali |
| 9,480,435 B2 | 11/2016 | Olsen |
| 9,492,110 B2 | 11/2016 | Al-Ali et al. |
| 9,510,779 B2 | 12/2016 | Poeze et al. |
| 9,517,024 B2 | 12/2016 | Kiani et al. |
| 9,532,722 B2 | 1/2017 | Lamego et al. |
| 9,538,949 B2 | 1/2017 | Al-Ali et al. |
| 9,538,980 B2 | 1/2017 | Telfort et al. |
| 9,549,696 B2 | 1/2017 | Lamego et al. |
| 9,554,737 B2 | 1/2017 | Schurman et al. |
| 9,560,994 B2 | 2/2017 | McCutcheon et al. |
| 9,560,996 B2 | 2/2017 | Kiani |
| 9,560,998 B2 | 2/2017 | Al-Ali et al. |
| 9,566,019 B2 | 2/2017 | Al-Ali et al. |
| 9,579,039 B2 | 2/2017 | Jansen et al. |
| 9,622,692 B2 | 4/2017 | Lamego et al. |
| D788,312 S | 5/2017 | Al-Ali et al. |
| 9,649,054 B2 | 5/2017 | Lamego et al. |
| 9,697,928 B2 | 7/2017 | Al-Ali et al. |
| 9,717,458 B2 | 8/2017 | Lamego et al. |
| 9,723,997 B1 | 8/2017 | Lamego |
| 9,724,016 B1 | 8/2017 | Al-Ali et al. |
| 9,724,024 B2 | 8/2017 | Al-Ali |
| 9,724,025 B1 | 8/2017 | Kiani et al. |
| 9,749,232 B2 | 8/2017 | Sampath et al. |
| 9,750,442 B2 | 9/2017 | Olsen |
| 9,750,443 B2 | 9/2017 | Smith et al. |
| 9,750,461 B1 | 9/2017 | Telfort |
| 9,775,545 B2 | 10/2017 | Al-Ali et al. |
| 9,778,079 B1 | 10/2017 | Al-Ali et al. |
| 9,782,077 B2 | 10/2017 | Lamego et al. |
| 9,787,568 B2 | 10/2017 | Lamego et al. |
| 9,808,188 B1 | 11/2017 | Perea et al. |
| 9,839,379 B2 | 12/2017 | Al-Ali et al. |
| 9,839,381 B1 | 12/2017 | Weber et al. |
| 9,847,749 B2 | 12/2017 | Kiani et al. |
| 9,848,800 B1 | 12/2017 | Lee et al. |
| 9,848,807 B2 | 12/2017 | Lamego |
| 9,861,298 B2 | 1/2018 | Eckerbom et al. |
| 9,861,305 B1 | 1/2018 | Weber et al. |
| 9,877,650 B2 | 1/2018 | Muhsin et al. |
| 9,891,079 B2 | 2/2018 | Dalvi |
| 9,924,897 B1 | 3/2018 | Abdul-Hafiz |
| 9,936,917 B2 | 4/2018 | Poeze et al. |
| 9,952,095 B1 | 4/2018 | Hotelling et al. |
| 9,955,937 B2 | 5/2018 | Telfort |
| 9,965,946 B2 | 5/2018 | Al-Ali et al. |
| D820,865 S | 6/2018 | Muhsin et al. |
| 9,986,952 B2 | 6/2018 | Dalvi et al. |
| D822,215 S | 7/2018 | Al-Ali et al. |
| D822,216 S | 7/2018 | Barker et al. |
| 10,010,276 B2 | 7/2018 | Al-Ali et al. |
| 10,024,655 B2 | 7/2018 | Raguin et al. |
| 10,078,052 B2 | 9/2018 | Ness et al. |
| 10,086,138 B1 | 10/2018 | Novak, Jr. |
| 10,111,591 B2 | 10/2018 | Dyell et al. |
| D833,624 S | 11/2018 | DeJong et al. |
| 10,123,726 B2 | 11/2018 | Al-Ali et al. |
| 10,123,729 B2 | 11/2018 | Dyell et al. |
| D835,282 S | 12/2018 | Barker et al. |
| D835,283 S | 12/2018 | Barker et al. |
| D835,284 S | 12/2018 | Barker et al. |
| D835,285 S | 12/2018 | Barker et al. |
| 10,149,616 B2 | 12/2018 | Al-Ali et al. |
| 10,154,815 B2 | 12/2018 | Al-Ali et al. |
| 10,159,412 B2 | 12/2018 | Lamego et al. |
| 10,188,348 B2 | 1/2019 | Al-Ali et al. |
| RE47,218 E | 2/2019 | Al-Ali |
| RE47,244 E | 2/2019 | Kiani et al. |
| RE47,249 E | 2/2019 | Kiani et al. |
| 10,205,291 B2 | 2/2019 | Scruggs et al. |
| 10,219,746 B2 | 3/2019 | McHale et al. |
| 10,219,754 B1 | 3/2019 | Lamego |
| 10,226,187 B2 | 3/2019 | Al-Ali et al. |
| 10,231,657 B2 | 3/2019 | Al-Ali et al. |
| 10,231,670 B2 | 3/2019 | Blank et al. |
| RE47,353 E | 4/2019 | Kiani et al. |
| 10,247,670 B2 | 4/2019 | Ness et al. |
| 10,251,585 B2 | 4/2019 | Al-Ali et al. |
| 10,251,586 B2 | 4/2019 | Lamego |
| 10,279,247 B2 | 5/2019 | Kiani |
| 10,292,664 B2 | 5/2019 | Al-Ali |
| 10,299,720 B2 | 5/2019 | Brown et al. |
| 10,327,337 B2 | 6/2019 | Schmidt et al. |
| 10,327,683 B2 | 6/2019 | Smith et al. |
| 10,327,713 B2 | 6/2019 | Barker et al. |
| 10,332,630 B2 | 6/2019 | Al-Ali |
| 10,383,520 B2 | 8/2019 | Wojtczuk et al. |
| 10,383,527 B2 | 8/2019 | Al-Ali |
| 10,388,120 B2 | 8/2019 | Muhsin et al. |
| D864,120 S | 10/2019 | Forrest et al. |
| 10,441,181 B1 | 10/2019 | Telfort et al. |
| 10,441,196 B2 | 10/2019 | Eckerbom et al. |

(56) References Cited

U.S. PATENT DOCUMENTS

| | | |
|---|---|---|
| 10,448,844 B2 | 10/2019 | Al-Ali et al. |
| 10,448,871 B2 | 10/2019 | Al-Ali et al. |
| 10,456,038 B2 | 10/2019 | Lamego et al. |
| 10,463,340 B2 | 11/2019 | Telfort et al. |
| 10,471,159 B1 | 11/2019 | Lapotko et al. |
| 10,505,311 B2 | 12/2019 | Al-Ali et al. |
| 10,524,671 B2 | 1/2020 | Lamego |
| 10,524,738 B2 | 1/2020 | Olsen |
| 10,532,174 B2 | 1/2020 | Al-Ali |
| 10,537,285 B2 | 1/2020 | Shreim et al. |
| 10,542,903 B2 | 1/2020 | Al-Ali et al. |
| 10,555,678 B2 | 2/2020 | Dalvi et al. |
| 10,568,553 B2 | 2/2020 | O'Neil et al. |
| RE47,882 E | 3/2020 | Al-Ali |
| 10,575,779 B2 | 3/2020 | Poeze et al. |
| 10,608,817 B2 | 3/2020 | Haider et al. |
| D880,477 S | 4/2020 | Forrest et al. |
| 10,617,302 B2 | 4/2020 | Al-Ali et al. |
| 10,617,335 B2 | 4/2020 | Al-Ali et al. |
| 10,637,181 B2 | 4/2020 | Al-Ali et al. |
| D887,548 S | 6/2020 | Abdul-Hafiz et al. |
| D887,549 S | 6/2020 | Abdul-Hafiz et al. |
| 10,667,764 B2 | 6/2020 | Ahmed et al. |
| D890,708 S | 7/2020 | Forrest et al. |
| 10,721,785 B2 | 7/2020 | Al-Ali |
| 10,736,518 B2 | 8/2020 | Al-Ali et al. |
| 10,750,984 B2 | 8/2020 | Pauley et al. |
| D897,098 S | 9/2020 | Al-Ali |
| 10,779,098 B2 | 9/2020 | Iswanto et al. |
| 10,827,961 B1 | 11/2020 | Iyengar et al. |
| 10,828,007 B1 | 11/2020 | Telfort et al. |
| 10,832,818 B2 | 11/2020 | Muhsin et al. |
| 10,849,554 B2 | 12/2020 | Shreim et al. |
| 10,856,750 B2 | 12/2020 | Indorf |
| D906,970 S | 1/2021 | Forrest et al. |
| 10,918,281 B2 | 2/2021 | Al-Ali et al. |
| 10,932,705 B2 | 3/2021 | Muhsin et al. |
| 10,932,729 B2 | 3/2021 | Kiani et al. |
| 10,939,878 B2 | 3/2021 | Kiani et al. |
| 10,956,950 B2 | 3/2021 | Al-Ali et al. |
| D916,135 S | 4/2021 | Indorf et al. |
| D917,550 S | 4/2021 | Indorf et al. |
| D917,564 S | 4/2021 | Indorf et al. |
| D917,704 S | 4/2021 | Al-Ali et al. |
| 10,984,911 B2 | 4/2021 | Smith et al. |
| 10,987,066 B2 | 4/2021 | Chandran et al. |
| 10,991,135 B2 | 4/2021 | Al-Ali et al. |
| D919,094 S | 5/2021 | Al-Ali et al. |
| D919,100 S | 5/2021 | Al-Ali et al. |
| 11,006,867 B2 | 5/2021 | Al-Ali |
| D921,202 S | 6/2021 | Al-Ali et al. |
| 11,024,064 B2 | 6/2021 | Muhsin et al. |
| 11,026,604 B2 | 6/2021 | Chen et al. |
| D925,597 S | 7/2021 | Chandran et al. |
| D927,699 S | 8/2021 | Al-Ali et al. |
| 11,076,777 B2 | 8/2021 | Lee et al. |
| 11,114,188 B2 | 9/2021 | Poeze et al. |
| D933,232 S | 10/2021 | Al-Ali et al. |
| 11,145,408 B2 | 10/2021 | Sampath et al. |
| 11,147,518 B1 | 10/2021 | Al-Ali et al. |
| 11,185,262 B2 | 11/2021 | Al-Ali et al. |
| 11,191,484 B2 | 12/2021 | Kiani et al. |
| 2001/0009265 A1* | 7/2001 | Schulz .............. A61B 5/6838 250/227.14 |
| 2001/0034477 A1 | 10/2001 | Mansfield et al. |
| 2001/0039483 A1 | 11/2001 | Brand et al. |
| 2001/0044700 A1 | 11/2001 | Kobayashi et al. |
| 2001/0045532 A1 | 11/2001 | Schulz et al. |
| 2001/0056243 A1 | 12/2001 | Ohsaki et al. |
| 2002/0010401 A1 | 1/2002 | Bushmakin et al. |
| 2002/0021269 A1 | 2/2002 | Rast |
| 2002/0026107 A1 | 2/2002 | Kiani et al. |
| 2002/0035315 A1 | 3/2002 | Ali et al. |
| 2002/0035318 A1 | 3/2002 | Mannheimer et al. |
| 2002/0038078 A1 | 3/2002 | Ito |
| 2002/0038080 A1 | 3/2002 | Makarewicz et al. |
| 2002/0038081 A1 | 3/2002 | Fein et al. |
| 2002/0051290 A1 | 5/2002 | Hannington |
| 2002/0058864 A1 | 5/2002 | Mansfield et al. |
| 2002/0059047 A1 | 5/2002 | Haaland |
| 2002/0068858 A1 | 6/2002 | Braig et al. |
| 2002/0082488 A1 | 6/2002 | Al-Ali et al. |
| 2002/0095076 A1 | 7/2002 | Krausman et al. |
| 2002/0095077 A1 | 7/2002 | Swedlow et al. |
| 2002/0095078 A1 | 7/2002 | Mannheimer et al. |
| 2002/0111748 A1 | 8/2002 | Kobayashi et al. |
| 2002/0115919 A1 | 8/2002 | Al-Ali |
| 2002/0133080 A1 | 9/2002 | Apruzzese et al. |
| 2002/0154665 A1 | 10/2002 | Funabashi et al. |
| 2002/0156353 A1 | 10/2002 | Larson |
| 2002/0159002 A1 | 10/2002 | Chang |
| 2002/0161291 A1 | 10/2002 | Kiani et al. |
| 2002/0165440 A1 | 11/2002 | Mason et al. |
| 2002/0183819 A1 | 12/2002 | Struble |
| 2002/0188210 A1 | 12/2002 | Aizawa |
| 2002/0198442 A1 | 12/2002 | Rantala et al. |
| 2003/0013975 A1 | 1/2003 | Kiani |
| 2003/0018243 A1 | 1/2003 | Gerhardt et al. |
| 2003/0045784 A1 | 3/2003 | Palatnik et al. |
| 2003/0045785 A1 | 3/2003 | Diab et al. |
| 2003/0049232 A1 | 3/2003 | Page et al. |
| 2003/0088162 A1 | 5/2003 | Yamamoto et al. |
| 2003/0109775 A1 | 6/2003 | O'Neil et al. |
| 2003/0116769 A1 | 6/2003 | Song et al. |
| 2003/0117296 A1 | 6/2003 | Seely |
| 2003/0120160 A1 | 6/2003 | Yarita |
| 2003/0120164 A1 | 6/2003 | Nielsen et al. |
| 2003/0135099 A1 | 7/2003 | Al-Ali |
| 2003/0139657 A1 | 7/2003 | Solenberger |
| 2003/0144582 A1 | 7/2003 | Cohen et al. |
| 2003/0156288 A1 | 8/2003 | Barnum et al. |
| 2003/0160257 A1 | 8/2003 | Bader et al. |
| 2003/0195402 A1 | 10/2003 | Fein et al. |
| 2003/0212312 A1 | 11/2003 | Coffin, IV et al. |
| 2004/0006261 A1 | 1/2004 | Swedlow et al. |
| 2004/0033618 A1 | 2/2004 | Haass et al. |
| 2004/0034898 A1 | 2/2004 | Bruegl |
| 2004/0039271 A1 | 2/2004 | Blank et al. |
| 2004/0054291 A1 | 3/2004 | Schulz et al. |
| 2004/0059209 A1 | 3/2004 | Al-Ali et al. |
| 2004/0064259 A1 | 4/2004 | Haaland et al. |
| 2004/0081621 A1 | 4/2004 | Arndt et al. |
| 2004/0092805 A1 | 5/2004 | Yarita |
| 2004/0097797 A1 | 5/2004 | Porges et al. |
| 2004/0106163 A1 | 6/2004 | Workman, Jr. et al. |
| 2004/0133087 A1 | 7/2004 | Ali et al. |
| 2004/0138538 A1 | 7/2004 | Stetson |
| 2004/0138540 A1 | 7/2004 | Baker, Jr. et al. |
| 2004/0138568 A1 | 7/2004 | Lo et al. |
| 2004/0147822 A1 | 7/2004 | Al-Ali et al. |
| 2004/0147823 A1 | 7/2004 | Kiani et al. |
| 2004/0152957 A1 | 8/2004 | Stivoric et al. |
| 2004/0158132 A1 | 8/2004 | Zaleski |
| 2004/0158134 A1 | 8/2004 | Diab et al. |
| 2004/0158135 A1 | 8/2004 | Baker, Jr. et al. |
| 2004/0158162 A1 | 8/2004 | Narimatsu |
| 2004/0162472 A1 | 8/2004 | Berson et al. |
| 2004/0167382 A1 | 8/2004 | Gardner et al. |
| 2004/0171940 A1 | 9/2004 | Narimatsu |
| 2004/0176670 A1 | 9/2004 | Takamura et al. |
| 2004/0181134 A1 | 9/2004 | Baker, Jr. et al. |
| 2004/0199063 A1 | 10/2004 | O'Neil et al. |
| 2004/0204639 A1 | 10/2004 | Casciani et al. |
| 2004/0204868 A1 | 10/2004 | Maynard et al. |
| 2004/0220738 A1 | 11/2004 | Nissila |
| 2004/0229391 A1 | 11/2004 | Ohya et al. |
| 2004/0260191 A1 | 12/2004 | Stubbs et al. |
| 2004/0262046 A1 | 12/2004 | Simon et al. |
| 2004/0267103 A1 | 12/2004 | Li et al. |
| 2004/0267140 A1 | 12/2004 | Ito et al. |
| 2005/0011488 A1 | 1/2005 | Doucet |
| 2005/0043902 A1 | 2/2005 | Haaland et al. |
| 2005/0049469 A1 | 3/2005 | Aoyagi et al. |
| 2005/0054908 A1 | 3/2005 | Blank et al. |

(56) References Cited

U.S. PATENT DOCUMENTS

| | | |
|---|---|---|
| 2005/0055276 A1 | 3/2005 | Kiani et al. |
| 2005/0059869 A1 | 3/2005 | Scharf et al. |
| 2005/0070773 A1 | 3/2005 | Chin et al. |
| 2005/0070775 A1 | 3/2005 | Chin et al. |
| 2005/0075546 A1 | 4/2005 | Samsoondar et al. |
| 2005/0085704 A1 | 4/2005 | Schulz et al. |
| 2005/0085735 A1 | 4/2005 | Baker et al. |
| 2005/0115561 A1 | 6/2005 | Stahmann et al. |
| 2005/0124871 A1 | 6/2005 | Baker et al. |
| 2005/0143634 A1 | 6/2005 | Baker et al. |
| 2005/0143943 A1 | 6/2005 | Brown |
| 2005/0148834 A1 | 7/2005 | Hull et al. |
| 2005/0184895 A1 | 8/2005 | Petersen et al. |
| 2005/0187446 A1 | 8/2005 | Nordstrom et al. |
| 2005/0187447 A1 | 8/2005 | Chew et al. |
| 2005/0187448 A1 | 8/2005 | Petersen et al. |
| 2005/0187449 A1 | 8/2005 | Chew et al. |
| 2005/0187450 A1 | 8/2005 | Chew et al. |
| 2005/0187452 A1 | 8/2005 | Petersen et al. |
| 2005/0187453 A1 | 8/2005 | Petersen et al. |
| 2005/0197549 A1 | 9/2005 | Baker, Jr. |
| 2005/0197555 A1 | 9/2005 | Mouradian et al. |
| 2005/0197579 A1 | 9/2005 | Baker, Jr. |
| 2005/0197793 A1 | 9/2005 | Baker, Jr. |
| 2005/0203357 A1 | 9/2005 | Debreczeny et al. |
| 2005/0207943 A1 | 9/2005 | Puzey |
| 2005/0209515 A1 | 9/2005 | Hockersmith et al. |
| 2005/0228253 A1 | 10/2005 | Debreczeny |
| 2005/0234317 A1 | 10/2005 | Kiani |
| 2005/0250997 A1 | 11/2005 | Takedo et al. |
| 2005/0261673 A1 | 11/2005 | Bonner et al. |
| 2005/0276164 A1 | 12/2005 | Amron |
| 2005/0277819 A1 | 12/2005 | Kiani et al. |
| 2006/0030764 A1 | 2/2006 | Porges et al. |
| 2006/0073719 A1 | 4/2006 | Kiani |
| 2006/0189871 A1 | 8/2006 | Al-Ali et al. |
| 2006/0210120 A1 | 9/2006 | Rowe et al. |
| 2006/0211922 A1 | 9/2006 | Al-Ali et al. |
| 2006/0211923 A1 | 9/2006 | Al-Ali et al. |
| 2006/0211924 A1 | 9/2006 | Dalke et al. |
| 2006/0211925 A1 | 9/2006 | Lamego et al. |
| 2006/0211932 A1 | 9/2006 | Al-Ali et al. |
| 2006/0226992 A1 | 10/2006 | Al-Ali et al. |
| 2006/0229509 A1 | 10/2006 | Al-Ali et al. |
| 2006/0238358 A1 | 10/2006 | Al-Ali et al. |
| 2006/0241363 A1 | 10/2006 | Al-Ali et al. |
| 2006/0264718 A1 | 11/2006 | Ruchti et al. |
| 2007/0073116 A1 | 3/2007 | Kiani et al. |
| 2007/0078311 A1 | 4/2007 | Al-Ali et al. |
| 2007/0093701 A1 | 4/2007 | Myers |
| 2007/0093786 A1 | 4/2007 | Goldsmith et al. |
| 2007/0145255 A1 | 6/2007 | Nishikawa et al. |
| 2007/0149864 A1 | 6/2007 | Laakkonen |
| 2007/0129616 A1 | 7/2007 | Rantala |
| 2007/0180140 A1 | 8/2007 | Welch et al. |
| 2007/0185397 A1 | 8/2007 | Govari et al. |
| 2007/0244377 A1 | 10/2007 | Cozad et al. |
| 2007/0282478 A1 | 12/2007 | Al-Ali et al. |
| 2008/0030468 A1 | 2/2008 | Ali et al. |
| 2008/0064965 A1 | 3/2008 | Jay et al. |
| 2008/0094228 A1 | 4/2008 | Welch et al. |
| 2008/0122796 A1 | 5/2008 | Jobs et al. |
| 2008/0194932 A1 | 8/2008 | Ayers et al. |
| 2008/0200783 A9 | 8/2008 | Blank et al. |
| 2008/0221418 A1 | 9/2008 | Al-Ali et al. |
| 2008/0242958 A1 | 10/2008 | Al-Ali et al. |
| 2008/0281174 A1 | 11/2008 | Dietiker |
| 2009/0036759 A1 | 2/2009 | Ault et al. |
| 2009/0093687 A1 | 4/2009 | Telfort et al. |
| 2009/0095926 A1 | 4/2009 | MacNeish, III |
| 2009/0163775 A1 | 6/2009 | Barrett et al. |
| 2009/0247849 A1 | 10/2009 | McCutcheon et al. |
| 2009/0247924 A1 | 10/2009 | Lamego et al. |
| 2009/0247984 A1 | 10/2009 | Lamego et al. |
| 2009/0275813 A1 | 11/2009 | Davis |
| 2009/0275844 A1 | 11/2009 | Al-Ali |
| 2009/0299157 A1 | 12/2009 | Telfort et al. |
| 2010/0004518 A1 | 1/2010 | Vo et al. |
| 2010/0022859 A1 | 1/2010 | Al-Ali et al. |
| 2010/0030040 A1 | 2/2010 | Poeze et al. |
| 2010/0099964 A1 | 4/2010 | O'Reilly et al. |
| 2010/0234718 A1 | 9/2010 | Sampath et al. |
| 2010/0261979 A1 | 10/2010 | Al-Ali et al. |
| 2010/0270257 A1 | 10/2010 | Wachman et al. |
| 2010/0317936 A1 | 12/2010 | Al-Ali et al. |
| 2011/0001605 A1 | 1/2011 | Kiani et al. |
| 2011/0003665 A1 | 1/2011 | Burton et al. |
| 2011/0009719 A1 | 1/2011 | Al-Ali et al. |
| 2011/0028806 A1 | 2/2011 | Merritt et al. |
| 2011/0028809 A1 | 2/2011 | Goodman |
| 2011/0040197 A1 | 2/2011 | Welch et al. |
| 2011/0082711 A1 | 4/2011 | Poeze et al. |
| 2011/0087081 A1 | 4/2011 | Kiani et al. |
| 2011/0105854 A1 | 5/2011 | Kiani et al. |
| 2011/0118561 A1 | 5/2011 | Tari et al. |
| 2011/0125060 A1 | 5/2011 | Telfort et al. |
| 2011/0137297 A1 | 6/2011 | Kiani et al. |
| 2011/0172498 A1 | 7/2011 | Olsen et al. |
| 2011/0172967 A1 | 7/2011 | Al-Ali et al. |
| 2011/0208015 A1 | 8/2011 | Welch et al. |
| 2011/0209915 A1 | 9/2011 | Telfort et al. |
| 2011/0213212 A1 | 9/2011 | Al-Ali |
| 2011/0230733 A1 | 9/2011 | Al-Ali |
| 2011/0237911 A1 | 9/2011 | Lamego et al. |
| 2011/0237914 A1 | 9/2011 | Lamego et al. |
| 2011/0237969 A1 | 9/2011 | Eckerbom et al. |
| 2011/0288383 A1 | 11/2011 | Diab |
| 2011/0301444 A1 | 12/2011 | Al-Ali |
| 2012/0041316 A1 | 2/2012 | Al Ali et al. |
| 2012/0046530 A1 | 2/2012 | Al-Ali et al. |
| 2012/0046557 A1 | 2/2012 | Kiani |
| 2012/0059267 A1 | 3/2012 | Lamego et al. |
| 2012/0078069 A1 | 3/2012 | Melker |
| 2012/0088984 A1 | 4/2012 | Al-Ali et al. |
| 2012/0116175 A1 | 5/2012 | Al-Ali et al. |
| 2012/0123231 A1 | 5/2012 | O'Reilly |
| 2012/0161970 A1 | 6/2012 | Al-Ali et al. |
| 2012/0165629 A1 | 6/2012 | Merritt et al. |
| 2012/0179006 A1 | 7/2012 | Jansen et al. |
| 2012/0209082 A1 | 8/2012 | Al-Ali |
| 2012/0209084 A1 | 8/2012 | Olsen et al. |
| 2012/0226117 A1 | 9/2012 | Lamego et al. |
| 2012/0227739 A1 | 9/2012 | Kiani |
| 2012/0232359 A1 | 9/2012 | Al-Ali et al. |
| 2012/0232363 A1 | 9/2012 | Al-Ali et al. |
| 2012/0265039 A1 | 10/2012 | Kiani |
| 2012/0283524 A1 | 11/2012 | Kiani et al. |
| 2012/0286955 A1 | 11/2012 | Welch et al. |
| 2012/0296178 A1 | 11/2012 | Lamego et al. |
| 2012/0319816 A1 | 12/2012 | Al-Ali |
| 2012/0330112 A1 | 12/2012 | Lamego et al. |
| 2013/0006076 A1 | 1/2013 | McHale et al. |
| 2013/0023775 A1 | 1/2013 | Lamego et al. |
| 2013/0041591 A1 | 2/2013 | Lamego |
| 2013/0045685 A1 | 2/2013 | Kiani |
| 2013/0046204 A1 | 2/2013 | Lamego et al. |
| 2013/0060108 A1 | 3/2013 | Schurman et al. |
| 2013/0060147 A1 | 3/2013 | Welch et al. |
| 2013/0079610 A1 | 3/2013 | Al-Ali |
| 2013/0096405 A1 | 4/2013 | Garfio |
| 2013/0096936 A1 | 4/2013 | Sampath et al. |
| 2013/0109935 A1 | 5/2013 | Al-Ali et al. |
| 2013/0162433 A1 | 6/2013 | Muhsin et al. |
| 2013/0172701 A1 | 7/2013 | Smith et al. |
| 2013/0178749 A1 | 7/2013 | Lamego |
| 2013/0190581 A1 | 7/2013 | Al-Ali et al. |
| 2013/0197328 A1 | 8/2013 | Diab et al. |
| 2013/0211214 A1 | 8/2013 | Olsen |
| 2013/0243021 A1 | 9/2013 | Siskavich |
| 2013/0253334 A1 | 9/2013 | Al-Ali et al. |
| 2013/0262730 A1 | 10/2013 | Al-Ali et al. |
| 2013/0267804 A1 | 10/2013 | Al-Ali |
| 2013/0274571 A1 | 10/2013 | Diab et al. |
| 2013/0274572 A1 | 10/2013 | Al-Ali et al. |

(56) References Cited

U.S. PATENT DOCUMENTS

| | | |
|---|---|---|
| 2013/0296672 A1 | 11/2013 | O'Neil et al. |
| 2013/0296713 A1 | 11/2013 | Al-Ali et al. |
| 2013/0317327 A1 | 11/2013 | Al-Ali et al. |
| 2013/0317370 A1 | 11/2013 | Dalvi et al. |
| 2013/0324808 A1 | 12/2013 | Al-Ali et al. |
| 2013/0324817 A1 | 12/2013 | Diab |
| 2013/0331660 A1 | 12/2013 | Al-Ali et al. |
| 2013/0331670 A1 | 12/2013 | Kiani |
| 2013/0338461 A1 | 12/2013 | Lamego et al. |
| 2013/0345921 A1 | 12/2013 | Al-Ali et al. |
| 2014/0012100 A1 | 1/2014 | Al-Ali et al. |
| 2014/0025306 A1 | 1/2014 | Weber et al. |
| 2014/0031650 A1 | 1/2014 | Weber et al. |
| 2014/0034353 A1 | 2/2014 | Al-Ali et al. |
| 2014/0051952 A1 | 2/2014 | Reichgott et al. |
| 2014/0051953 A1 | 2/2014 | Lamego et al. |
| 2014/0051954 A1 | 2/2014 | Al-Ali et al. |
| 2014/0058230 A1 | 2/2014 | Abdul-Hafiz et al. |
| 2014/0066783 A1 | 3/2014 | Kiani et al. |
| 2014/0073167 A1 | 3/2014 | Al-Ali et al. |
| 2014/0077956 A1 | 3/2014 | Sampath et al. |
| 2014/0081097 A1 | 3/2014 | Al-Ali et al. |
| 2014/0081100 A1 | 3/2014 | Muhsin et al. |
| 2014/0081175 A1 | 3/2014 | Telfort |
| 2014/0094667 A1 | 4/2014 | Schurman et al. |
| 2014/0100434 A1 | 4/2014 | Diab et al. |
| 2014/0114199 A1 | 4/2014 | Lamego et al. |
| 2014/0120564 A1 | 5/2014 | Workman et al. |
| 2014/0121482 A1 | 5/2014 | Merritt et al. |
| 2014/0121483 A1 | 5/2014 | Kiani |
| 2014/0125495 A1 | 5/2014 | Al-Ali |
| 2014/0127137 A1 | 5/2014 | Bellott et al. |
| 2014/0128696 A1 | 5/2014 | Al-Ali |
| 2014/0128699 A1 | 5/2014 | Al-Ali et al. |
| 2014/0129702 A1 | 5/2014 | Lamego et al. |
| 2014/0135588 A1 | 5/2014 | Al-Ali et al. |
| 2014/0142399 A1 | 5/2014 | Al-Ali et al. |
| 2014/0142401 A1 | 5/2014 | Al-Ali et al. |
| 2014/0142402 A1 | 5/2014 | Al-Ali et al. |
| 2014/0155712 A1 | 6/2014 | Lamego et al. |
| 2014/0163344 A1 | 6/2014 | Al-Ali |
| 2014/0163402 A1 | 6/2014 | Lamego et al. |
| 2014/0166076 A1 | 6/2014 | Kiani et al. |
| 2014/0171763 A1 | 6/2014 | Diab |
| 2014/0180038 A1 | 6/2014 | Kiani |
| 2014/0180154 A1 | 6/2014 | Sierra et al. |
| 2014/0180160 A1 | 6/2014 | Brown et al. |
| 2014/0187973 A1 | 7/2014 | Brown et al. |
| 2014/0194709 A1 | 7/2014 | Al-Ali et al. |
| 2014/0194711 A1 | 7/2014 | Al-Ali |
| 2014/0194766 A1 | 7/2014 | Al-Ali et al. |
| 2014/0200420 A1 | 7/2014 | Al-Ali |
| 2014/0200422 A1 | 7/2014 | Weber et al. |
| 2014/0206963 A1 | 7/2014 | Al-Ali |
| 2014/0213864 A1 | 7/2014 | Abdul-Hafiz et al. |
| 2014/0243627 A1 | 8/2014 | Diab et al. |
| 2014/0266790 A1 | 9/2014 | Al-Ali et al. |
| 2014/0275808 A1 | 9/2014 | Poeze et al. |
| 2014/0275835 A1 | 9/2014 | Lamego et al. |
| 2014/0275871 A1 | 9/2014 | Lamego et al. |
| 2014/0275872 A1 | 9/2014 | Merritt et al. |
| 2014/0275881 A1 | 9/2014 | Lamego et al. |
| 2014/0276115 A1 | 9/2014 | Dalvi et al. |
| 2014/0288400 A1 | 9/2014 | Diab et al. |
| 2014/0296664 A1 | 10/2014 | Bruinsma et al. |
| 2014/0303520 A1 | 10/2014 | Telfort et al. |
| 2014/0309506 A1 | 10/2014 | Lamego et al. |
| 2014/0309559 A1 | 10/2014 | Telfort et al. |
| 2014/0316217 A1 | 10/2014 | Purdon et al. |
| 2014/0316218 A1 | 10/2014 | Purdon et al. |
| 2014/0316228 A1 | 10/2014 | Blank et al. |
| 2014/0323825 A1 | 10/2014 | Al-Ali et al. |
| 2014/0323897 A1 | 10/2014 | Brown et al. |
| 2014/0323898 A1 | 10/2014 | Purdon et al. |
| 2014/0330092 A1 | 11/2014 | Al-Ali et al. |
| 2014/0330098 A1 | 11/2014 | Merritt et al. |
| 2014/0330099 A1 | 11/2014 | Al-Ali et al. |
| 2014/0333440 A1 | 11/2014 | Kiani |
| 2014/0336481 A1 | 11/2014 | Shakespeare et al. |
| 2014/0343436 A1 | 11/2014 | Kiani |
| 2014/0357966 A1 | 12/2014 | Al-Ali et al. |
| 2014/0371548 A1 | 12/2014 | Al-Ali et al. |
| 2014/0371632 A1 | 12/2014 | Al-Ali et al. |
| 2014/0378784 A1 | 12/2014 | Kiani et al. |
| 2015/0005600 A1 | 1/2015 | Blank et al. |
| 2015/0011907 A1 | 1/2015 | Purdon et al. |
| 2015/0012231 A1 | 1/2015 | Poeze et al. |
| 2015/0018650 A1 | 1/2015 | Al-Ali et al. |
| 2015/0025406 A1 | 1/2015 | Al-Ali |
| 2015/0032029 A1 | 1/2015 | Al-Ali et al. |
| 2015/0038859 A1 | 2/2015 | Dalvi et al. |
| 2015/0045637 A1 | 2/2015 | Dalvi |
| 2015/0045685 A1 | 2/2015 | Al-Ali et al. |
| 2015/0051462 A1 | 2/2015 | Olsen |
| 2015/0073241 A1 | 3/2015 | Lamego |
| 2015/0080754 A1 | 3/2015 | Purdon et al. |
| 2015/0087936 A1 | 3/2015 | Al-Ali et al. |
| 2015/0094546 A1 | 4/2015 | Al-Ali |
| 2015/0097701 A1 | 4/2015 | Muhsin et al. |
| 2015/0099324 A1 | 4/2015 | Wojtczuk et al. |
| 2015/0099950 A1 | 4/2015 | Al-Ali et al. |
| 2015/0099951 A1 | 4/2015 | Al-Ali et al. |
| 2015/0099955 A1 | 4/2015 | Al-Ali et al. |
| 2015/0101844 A1 | 4/2015 | Al-Ali et al. |
| 2015/0106121 A1 | 4/2015 | Muhsin et al. |
| 2015/0112151 A1 | 4/2015 | Muhsin et al. |
| 2015/0116076 A1 | 4/2015 | Al-Ali et al. |
| 2015/0126830 A1 | 5/2015 | Schurman et al. |
| 2015/0133755 A1 | 5/2015 | Smith et al. |
| 2015/0140863 A1 | 5/2015 | Al-Ali et al. |
| 2015/0141781 A1 | 5/2015 | Weber et al. |
| 2015/0165312 A1 | 6/2015 | Kiani |
| 2015/0196237 A1 | 7/2015 | Lamego |
| 2015/0201874 A1 | 7/2015 | Diab |
| 2015/0208966 A1 | 7/2015 | Al-Ali |
| 2015/0216459 A1 | 8/2015 | Al-Ali et al. |
| 2015/0230755 A1 | 8/2015 | Al-Ali et al. |
| 2015/0238722 A1 | 8/2015 | Al-Ali |
| 2015/0245773 A1 | 9/2015 | Lamego et al. |
| 2015/0245793 A1 | 9/2015 | Al-Ali et al. |
| 2015/0245794 A1 | 9/2015 | Al-Ali |
| 2015/0257689 A1 | 9/2015 | Al-Ali et al. |
| 2015/0272514 A1 | 10/2015 | Kiani et al. |
| 2015/0351697 A1 | 12/2015 | Weber et al. |
| 2015/0351704 A1 | 12/2015 | Kiani et al. |
| 2015/0359429 A1 | 12/2015 | Al-Ali et al. |
| 2015/0366472 A1 | 12/2015 | Kiani |
| 2015/0366507 A1 | 12/2015 | Blank et al. |
| 2015/0374298 A1 | 12/2015 | Al-Ali et al. |
| 2015/0380875 A1 | 12/2015 | Coverston et al. |
| 2016/0000362 A1 | 1/2016 | Diab et al. |
| 2016/0007930 A1 | 1/2016 | Weber et al. |
| 2016/0029932 A1 | 2/2016 | Al-Ali |
| 2016/0029933 A1 | 2/2016 | Al-Ali et al. |
| 2016/0045118 A1 | 2/2016 | Kiani |
| 2016/0051205 A1 | 2/2016 | Al-Ali et al. |
| 2016/0058338 A1 | 3/2016 | Schurman et al. |
| 2016/0058347 A1 | 3/2016 | Reichgott et al. |
| 2016/0066823 A1 | 3/2016 | Al-Ali et al. |
| 2016/0066824 A1 | 3/2016 | Al-Ali et al. |
| 2016/0066879 A1 | 3/2016 | Telfort et al. |
| 2016/0072429 A1 | 3/2016 | Kiani et al. |
| 2016/0073967 A1 | 3/2016 | Lamego et al. |
| 2016/0081552 A1 | 3/2016 | Wojtczuk et al. |
| 2016/0095543 A1 | 4/2016 | Telfort et al. |
| 2016/0095548 A1 | 4/2016 | Al-Ali et al. |
| 2016/0103598 A1 | 4/2016 | Al-Ali et al. |
| 2016/0113527 A1 | 4/2016 | Al-Ali |
| 2016/0143548 A1 | 5/2016 | Al-Ali |
| 2016/0166182 A1 | 6/2016 | Al-Ali et al. |
| 2016/0166183 A1 | 6/2016 | Poeze et al. |
| 2016/0166188 A1 | 6/2016 | Bruinsma et al. |
| 2016/0166210 A1 | 6/2016 | Al-Ali |
| 2016/0192869 A1 | 7/2016 | Kiani et al. |

(56) References Cited

U.S. PATENT DOCUMENTS

| | | |
|---|---|---|
| 2016/0196388 A1 | 7/2016 | Lamego |
| 2016/0197436 A1 | 7/2016 | Barker et al. |
| 2016/0213281 A1 | 7/2016 | Eckerbom et al. |
| 2016/0228043 A1 | 8/2016 | O'Neil et al. |
| 2016/0233632 A1 | 8/2016 | Scruggs et al. |
| 2016/0234944 A1 | 8/2016 | Schmidt et al. |
| 2016/0270735 A1 | 9/2016 | Diab et al. |
| 2016/0283665 A1 | 9/2016 | Sampath et al. |
| 2016/0287090 A1 | 10/2016 | Al-Ali et al. |
| 2016/0287786 A1 | 10/2016 | Kiani |
| 2016/0296169 A1 | 10/2016 | McHale et al. |
| 2016/0310052 A1 | 10/2016 | Al-Ali et al. |
| 2016/0314260 A1 | 10/2016 | Kiani |
| 2016/0324486 A1 | 11/2016 | Al-Ali et al. |
| 2016/0324488 A1 | 11/2016 | Olsen |
| 2016/0327984 A1 | 11/2016 | Al-Ali et al. |
| 2016/0328528 A1 | 11/2016 | Al-Ali et al. |
| 2016/0331332 A1 | 11/2016 | Al-Ali |
| 2016/0367173 A1 | 12/2016 | Dalvi et al. |
| 2017/0007134 A1 | 1/2017 | Al-Ali et al. |
| 2017/0007190 A1 | 1/2017 | Al-Ali et al. |
| 2017/0007198 A1 | 1/2017 | Al-Ali et al. |
| 2017/0014084 A1 | 1/2017 | Al-Ali et al. |
| 2017/0021099 A1 | 1/2017 | Al-Ali et al. |
| 2017/0024748 A1 | 1/2017 | Haider |
| 2017/0027456 A1 | 2/2017 | Kinast et al. |
| 2017/0042488 A1 | 2/2017 | Muhsin |
| 2017/0055896 A1 | 3/2017 | Al-Ali |
| 2017/0173632 A1 | 6/2017 | Al-Ali |
| 2017/0251974 A1 | 9/2017 | Shreim et al. |
| 2017/0311891 A1 | 11/2017 | Kiani et al. |
| 2018/0070867 A1 | 3/2018 | Smith et al. |
| 2018/0103874 A1 | 4/2018 | Lee et al. |
| 2018/0132770 A1 | 5/2018 | Lamego |
| 2018/0199871 A1 | 7/2018 | Pauley et al. |
| 2018/0213583 A1 | 7/2018 | Al-Ali |
| 2018/0242926 A1 | 8/2018 | Muhsin et al. |
| 2018/0247353 A1 | 8/2018 | Al-Ali et al. |
| 2018/0247712 A1 | 8/2018 | Muhsin et al. |
| 2018/0256087 A1 | 9/2018 | Al-Ali et al. |
| 2018/0289325 A1 | 10/2018 | Poeze et al. |
| 2018/0296161 A1 | 10/2018 | Shreim et al. |
| 2018/0300919 A1 | 10/2018 | Muhsin et al. |
| 2018/0310822 A1 | 11/2018 | Indorf et al. |
| 2018/0310823 A1 | 11/2018 | Al-Ali et al. |
| 2018/0317826 A1 | 11/2018 | Muhsin et al. |
| 2019/0015023 A1 | 1/2019 | Monfre |
| 2019/0117070 A1 | 4/2019 | Muhsin et al. |
| 2019/0200941 A1 | 7/2019 | Chandran et al. |
| 2019/0239787 A1 | 8/2019 | Pauley et al. |
| 2019/0320906 A1 | 10/2019 | Olsen |
| 2019/0320988 A1 | 10/2019 | Ahmed et al. |
| 2019/0350497 A1 | 11/2019 | Al-Ali et al. |
| 2019/0374139 A1 | 12/2019 | Kiani et al. |
| 2019/0374173 A1 | 12/2019 | Kiani et al. |
| 2019/0374713 A1 | 12/2019 | Kiani et al. |
| 2020/0021930 A1 | 1/2020 | Iswanto et al. |
| 2020/0060869 A1 | 2/2020 | Telfort et al. |
| 2020/0111552 A1 | 4/2020 | Ahmed |
| 2020/0113435 A1 | 4/2020 | Muhsin |
| 2020/0113488 A1 | 4/2020 | Al-Ali et al. |
| 2020/0113496 A1 | 4/2020 | Scruggs et al. |
| 2020/0113497 A1 | 4/2020 | Triman et al. |
| 2020/0113520 A1 | 4/2020 | Abdul-Hafiz et al. |
| 2020/0138288 A1 | 5/2020 | Al-Ali et al. |
| 2020/0138368 A1 | 5/2020 | Kiani et al. |
| 2020/0163597 A1 | 5/2020 | Dalvi et al. |
| 2020/0196877 A1 | 6/2020 | Vo et al. |
| 2020/0253474 A1 | 8/2020 | Muhsin et al. |
| 2020/0253544 A1 | 8/2020 | Belur Nagaraj et al. |
| 2020/0275841 A1 | 9/2020 | Telfort et al. |
| 2020/0288983 A1 | 9/2020 | Telfort et al. |
| 2020/0321793 A1 | 10/2020 | Al-Ali et al. |
| 2020/0329983 A1 | 10/2020 | Al-Ali et al. |
| 2020/0329984 A1 | 10/2020 | Al-Ali et al. |
| 2020/0329993 A1 | 10/2020 | Al-Ali et al. |
| 2020/0330037 A1 | 10/2020 | Al-Ali et al. |
| 2021/0022628 A1 | 1/2021 | Telfort et al. |
| 2021/0104173 A1 | 4/2021 | Pauley et al. |
| 2021/0113121 A1 | 4/2021 | Diab et al. |
| 2021/0117525 A1 | 4/2021 | Kiani et al. |
| 2021/0118581 A1 | 4/2021 | Kiani et al. |
| 2021/0121582 A1 | 4/2021 | Krishnamani et al. |
| 2021/0161465 A1 | 6/2021 | Barker et al. |
| 2021/0236729 A1 | 8/2021 | Kiani et al. |
| 2021/0256267 A1 | 8/2021 | Ranasinghe et al. |
| 2021/0256835 A1 | 8/2021 | Ranasinghe et al. |
| 2021/0275101 A1 | 9/2021 | Vo et al. |
| 2021/0290060 A1 | 9/2021 | Ahmed |
| 2021/0290072 A1 | 9/2021 | Forrest |
| 2021/0290080 A1 | 9/2021 | Ahmed |
| 2021/0290120 A1 | 9/2021 | Al-Ali |
| 2021/0290177 A1 | 9/2021 | Novak, Jr. |
| 2021/0290184 A1 | 9/2021 | Ahmed |
| 2021/0296008 A1 | 9/2021 | Novak, Jr. |
| 2021/0330228 A1 | 10/2021 | Olsen et al. |
| 2021/0386382 A1 | 12/2021 | Olsen et al. |
| 2021/0402110 A1 | 12/2021 | Pauley et al. |
| 2022/0053892 A1 | 2/2022 | Al-Ali et al. |

FOREIGN PATENT DOCUMENTS

| | | |
|---|---|---|
| EP | 0 231 379 | 8/1987 |
| EP | 0 419 223 | 3/1991 |
| EP | 0 569 670 | 2/1993 |
| EP | 0 675 540 | 10/1995 |
| EP | 0 675 541 | 10/1995 |
| EP | 0 469 395 | 2/1996 |
| EP | 0665727 | 1/1997 |
| EP | 0760223 | 3/1997 |
| EP | 0 417 447 | 10/1997 |
| EP | 0 606 356 | 6/1998 |
| EP | 0 734 221 | 7/1998 |
| EP | 0 529 412 | 11/1998 |
| EP | 1 080 683 | 3/2001 |
| EP | 1 207 536 | 5/2002 |
| EP | 1 895 892 | 5/2010 |
| EP | 2 476 369 | 7/2012 |
| EP | 2 139 383 | 2/2013 |
| EP | 2305 104 | 10/2018 |
| JP | 61-28172 | 2/1986 |
| JP | 62-000324 | 1/1987 |
| JP | 63-275327 | 11/1988 |
| JP | 64-500495 | 2/1989 |
| JP | 2-126829 | 5/1990 |
| JP | 2-145457 | 12/1990 |
| JP | 03-252604 | 11/1991 |
| JP | 05-200017 | 8/1993 |
| JP | 05-207993 | 8/1993 |
| JP | H06-178776 | 6/1994 |
| JP | 06-505903 | 7/1994 |
| JP | 06-237013 | 8/1994 |
| JP | H07-391 | 1/1995 |
| JP | H07-171089 | 7/1995 |
| JP | H07-171090 | 7/1995 |
| JP | 07-281618 | 10/1995 |
| JP | 07-325546 | 12/1995 |
| JP | 09-108203 | 4/1997 |
| JP | 09-503402 | 4/1997 |
| JP | 09-192120 | 7/1997 |
| JP | 09-308623 | 12/1997 |
| JP | 10-500026 | 1/1998 |
| JP | 10-216112 | 8/1998 |
| JP | 10-509352 | 9/1998 |
| JP | 10-269344 A | 10/1998 |
| JP | 10-295676 | 11/1998 |
| JP | 10-305026 | 11/1998 |
| JP | 11-037932 | 2/1999 |
| JP | 11-163412 | 6/1999 |
| JP | 11-164826 | 6/1999 |
| JP | 11-506834 | 6/1999 |
| JP | 11-183377 | 7/1999 |
| JP | 2011-508691 | 7/1999 |
| JP | H11-197127 | 7/1999 |

(56) References Cited

FOREIGN PATENT DOCUMENTS

| | | |
|---|---|---|
| JP | 2000-116625 | 4/2000 |
| JP | 2000-199880 | 7/2000 |
| JP | 2001-504256 | 3/2001 |
| JP | 2002-150821 | 5/2002 |
| JP | 2002-516689 | 6/2002 |
| JP | 2002-228579 | 8/2002 |
| JP | 2002-525151 | 8/2002 |
| JP | 2002-315739 | 10/2002 |
| JP | 2002-352609 | 12/2002 |
| JP | 2003-507718 | 2/2003 |
| JP | 2003-084108 | 3/2003 |
| JP | 2003-521985 | 7/2003 |
| JP | 2004-070179 | 3/2004 |
| JP | 2004-510467 | 4/2004 |
| JP | 2004-173866 | 6/2004 |
| JP | 2004-226277 | 8/2004 |
| JP | 2004-296736 | 10/2004 |
| JP | 2004-532526 | 10/2004 |
| JP | 2004-327760 | 11/2004 |
| JP | 2005-501589 | 1/2005 |
| JP | 2005-253478 | 9/2005 |
| JP | 2005-270543 | 10/2005 |
| JP | 2006-296564 | 11/2006 |
| JP | 2008-505706 | 2/2008 |
| JP | 4879913 | 12/2011 |
| JP | 2012-110746 | 6/2012 |
| JP | 2012-130756 | 7/2012 |
| JP | 5096174 | 9/2012 |
| JP | 5166619 | 3/2013 |
| JP | 5328159 | 8/2013 |
| JP | 5456976 | 1/2014 |
| WO | WO 88/001150 | 2/1988 |
| WO | WO 88/002020 | 2/1988 |
| WO | WO 92/016142 | 10/1992 |
| WO | WO 93/006776 | 4/1993 |
| WO | WO 95/005621 | 2/1995 |
| WO | WO 95/016387 | 6/1995 |
| WO | WO 96/013208 | 5/1996 |
| WO | WO 96/041138 | 12/1996 |
| WO | WO 96/041566 | 12/1996 |
| WO | WO 97/001985 | 1/1997 |
| WO | WO 97/029678 | 8/1997 |
| WO | WO 97/029710 | 8/1997 |
| WO | WO 98/043071 | 10/1998 |
| WO | WO 00/018290 | 4/2000 |
| WO | WO 00/042911 | 7/2000 |
| WO | WO 00/059374 | 10/2000 |
| WO | WO 01/013790 | 3/2001 |
| WO | WO 01/030414 | 5/2001 |
| WO | WO 01/050433 | 7/2001 |
| WO | WO 01/058347 | 8/2001 |
| WO | WO 02/017780 | 3/2002 |
| WO | WO 02/026123 | 4/2002 |
| WO | WO 02/089664 | 11/2002 |
| WO | WO 03/020129 | 3/2003 |
| WO | WO 03/068060 | 8/2003 |
| WO | WO 03/077761 | 9/2003 |
| WO | WO 2004/034898 | 4/2004 |
| WO | WO 2004/038801 | 5/2004 |
| WO | WO 2005/004712 | 1/2005 |
| WO | WO 2005/011488 | 2/2005 |
| WO | WO 2006/017117 | 2/2006 |
| WO | WO 2006/094107 | 9/2006 |
| WO | WO 2006/094108 | 9/2006 |
| WO | WO 2006/094109 | 9/2006 |
| WO | WO 2006/094155 | 9/2006 |
| WO | WO 2006/094168 | 9/2006 |
| WO | WO 2006/094169 | 9/2006 |
| WO | WO 2006/094170 | 9/2006 |
| WO | WO 2006/094171 | 9/2006 |
| WO | WO 2006/094279 | 9/2006 |
| WO | WO 2006/115580 | 11/2006 |
| WO | WO 2006/118654 | 11/2006 |
| WO | WO 2009/013835 | 1/2009 |
| WO | WO 2009/137524 | 11/2009 |
| WO | WO 2011/051888 | 5/2011 |

OTHER PUBLICATIONS

Japanese Office Action in Application No. JP 2007-558208 dated May 8, 2012.
Definition of "gap", excerpt from Merriam-Webster's Collegiate Dictionary (11th ed.), 2005, 3 pages.
"Acrylic: Strong, stiff, clear plastic available in variety of brilliant colors", Copyright 2020. available at http://www.curbellplastics.com/Research-Solutions/Materials/Acrylic, 5 pages.
Quickspecs, Version 3, Nov. 20, 2003, HP iPAQ Pocket PC h4150 Series, 8 pages.
"Universal asynchronous receiver-transmitter", Wikipedia, available at https://en.wikipedia.org/wiki/Universal_asynchronous_receiver-transmitter, accessed Aug. 27, 2020, 10 pages.
McPherson, "How to Do Everything with Windows Mobile", McGraw Hill, 2006, 431 pages (uploaded in three parts).
B. Landon et al., "Master Visually Windows Mobile 2003", Wiley Publishing, Inc., 2004, 335 pages (uploaded in two parts).
National Instruments LabVIEW User Manual, National Instruments Corporation, Nov. 2001 Edition, Part No. 320999D-01, 293 pages.
Definition of "processor", excerpt from Merriam-Webster's Collegiate Dictionary (10th ed.), 1999, 6 pages.
Y. Mendelson et al., "Noninvasive Pulse Oximetry Utilizing Skin Reflectance Photoplethysmography", IEEE Transactions on Biomedical Engineering, vol. 35, No. 10, Oct. 1988, pp. 798-805.
J. Hayano et al., "Assessment of pulse rate variability by the method of pulse frequency demodulation." BioMedical Engineering OnLine vol. 4, No. 62, Nov. 1, 2005, doi:10.1186/1475-925X-4-62, pp. 1-12.
D. Thompson et al., "Pulse Oximeter Improvement with an ADC-DAC Feedback Loop and a Radical Reflectance Sensor," Proceedings of the 28th IEEE EMBS Annual International Conference, 2006, pp. 815-818.
Design of Pulse Oximeters, J.G. Webster, Institution of Physics Publishing, IOP Publishing Ltd, 1997, 131 pages (uploaded in 2 parts).
J. Yao, et al., "Stimulating Student Learning with a Novel 'In-House' Pulse Oximeter Design", Proceedings of the 2005 American Society for Engineering Education Annual Conference & Exposition, 2005, 14 pages.
V. Konig et al., "Reflectance Pulse Oximetry—Principles and Obstetric Application in the Zurich System," Journal of Clinical Monitoring and Computing, vol. 14, No. 6, Aug. 1998, pp. 403-412.
Service Manual: NPB-40 Handheld Pulse Oximeter, Nellcor Puritan Bennett, Inc., Copyright 2001, 55 pages.
Y. Mendelson, et al., "A Wearable Reflectance Pulse Oximeter for Remote Physiological Monitoring", Proceedings of the 28th IEEE Embs Annual International Conference, 2006, pp. 912-915.
Y. Mendelson, et al., "Measurement Site and Photodetector Size Considerations in Optimizing Power Consumption of a Wearable Reflectance Pulse Oximeter", Proceedings of the 25th IEEE EMBS Annual International Conference, 2003, pp. 3016-3019.
Y. Mendelson, et al., "Design and Evaluation of a New Reflectance Pulse Oximeter Sensor", Worcester Polytechnic Institute, Biomedical Engineering Program, Worcester, MA 01609, Association for the Advancement of Medical Instrumentation, vol. 22, No. 4, 1988, pp. 167-173.
Y. Mendelson, et al., "Skin Reflectance Pulse Oximetry: In Vivo Measurements from the Forearm and Calf", Journal of Clinical Monitoring, vol. 7, No. 1, Jan. 1991, pp. 7-12.
J. Bronzino et al., The Biomedical Engineering Handbook, Second Edition, CRC Press LLC, 2000, 21 pages.
J. Bronzino et al., Medical Devices and Systems, The Biomedical Engineering Handbook, Third Edition, Taylor & Francis Group, LLC, Apr. 2006, 20 pages.
J. Webster et al., Nanoparticles—Radiotherapy Accessories, Encyclopedia of Medical Devices and Instrumentation, Second Edition, vol. 5, Wiley-Interscience, 2006, 42 pages.

(56) References Cited

OTHER PUBLICATIONS

G. Comtois et al., "A Comparative Evaluation of Adaptive Noise Cancellation Algorithms for Minimizing Motion Artifacts in a Forehead-Mounted Wearable Pulse Oximeter," Proceedings of the 29th Annual International Conference of the IEEE EMBS, Aug. 2007, pp. 1528-1531.

S. LeGare et al., "A Device to Assess the Severity of Peripheral Edema," IEEE 33rd Annual Northeast Bioengineering Conference, 2007, pp. 257-258.

M. Corcoran et al., "A Humidifier for Olfaction Studies During Functional Magnetic Resonance Imaging," Proceedings of the IEEE 31st Annual Northeast Bioengineering Conference, 2005, pp. 1-2.

Y. Mendelson et al., "A Multiwavelength VIS-NIR Spectrometer for Pulsatile Measurement of Hemoglobin Derivatives in Whole Blood," 18th Annual International Conference of the IEEE Engineering in Medicine and Biology Society, 1996, pp. 134-135.

H. DiSpirito et al., "A Neural Stimulation System Model to Enhance Neural Integrated Circuit Design," 29th Southern Biomedical Engineering Conference, 2013, pp. 9-10.

R. P. Dresher et al., "A New Reflectance Pulse Oximeter Housing to Reduce Contact Pressure Effects," Proceedings of the IEEE 32nd Annual Northeast Bioengineering Conference, 2006, pp. 49-50.

D. Sen et al., "A New Vision for Preventing Pressure Ulcers: Wearable Wireless Devices Could Help Solve a Common-and-Serious-Problem," IEEE Pulse, vol. 9, No. 6, Nov. 2018, pp. 28-31.

G. Comtois et al., "A Noise Reference Input to an Adaptive Filter Algorithm for Signal Processing in a Wearable Pulse Oximeter," IEEE 33rd Annual Northeast Bioengineering Conference, 2007, pp. 106-107.

N. Selvaraj et al., "A Novel Approach Using Time-Frequency Analysis of Pulse-Oximeter Data to Detect Progressive Hypovolemia in Spontaneously Breathing Healthy Subjects," IEEE Transactions on Biomedical Engineering, vol. 58, No. 8, Aug. 2011, pp. 2272-2279.

S. Salehizadeh et al., "A Novel Time-Varying Spectral Filtering Algorithm for Reconstruction of Motion Artifact Corrupted Heart Rate Signals During Intense Physical Activities Using a Wearable Photoplethysmogram Sensor," Sensors 2016, vol. 16, No. 1, Dec. 2015, pp. 1-20.

A. Gendler et al., "A PAB-Based Multi-Prefetcher Mechanism," International Journal of Parallel Programming, vol. 34, No. 2, Apr. 2006, pp. 171-188.

J. Harvey et al., "A Portable Sensor for Skin Bioimpedance Measurements," International Journal of Sensors and Sensor Networks, vol. 7, No. 1, Aug. 2019, pp. 1-8.

D. Traviglia et al., "A Portable Setup for Comparing Transmittance and Reflectance Pulse Oximeters for Field Testing Applications," Proceedings of the IEEE 30th Annual Northeast Bioengineering Conference, 2004, pp. 212-213.

S. Xie et al., "A Predictive Model for Force-Sensing Resistor Nonlinearity for Pressure Measurement in a Wearable Wireless Sensor Patch," IEEE 61st International Midwest Symposium on Circuits and Systems, 2018, pp. 476-479.

P. Muller et al., "A Preliminary In-Vitro Evaluation and Comparative Study of Various Tissue pH Sensors," Proceedings of the 18th IEEE Annual Northeast Bioengineering Conference, 1992, pp. 158-159.

D. Dao et al., "A Robust Motion Artifact Detection Algorithm for Accurate Detection of Heart Rates From Photoplethysmographic Signals Using Time-Frequency Spectral Features," IEEE Journal of Biomedical and Health Informatics, vol. 21, No. 5, Sep. 2017, pp. 1242-1253.

G. Comtois et al., "A Wearable Wireless Reflectance Pulse Oximeter for Remote Triage Applications," Proceedings of the IEEE 32nd Annual Northeast Bioengineering Conference, 2006, pp. 53-54.

S. Djamasbi et al., "Affect Feedback during Crisis and Its Role in Improving IS Utilization," Proceedings of the 7th International Conference on Information Systems for Crisis Response and Management (ISCRAM), 2010, pp. 1-4.

B. Odegard et al., "An Analysis of Racewalking Styles Using a 2-Dimensional Mathematical Knee Model," Proceedings of the IEEE 23rd Northeast Bioengineering Conference, 1997, pp. 73-74.

S. Patrick et al., "An Electromyogram Simulator for Myoelectric Prosthesis Testing," Proceedings of the IEEE 36th Annual Northeast Bioengineering Conference (NEBEC), 2010, pp. 1-2.

Y. Mendelson et al., "An In Vitro Tissue Model for Evaluating the Effect of Carboxyhemoglobin Concentration on Pulse Oximetry," IEEE Transactions on Biomedical Engineering, vol. 36, No. 6, Jun. 1989, pp. 625-627.

C. Tamanaha et al., "An Inorganic Membrane Filter to Support Biomembrane-Mimetic Structures," Proceedings of 17th International Conference of the Engineering in Medicine and Biology Society, Sep. 1995, pp. 1559-1560.

A. Lader et al., "An Investigative Study of Membrane-Based Biosensors," Proceedings of the IEEE 17th Annual Northeast Bioengineering Conference, 1991, pp. 253-254.

N. Reljin et al., "Automatic Detection of Dehydration using Support Vector Machines," 14th Symposium on Neural Networks and Applications (NEUREL), Nov. 2018, pp. 1-6.

Y. Mendelson et al., Chapter 9: Biomedical Sensors, Introduction to Biomedical Engineering, Second Edition, Apr. 2005, pp. 505-548.

R. Peura et al., "Biotechnology for Biomedical Engineers," IEEE Engineering in Medicine and Biology, vol. 14, No. 2, Apr. 1995, pp. 199-200.

Y. Mendelson et al., "Blood Glucose Measurement by Multiple Attenuated Total Reflection and Infrared Absorption Spectroscopy," IEEE Transactions on Biomedical Engineering, vol. 37, No. 5, May 1990, pp. 458-465.

Y. Mendelson et al., "Carbon dioxide laser based multiple ATR technique for measuring glucose in aqueous solutions," Applied Optics, vol. 27, No. 24, Dec. 1988, pp. 5077-5081.

J. Harvey et al., "Correlation of bioimpedance changes after compressive loading of murine tissues in vivo," Physiological Measurement, vol. 40, No. 10, Oct. 2019, pp. 1-13.

B. Yocum et al., "Design of a Reflectance Pulse Oximeter Sensor and its Evaluation in Swine," Proceedings of the 15th Annual Northeast Bioengineering Conference, IEEE, 1989, pp. 239-240.

E. Tuite et al., "Design of Individual Balance Control Device Utilized during the Sit-to-Stand Task," ISB 2011 Brussels, 2011, pp. 1-2.

C. E. Darling et al., "Detecting Blood Loss With a Wearable Photoplethysmography Device," Annals of Emergency Medicine, vol. 68, No. 45, Oct. 2016, p. S116.

N. Reljin et al., "Detection of Blood Loss in Trauma Patients using Time-Frequency Analysis of Photoplethysmographic Signal," IEEE-EMBS International Conference on Biomedical and Health Informatics (BHI), 2016, pp. 118-121.

Y. Xu et al., "Drowsiness Control Center by Photoplethysmogram," 38th Annual Northeast Bioengineering Conference (NECBEC), IEEE, 2012, pp. 430-431.

M. Last et al., Chapter 14: Early Warning from Car Warranty Data using a Fuzzy Logic Technique, Scalable Fuzzy Algorithms for Data Management and Analysis: Methods and Design, 2010, pp. 347-364.

W. Johnston et al., "Effects of Motion Artifacts on Helmet-Mounted Pulse Oximeter Sensors," Proceedings of the IEEE 30th Annual Northeast Bioengineering Conference, 2014, pp. 214-215.

A. Nagre et al., "Effects of Motion Artifacts on Pulse Oximeter Readings from Different Facial Regions," Proceedings of the IEEE 31st Annual Northeast Bioengineering Conference, 2005, pp. 1-3.

R. Kasbekar et al., "Evaluation of key design parameters for mitigating motion artefact in the mobile reflectance PPG signal to improve estimation of arterial oxygenation," Physiological Measurement, vol. 39, No. 7, Jul. 2018, pp. 1-12.

Y. Mendelson et al., "Evaluation of the Datascope ACCUSAT Pulse Oximeter in Healthy Adults," Journal of Clinical Monitoring, vol. 4, No. 1, Jan. 1988, pp. 59-63.

W. S. Johnston et al., "Extracting Breathing Rate Information from a Wearable Reflectance Pulse Oximeter Sensor," Proceedings of the 26th Annual International Conference of the IEEE EMBS, Sep. 2004, pp. 5388-5391.

(56) References Cited

OTHER PUBLICATIONS

W. Johnston et al., "Extracting Heart Rate Variability from a Wearable Reflectance Pulse Oximeter," Proceedings of the IEEE 31st Annual Northeast Bioengineering Conference, 2005, pp. 1-2.
C. Tamanaha et al., "Feasibility Study of an Inorganic Membrane Filter as a Support for Biomembrane-Mimetic Structures," Proceedings of the IEEE 21st Annual Northeast Bioengineering Conference, 1995, pp. 99-101.
J. McNeill et al., "Flexible Sensor for Measurement of Skin Pressure and Temperature in a Clinical Setting," 2016 IEEE Sensors, Nov. 2016, pp. 1-3.
P. Bhandare et al., "Glucose determination in simulated blood serum solutions by Fourier transforms infrared spectroscopy: investigation of spectral interferences," Vibrational Spectroscopy, vol. 6, No. 3, Mar. 1994, pp. 363-378.
P. Bhandare et al. "Glucose Determination in Simulated Plasma Solutions Using Infrared Spectrophotometry," 14th Annual International Conference of the IEEE Engineering in Medicine and Biology Society, Nov. 1992, pp. 163-164.
C. Tamanahpba et al., "Humidity and Cation Dependency of Purple Membrane Based Biosensors," Proceedings of the 18th IEEE Annual Northeast Bioengineering Conference, Mar. 1992, pp. 107-108.
K. M. Warren et al., "Improving Pulse Rate Measurements during Random Motion Using a Wearable Multichannel Reflectance Photoplethysmograph," Sensors (Basel), vol. 16, No. 3, Mar. 2016, p. 1-18.
W. S. Johnston et al., "Investigation of Signal Processing Algorithms for an Embedded Microcontroller-Based Wearable Pulse Oximeter," Proceedings of the 28th IEEE EMBS Annual International Conference, Sep. 2006, pp. 5888-5891.
P. Bhandare et al., "IR Spectrophotometric Measurement of Glucose in Phosphate Buffered Saline Solutions: Effects of Temperature and pH," Proceedings of the 18th IEEE Annual Northeast Bioengineering Conference, 1992, pp. 103-104.
P. C. Branche et al., "Measurement Reproducibility and Sensor Placement Considerations in Designing a Wearable Pulse Oximeter for Military Applications," Proceedings of the IEEE 30th Annual Northeast Bioengineering Conference, 2004, pp. 216-217.
Y. Mendelson et al., "Multi-channel pulse oximetry for wearable physiological monitoring," IEEE International Conference on Body Sensor Networks, 2013, pp. 1-6.
P. Bhandare et al., "Multivariate Determination of Glucose in Whole Blood Using Partial Least-Squares and Artificial Neural Networks Based on Mid-Infrared Spectroscopy," Society for Applied Spectroscopy, vol. 47, No. 8, 1993, pp. 1214-1221.
E. Morillo et al., "Multiwavelength Transmission Spectrophotometry in the Pulsatile Measurement of Hemoglobin Derivatives in Whole Blood," Proceedings of the IEEE 23rd Northeast Bioengineering Conference, 1997, pp. 5-6.
P. Bhandare et al., "Neural Network Based Spectral Analysis of Multicomponent Mixtures for Glucose Determination," Proceedings of the IEEE, 17th Annual Northeast Bioengineering Conference, 1991, pp. 249-250.
Y. Mendelson et al., "Noninvasive Transcutaneous Monitoring of Arterial Blood Gases," IEEE Transactions on Biomedical Engineering, vol. BME-31, No. 12, Dec. 1984, pp. 792-800.
M. Savage et al., "Optimizing Power Consumption in the Design of a Wearable Wireless Telesensor: Comparison of Pulse Oximeter Modes," IEEE 29th Annual Proceedings of Bioengineering Conference, 2003, pp. 150-151.
J. Harvey et al., "OxiMA: A Frequency-Domain Approach to Address Motion Artifacts in Photoplethysmograms for Improved Estimation of Arterial Oxygen Saturation and Pulse Rate," IEEE Transactions on Biomedical Engineering, vol. 66, No. 2, Feb. 2019, pp. 311-318.
C. Pujary et al., "Photodetector Size Considerations in the Design of a Noninvasive Reflectance Pulse Oximeter for Telemedicine Applications," Proceedings of the IEEE 29th Annual Bioengineering Conference, 2003, pp. 148-149.

J. Chong et al., "Photoplethysmograph Signal Reconstruction Based on a Novel Hybrid Motion Artifact Detection-Reduction Approach. Part I: Motion and Noise Artifact Detection," Annals of Biomedical Engineering, vol. 42, No. 11, Nov. 2014, pp. 2238-2250.
S. M. A. Salehizadeh et al., "Photoplethysmograph Signal Reconstruction based on a Novel Motion Artifact Detection-Reduction Approach. Part II: Motion and Noise Artifact Removal," Annals of Biomedical Engineering, vol. 42, May 2014, pp. 2251-2263.
C. G. Scully et al., "Physiological Parameter Monitoring from Optical Recordings With a Mobile Phone," IEEE Transactions on Biomedical Engineering, vol. 59, No. 2, Feb. 2012, pp. 303-306.
D. Sen et al., "Pressure Ulcer Prevention System: Validation in a Clinical Setting," IEEE Life Sciences Conference (LSC), 2018, pp. 105-108.
Y. Mendelson et al., Pulse Oximetry: Theory and Applications for Noninvasive Monitoring, Clinical Chemistry, vol. 38, No. 9, 1992, pp. 1601-1607.
Y. Mendelson, Pulse Oximetry, PowerPoint, UMass Center for Clinical and Translational Science Research Retreat, 2017, 22 pages.
E. Stohr et al., "Quantitative FT-IR Spectrometry of Blood Constituents," 14th Annual International Conference of the IEEE Engineering in Medicine and Biology Society, 1992, pp. 173-174.
E. Stohr et al., "Quantitative FTIR Spectrophotometry of Cholesterol and Other Blood Constituents and their Interference with the In-Vitro Measurement of Blood Glucose," Proceedings of the 18th IEEE Annual Northeast Bioengineering Conference, 1992, pp. 105-106.
R. P. Dresher et al., "Reflectance Forehead Pulse Oximetry: Effects of Contact Pressure During Walking," Proceedings of the 28th IEEE EMBS Annual International Conference, Sep. 2006, pp. 3529-3532.
P. Branche et al., "Signal Quality and Power Consumption of a New Prototype Reflectance Pulse Oximeter Sensor," Proceedings of the IEEE 31st Annual Northeast Bioengineering Conference, 2005, pp. 1-2.
N. Selvaraj et al., "Statistical Approach for the Detection of Motion/Noise Artifacts in Photoplethysmogram," 33rd Annual International Conference of the IEEE EMBS, Sep. 2011, pp. 4972-4975.
C. Tamanaha et al., "Surface Modification of y-$Al_2O_3$ Filters by Chemisorption of Alkyltrichlorosilane Molecules," 18th Annual International Conference of the IEEE Engineering in Medicine and Biology Society, 1996, pp. 2069-2070.
D. Sen et al., "Time-Domain-Based Measurement Technique for Pressure Measurement in a Wearable Wireless Sensor Patch," IEEE International Symposium on Circuits and Systems (ISCAS), 2018, pp. 1-5.
N. Reljin et al., "Using support vector machines on photoplethysmographic signals to discriminate between hypovolemia and euvolemia," PLoS One, vol. 13, No. 3, Mar. 2018, pp. 1-14.
Y. Mendelson et al., "Variations in Optical Absorption Spectra of Adult and Fetal Hemoglobins and Its Effect on Pulse Oximetrvky," IEEE Transactions on Biomedical Engineering, vol. 36, No. 8, Aug. 1989, pp. 844-848.
K. Chon et al., "Wearable Wireless Sensor for Multi-Scale Physiological Monitoring," Worcester Polytechnic Institute, Oct. 2014, 82 pages.
K. Chon et al., "Wearable Wireless Sensor for Multi-Scale Physiological Monitoring," Worcester Polytechnic Institute, Oct. 2015, 142 pages.
J. McNeill et al., "Wearable Wireless Sensor Patch for Continuous Monitoring of Skin Temperature, Pressure, and Relative Humidity," IEEE International Symposium on Circuits and Systems (ISCAS), 2017, pp. 1-4.
D. Sen et al., "Wireless Sensor Patch Suitable for Continuous Monitoring of Contact Pressure in a Clinical Setting," 16th IEEE International New Circuits and Systems Conference (NEWCAS), 2018, pp. 91-95.
K. Hickle et al., "Wireless Pressure Ulcer Sensor," Annals of Plastic Surgery, vol. 82, Supplement 3, Apr. 2019, pp. S215-S221.
K. Self, Application Note 78—Using Power Management with High-Speed Microcontrollers, Maxim Integrated Products, Inc., Mar. 29, 2001, 25 pages.

(56) References Cited

OTHER PUBLICATIONS

Service Manual: Nellcor Symphony N-3000 Pulse Oximeter, Nellcor Puritan Bennett, Inc., Copyright 1996, 110 pages.
Home Use Guide: Nellcor Symphony N-3000 Pulse Oximeter, Nellcor Puritan Bennett, Inc., Copyright 1996, 50 pages.
Operator's Manual: Nellcor N-200 Pulse Oximeter, Nellcor Incorporated, Copyright 2003, 96 pages.
S. Kastle et al., "A New Family of Sensors for Pulse Oximetry," Hewlett-Packard Journal, Article 7, Feb. 1997, pp. 1-17.
M. Nogawa et al., "A Novel Hybrid Reflectance Pulse Oximeter Sensor with Improved Linearity and General Applicability to Various Portions of the Body," Proceedings of the 20th Annual International Conference of the IEEE Engineering in Medicine and Biology Society, vol. 20, No. 4, 1998, pp. 1858-1861.
J. Hodby, "A ratio-measuring detection system for use in pulsed spectroscopic measurements," Journal of Physics E: Scientific Instruments, vol. 3, 1970, pp. 229-233.
K. Li et al., "A Wireless Reflectance Pulse Oximeter with Digital Baseline Control for Unfiltered Photoplethysmograms," IEEE Transactions on Biomedical Circuits and Systems, Nov. 2011, pp. 1-11.
D. Thompson et al., "A Small, High-Fidelity Reflectance Pulse Oximeter," American Society for Engineering Education, 2007, 14 pages.
K. Li et al., "A High-Performance Wireless Reflectance Pulse Oximeter for Photo-Plethysmogram Acquisition and Analysis in the Classroom," American Society for Engineering Education, 2010, 12 pages.
M. J. Hayes, "Artefact Reduction in Photoplethysmography," Doctoral thesis, Department of Electronic and Electrical Engineering, Loughborough University, Nov. 1998, 195 pages, (uploaded in 2 parts).
A. C. M. Dassel et al., "Effect of location of the sensor on reflectance pulse oximetry," British Journal of Obstetrics and Gynaecology, vol. 104, Aug. 1997, pp. 910-916.
RF Cafe, Electronic Warfare and Radar Systems Engineering Handbook, Duty Cycle, available at https://www.rfcafe.com/references/electrical/ew-radar-handbook/duty-cycle.htm, retrieved Jul. 11, 2020, 3 pages.
Y. Shimada et al., "Evaluation of a new reflectance pulse oximeter for clinical applications," Medical & Biological Engineering & Computing, vol. 29, No. 5, Sep. 1991, pp. 557-561.
S. Takatani et al., "Experimental and Clinical Evaluation of a Noninvasive Reflectance Pulse Oximeter Sensor," Journal of Clinical Monitoring, vol. 8, No. 4, Oct. 1992, pp. 257-266.
K. Ono et al., "Fiber optic reflectance spectrophotometry system for in vivo tissue diagnosis," Applied Optics, vol. 30, No. 1, Jan. 1991, pp. 98-105.
M. Barr, "Introduction to Pulse Width Modulation (PWM)," Barr Group, Embedded Systems Programming, Sep. 2001, pp. 1-3.
P. P. Vaidyanathan, "Multirate Digital Filters, Filter Banks, Polyphase Networks, and Applications: A Tutorial," Proceedings of the IEEE, vol. 78, No. 1, Jan. 1990, pp. 56-93.
S. Oshima et al., "Optical Measurement of Blood Hematocrit on Medical Tubing with Dual Wavelength and Detector Model," 31st Annual International Conference of the IEEE EMBS, Sep. 2009, pp. 5891-5896.
Optoelectronics, Data Book 1990, Siemens Components, Inc., 770 pages, (uploaded in 7 parts).
OxiplexTS Near Infrared, Non-Invasive, Tissue Spectrometer Brochure, ISS, Inc., Copyright 2001, 6 pages.
J. A. Pologe, "Pulse Oximetry: Technical Aspects of Machine Design," International Anesthesiology Clinics, vol. 25, No. 3, 1987, pp. 137-153.
B. F. Koegh et al., "Recent findings in the use of reflectance oximetry: a critical review," Current Opinion in Anaesthesiology, vol. 18, 2005, pp. 649-654.
A. C. M. Dassel et al., "Reflectance Pulse Oximetry at the Forehead Improves by Pressure on the Probe," Journal of Clinical Monitoring, vol. 11, No. 4, Jul. 1995, pp. 237-244.
K. Faisst et al., "Reflectance pulse oximetry in neonates," European Journal of Obstetrics & Gynecology and Reproductive Biology, vol. 61, No. 2, Aug. 1995, pp. 117-122.
V. Konig et al., "Reflexions-Pulsoximetrie—Untersuchungen mit eigenem Mess-System," Biomedical Engineering, Biomedizinische Technik, vol. 37. No. s2, 1992, pp. 39-40.
3 pages of images, identified by bates numbers "APL-MAS_00057600", "APL-MAS_00057601", and "APL-MAS_00057602". Undated.
2 pages of images, identified by bates numbers "APL-MAS_00057598" and "APL-MAS_00057599". Undated.
Y. Mendelson et al., "A Mobile PDA-Based Wireless Pulse Oximeter," Proceedings of the IASTED International Conference, Jul. 2005, pp. 1-6.
Y. Mendelson et al., A Wearable Reflectance Pulse Oximeter for Remote Physiological Monitoring, PowerPoint, The Bioengineering Institute, Worcester Polytechnic Institute, 18 pages. Undated.
P. C. Branche et al., "A Wearable Wireless Reflectance Pulse Oximeter with Automatic and Remote On-Demand Activation," Annual Fall Meeting of the BMES, 2004, p. 1.
A Wireless Wearable Reflectance Pulse Oximeter Printout, The Bioengineering Institute, Worcester Polytechnic Institute, 1 page. Undated.
Y. Mendelson et al., A Wireless Wearable Reflectance-Based Forehead Pulse Oximeter, PowerPoint, The Bioengineering Institute, Worcester Polytechnic Institute, 8 pages. Undated.
Y. Mendelson et al., "Accelerometery-Based Adaptive Noise Cancellation for Remote Physiological Monitoring by a Wearable Pulse Oximeter," Proceedings of the 3rd IASTED International Conference on Telehealth, May 2007, pp. 28-33.
R. J. Duckworth et al., Field Testing of a Wireless Wearable Reflectance Pulse Oximeter Printout, Department of Electrical and Computer Engineering and Department of Biomedical Engineering, Worcester Polytechnic Institute, 1 page. Undated.
C. J. Pujary, "Investigation of Photodetector Optimization in Reducing Power Consumption by a Noninvasive Pulse Oximeter Sensor," Master thesis, Worcester Polytechnic Institute, Jan. 2004, 133 pages.
Y. Mendelson et al., "Minimization of LED Power Consumption in the Design of a Wearable Pulse Oximeter," Proceedings of the IASTED International Conference Biomedical Engineering, Jun. 2003, pp. 249-254.
V. Floroff, "PDA Interface for the WPI Wireless Physiological Monitor," Directed research, Department of Biomedical Engineering, Worcester Polytechnic Institute, Mar. 2006, 42 pages.
Wireless Wearable Reflectance Pulse Oximeter, PowerPoint, The Bioengineering Institute, Worcester Polytechnic Institute, TATRC, 10 pages. Undated.
V. Floroff, "Remote Pulse Oximetry: The wireless side of the TATRC project." Thesis, Worcester Polytechnic Institute, Feb. 2005, pp. 1-20.
Y. Mendelson et al., "The Feasibility of Measuring SpO$_2$ from the Head Using a Reflectance Pulse Oximeter: Effect of Motion Artifacts," Proceeding of the 3rd European Medical & Biological Engineering Conference, 2005, 5 pages.
R. Dresher, "Wearable Forehead Pulse Oximetry: Minimization of Motion and Pressure Artifacts," Master thesis, Worcester Polytechnic Institute, May 2006, 93 pages.
Y. Mendelson, "Wearable, Wireless, Noninvasive Physiological Sensing," The Bioengineering Institute, Worcester Polytechnic Institute, 2005, 2 pages.
Y. Mendelson et al., "Wireless Reflectance Pulse Oximetery for Remote Triage Application," Worcester Polytechnic Institute, 1 page. Undated.
A. V. Fontaine et al., "Reflectance-Based Pulse Oximetry for the Chest and Wrist", Worcester Polytechnic Institute, Digital WPI, Apr. 2013, pp. 132.
D. Thompson et al., "A Small, High-Fidelity Reflectance Pulse Oximeter", American Society for Engineering Education, Jan. 2007, pp. 15.
E. Geun et al., "Measurement Site and Applied Pressure Consideration in Wrist Photoplethysmography", The 23rd International Tech-

(56) References Cited

OTHER PUBLICATIONS nical Conference on Circuits/Systems, Computers and Communications (ITC-CSCC 2008), pp. 1129-1132.
F. H. Netter, M.D., "Atlas of Human Anatomy", Third Edition, Icon Learning Systems, Teterboro, New Jersey, 1989, pp. 81.
H. Lee et al., "Reflectance Pulse Oximetry: Practical Issues and Limitations", ICT Express 2, 2016, pp. 195-198.
T. S. Perry, "Should You Trust Apple's New Blood Oxygen Sensor?", IEEE Spectrum, https://spectrum.ieee.org/view-from-the-valley/biomedical/devices/should-you-trust-apples-new-blood-oxygen-sensor, Sep. 21, 2020, pp. 4.
Definition of "cover", excerpt from Merriam-Webster's Collegiate Dictionary (11th ed.), 2005, 3 pages.
Eugene Hecht, Excerpts of Optics, Second Edition, Addition-Wesley Publishing Company, 1990, 80 pages (pp. 79-143, 211-220).
Eugene Hecht, Optics, Fourth Edition, Pearson Education, Inc., Addison Wesley, 2002, 355 pages. (uploaded in three parts).
Eugene Hecht, Optics, Second Edition, Addition-Wesley Publishing Company, 1990, 348 pages. (uploaded in two parts).
H. Ding et al., "Refractive indices of human skin tissues at eight wavelengths and estimated dispersion relations between 300 and 1600 nm", Physics in Medicine & Biology, vol. 51, 2006, pp. 1479-1489.
S. N. Kasarova et al., "Analysis of the dispersion of optical plastic materials", Optical Materials vol. 29, 2007, pp. 1481-1490.
U.S. Appl. No. 12/082,810, filed Apr. 14, 2008, Al-Ali.
U.S. Appl. No. 14/148,462, filed Jan. 6, 2014, Al-Ali et al.
U.S. Appl. No. 15/694,541, filed Sep. 1, 2017, Smith et al.
"Application Note 84 Use of Add-Only Memory for Secure Storage of Monetary Equivalent Data," Dallas Semiconductor, Jun. 22, 1999, in 5 pages.
Burritt, Mary F.; Current Analytical Approaches to Measuring Blood Analytes; vol. 36; No. 8(B); 1990.
Dallas Semiconductor Corp: DS2430A Announcement, retrieved Jun. 10, 1998, in 2 pages. https://web.archive.org/web/19980610045525/http://dalsemi.com/News_Center/New_Products/1996/243.0a.html.
European Examination Report, re EP App. No. 06 736 798.7, dated Dec. 2, 2015.
European Examination Report, re EP App. No. 06 736 798.7, dated Jul. 18, 2016.
European Examination Report, re EP App. No. 06 736 798.7, dated Jan. 19, 2018.
European Examination Report, re EP App. No. 19203300.9, dated Apr. 2, 2020.
European Examination Report, re EP Application No. 06736799.5, dated Nov. 30, 2012.
International Search Report for EP Appl. No. 10191029 completed May 25, 2012 (dated Jun. 5, 2012) in 5 pages.
European Extended Search Report, re EP Application No. 10191029.7, dated Jun. 5, 2012.
European Extended Search Report re EPO App. No. 10162402.1, SR dated Aug. 9, 2010.
European Examination Report dated Apr. 1, 2010, re EP App. No. 08 744 412.1-2319.
European Examination Report dated Mar. 18, 2011, re EP App. No. 08 744 412.1-2319.
European Examination Report dated Sep. 2, 2010, re EP App. No. 08 744 412.1-2319.
European Examination Report, re EP Application No. 12163719.3, dated Feb. 6, 2013.
European Extended Search Report, re EP Application No. 12163719.3, dated Jun. 18, 2012.
Favennec, J.M. "Smart sensors in industry." J. Phys. E: Sci. Instrum. 20(9): Sep. 1987, pp. 1087-1090.
Hall, et al., Jeffrey W.; Near-Infrared Spectrophotometry: A New Dimension in Clinical Chemistry; vol. 38; No. 9; 1992.
International Preliminary Report on Patentability for PCT/US2010/058981 issued Jun. 5, 2012, dated Jun. 14, 2012.
International Search Report for PCT/US2006/007516, dated Jan. 11, 2007, in 4 pages.

Japanese Final Office Action re Amendments re JP Application No. 2007-558249, dated Apr. 17, 2012.
Japanese First Office Action (Notice of Reasons for Rejection), re JP App. No. 2007-558207, dated Jun. 28, 2011.
Japanese First Office Action (Notice of Reasons for Rejection), re JP App. No. 2007-558247, dated Jun. 28, 2011.
Japanese Office Action (Decision of Rejection), re JP Application No. JP 2007-558328, dated Nov. 20, 2012.
Japanese Office Action (Notice of Allowance), re JP App. No. 2007-558247, dated Oct. 24, 2011.
Japanese Office Action (Notice of Reasons for Rejection) re JP App. No. 2007-558246, dated Jun. 28, 2011.
Japanese Office Action (Notice of Reasons for Rejection), re JP App. No. 2007-558238, dated Jun. 28, 2011.
Japanese Office Action (Official Inquiry) re JP App. No. 2007-558246, dated Dec. 11, 2012.
Japanese Office Action (Official Inquiry), re JP App. No. 2007-558238/Appeal No. 2012-004053, dated Dec. 11, 2012.
Japanese Office Action (Reasons for Rejection) re JP App. No. 2007-558246, dated Nov. 1, 2011.
Japanese Office Action re JP Application No. 2007-558249, dated Aug. 28, 2012.
Japanese Office Action re JP Application No. 2007-558249, dated Jul. 13, 2011.
Japanese Office Action re JP Application No. 2007-558249, dated Nov. 8, 2011.
Japanese Office Action re JP Application No. JP 2007-558208, dated Aug. 23, 2011.
Japanese Office Action re JP Application No. JP 2007-558248, dated Nov. 27, 2012.
Japanese Office Action re JP Application No. JP 2007-558248, dated Nov. 8, 2011.
Japanese Office Action re JP Application No. 2007-558209, dated Oct. 25, 2011.
Japanese Office Action re JP Application No. 2007-558209, dated Oct. 30, 2012.
Japanese Office Action re JP Application No. 2007-558245, dated Oct. 25, 2011.
Japanese Office Action re JP Application No. 2007-558245, dated/mailed Jan. 15, 2013.
Japanese Office Action re JP Application No. 2007-558245, dated Oct. 29, 2013.
Japanese Office Action, Decision of Rejection of Amendment, re JP Application No. JP 2007-558328, dated Jun. 25, 2013.
Japanese Office Action, re JP Application No. 2007-558237, dated Aug. 2, 2011.
Japanese Office Action, re JP Application No. 2012-045419, dated Jun. 26, 2012.
Japanese Office Action, re JP Application No. JP 2007-558237, dated Oct. 16, 2012.
Jones, K.L., et al. "A Protocol for Automatic Sensor Detection and Identification in a Wireless Biodevice Network," IEEE, Jun. 1998, 6 pages.
Kuenstner, et al., J. Todd; Measurement of Hemoglobin in Unlysed Blood by Near-Infrared Spectroscopy; vol. 48; No. 4, 1994.
Manzke, et al., B., Multi Wavelength Pulse OXimetry in the Measurement of Hemoglobin Fractions; vol. 2676, 1996.
"Medical." 50 Ways to Touch Memory. 3rd ed. Dallas: Dallas Semiconductor Corporation, Aug. 1994: pp. 24-25. Print.
Naumenko, E. K.; Choice of Wavelengths for Stable Determination of Concentrations of Hemoglobin Derivatives from Absorption Spectra of Erythrocytes; vol. 63; No. 1; pp. 60-66 Jan.-Feb. 1996; Original article submitted Nov. 3, 1994.
Patent Cooperation Treaty (PCT) International Search Report; PCT/US 2006/007389; dated Jul. 17, 2006; pp. 1-9.
PCT International Search Report; PCT/US2006/007387; dated Jul. 17, 2006; pp. 1-9.
PCT International Search Report; PCT/US2006/007388; dated Jul. 17, 2006; pp. 1-9.
PCT International Search Report; PCT/US2006/007506; dated Jul. 17, 2006; pp. 1-10.
PCT International Search Report; PCT/US2006/007536; dated Jul. 17, 2006; pp. 1-9.

(56) References Cited

OTHER PUBLICATIONS

PCT International Search Report; PCT/US2006/007537; dated Jul. 17, 2006; pp. 1-10.
PCT International Search Report; PCT/US2006/007538; dated Jul. 17, 2006; pp. 1-9.
PCT International Search Report; PCT/US2006/007539; dated Jul. 17, 2006; pp. 1-9.
PCT International Search Report; PCT/US2006/007540; dated Jul. 17, 2006; pp. 1-9.
PCT International Search Report; PCT/US2006/007958; dated Jul. 17, 2006; pp. 1-8.
PCT International Written Opinion and Search Report, re PCT App. No. PCT/US2006/007506, dated Jul. 17, 2006.
PCT Report on Patentability of International Application No. PCT/US2008/058327, dated Jun. 30, 2009, in 12 pages.
Schmitt, Joseph M.; Simple Photon Diffusion Anaylsis of the Effects of Multiple Scattering on Pulse Oximetry; Mar. 14, 1991; revised Aug. 30, 1991.
Schmitt, Joseph M.; Zhou, Guan-Xiong; Miller, Justin, Measurement of Blood Hematocrit by Dual-wavelength Near-IR Photoplethysmography, published May 1992, Proc. SPIE vol. 1641, p. 150-161, Physiological Monitoring and Early Detection Diagnostic Methods, Thomas S. Mang; Ed. (SPIE homepage), in 12 pages.
Schnapp, et al., L.M.; Pulse Oximetry. Uses and Abuses.; Chest 1990; 98; 1244-1250001 10.1378/Chest.98.5.1244.
Subramanian, S., et al. "Design for Constraint Violation Detection in Safety-Critical Systems," IEEE, Nov. 1998: pp. 1-8.

\* cited by examiner

DETAIL A-A

SECTION A-A

SECTION B-B

SECTION A-A

SECTION B-B

SECTION A-A

SECTION B-B

SECTION A-A

SECTION B-B

SECTION A-A

SECTION B-B

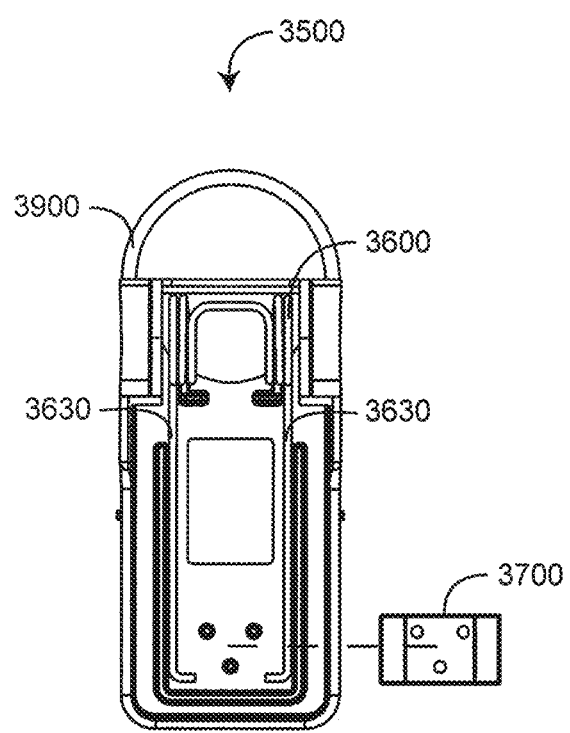
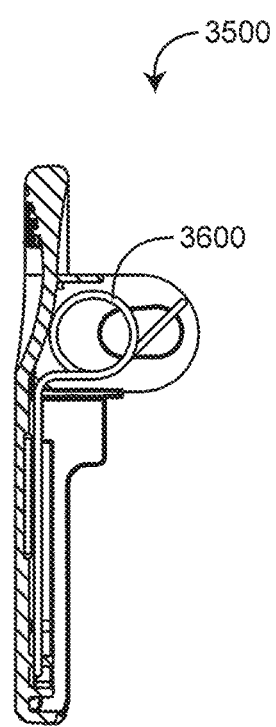
FIG. 35A
FIG. 35B

SECTION B-B

SECTION A-A

SECTION A-A

MULTIPLE WAVELENGTH SENSOR EMITTERS

PRIORITY CLAIM

Any and all applications for which a foreign or domestic priority claim is identified in the Application Data Sheet as filed with the present application are incorporated by reference under 37 CFR 1.57 and made a part of this specification in their entireties and for all purposes.

INCORPORATION BY REFERENCE OF RELATED APPLICATIONS

The present application is related to the following U.S. utility applications:

|   | application Ser. No. | Filing Date | Title | Atty Dock. |
|---|---|---|---|---|
| 1 | 11/367,013 | Mar. 1, 2006 | Multiple Wavelength Sensor Emitters | MLR.002A |
|   | 11/546,932 | Oct. 12, 2006 | Disposable Wavelength Optical Sensor | MLR.002CP1 |
| 2 | 11/366,995 | Mar. 1, 2006 | Multiple Wavelength Sensor Equalization | MLR.003A |
| 3 | 11/366,209 | Mar. 1, 2006 | Multiple Wavelength Sensor Substrate | MLR.004A |
| 4 | 11/366,210 | Mar. 1, 2006 | Multiple Wavelength Sensor Interconnect | MLR.005A |
| 5 | 11/366,833 | Mar. 1, 2006 | Multiple Wavelength Sensor Attachment | MLR.006A |
| 6 | 11/366,997 | Mar. 1, 2006 | Multiple Wavelength Sensor Drivers | MLR.009A |
| 7 | 11/367,034 | Mar. 1, 2006 | Physiological Parameter Confidence Measure | MLR.010A |
| 8 | 11/367,036 | Mar. 1, 2006 | Configurable Physiological Measurement System | MLR.011A |
| 9 | 11/367,033 | Mar. 1, 2006 | Noninvasive Multi-Parameter Patient Monitor | MLR.012A |
| 10 | 11/367,014 | Mar. 1, 2006 | Noninvasive Multi-Parameter Patient Monitor | MLR.013A |
| 11 | 11/366,208 | Mar. 1, 2006 | Noninvasive Multi-Parameter Patient Monitor | MLR.014A |
| 12 | 12/056,179 | Mar. 26, 2008 | Multiple Wavelength Optical Sensor | MLR.015A |
| 13 | 12/082,810 | Apr. 14, 2008 | Optical Sensor Assembly | MLR.015A2 |

The present application incorporates the foregoing disclosures herein by reference.

BACKGROUND

Spectroscopy is a common technique for measuring the concentration of organic and some inorganic constituents of a solution. The theoretical basis of this technique is the Beer-Lambert law, which states that the concentration $c_i$ of an absorbent in solution can be determined by the intensity of light transmitted through the solution, knowing the pathlength $d_\lambda$, the intensity of the incident light $I_{0,\lambda}$, and the extinction coefficient $\varepsilon_{i,\lambda}$ at a particular wavelength $\lambda$. In generalized form, the Beer-Lambert law is expressed as:

$$I_\lambda = I_{0,\lambda} e^{-d_\lambda \cdot \mu_{a,\lambda}} \quad (1)$$

$$\mu_{a,\lambda} = \sum_{i=1}^{n} \varepsilon_{i,\lambda} \cdot c_i \quad (2)$$

where $\mu_{a,\lambda}$ is the bulk absorption coefficient and represents the probability of absorption per unit length. The minimum number of discrete wavelengths that are required to solve EQS. 1-2 are the number of significant absorbers that are present in the solution.

A practical application of this technique is pulse oximetry, which utilizes a noninvasive sensor to measure oxygen saturation ($SpO_2$) and pulse rate. In general, the sensor has light emitting diodes (LEDs) that transmit optical radiation of red and infrared wavelengths into a tissue site and a detector that responds to the intensity of the optical radiation after absorption (e.g., by transmission or transreflectance) by pulsatile arterial blood flowing within the tissue site. Based on this response, a processor determines measurements for $SpO_2$, pulse rate, and can output representative plethysmographic waveforms. Thus, "pulse oximetry" as used herein encompasses its broad ordinary meaning known to one of skill in the art, which includes at least those noninvasive procedures for measuring parameters of circulating blood through spectroscopy. Moreover, "plethysmograph" as used herein (commonly referred to as "photoplethysmograph"), encompasses its broad ordinary meaning known to one of skill in the art, which includes at least data representative of a change in the absorption of particular wavelengths of light as a function of the changes in body tissue resulting from pulsing blood. Pulse oximeters capable of reading through motion induced noise are available from Masimo Corporation ("Masimo") of Irvine, Calif. Moreover, portable and other oximeters capable of reading through motion induced noise are disclosed in at least U.S. Pat. Nos. 6,770,028, 6,658,276, 6,157,850, 6,002,952 5,769,785, and 5,758,644, which are owned by Masimo and are incorporated by reference herein. Such reading through motion oximeters have gained rapid acceptance in a wide variety of medical applications, including surgical wards, intensive care and neonatal units, general wards, home care, physical training, and virtually all types of monitoring scenarios.

SUMMARY

There is a need to noninvasively measure multiple physiological parameters, other than, or in addition to, oxygen saturation and pulse rate. For example, hemoglobin species that are also significant under certain circumstances are carboxyhemoglobin and methemoglobin. Other blood parameters that may be measured to provide important clinical information are fractional oxygen saturation, total hemoglobin (Hbt), bilirubin and blood glucose, to name a few.

One aspect of a physiological sensor is light emitting sources, each activated by addressing at least one row and at least one column of an electrical grid. The light emitting sources transmit light having multiple wavelengths and a detector is responsive to the transmitted light after attenuation by body tissue.

Another aspect of a physiological sensor is light emitting sources capable of transmitting light having multiple wavelengths. Each of the light emitting sources includes a first contact and a second contact. The first contacts of a first set of the light emitting sources are in communication with a first conductor and the second contacts of a second set of the light emitting sources are in communication with a second conductor. A detector is capable of detecting the transmitted light attenuated by body tissue and outputting a signal indicative of at least one physiological parameter of the body tissue. At least one light emitting source of the first set and at least one light emitting source of the second set are not common to the first and second sets. Further, each of the first set and the second set comprises at least two of the light emitting sources.

A further aspect of a physiological sensor sequentially addresses light emitting sources using conductors of an electrical grid so as to emit light having multiple wavelengths that when attenuated by body tissue is indicative of at least one physiological characteristic. The emitted light is detected after attenuation by body tissue.

BRIEF DESCRIPTION OF THE DRAWINGS

FIGS. 35A-B are plan and cross sectional views, respectively, of a spring assembly embodiment;

DETAILED DESCRIPTION

Overview

In this application, reference is made to many blood parameters. Some references that have common shorthand designations are referenced through such shorthand designations. For example, as used herein, HbCO designates carboxyhemoglobin, HbMet designates methemoglobin, and Hbt designates total hemoglobin. Other shorthand designations such as COHb, MetHb, and tHb are also common in the art for these same constituents. These constituents are generally reported in terms of a percentage, often referred to as saturation, relative concentration or fractional saturation. Total hemoglobin is generally reported as a concentration in g/dL. The use of the particular shorthand designators presented in this application does not restrict the term to any particular manner in which the designated constituent is reported.

Figure 1:
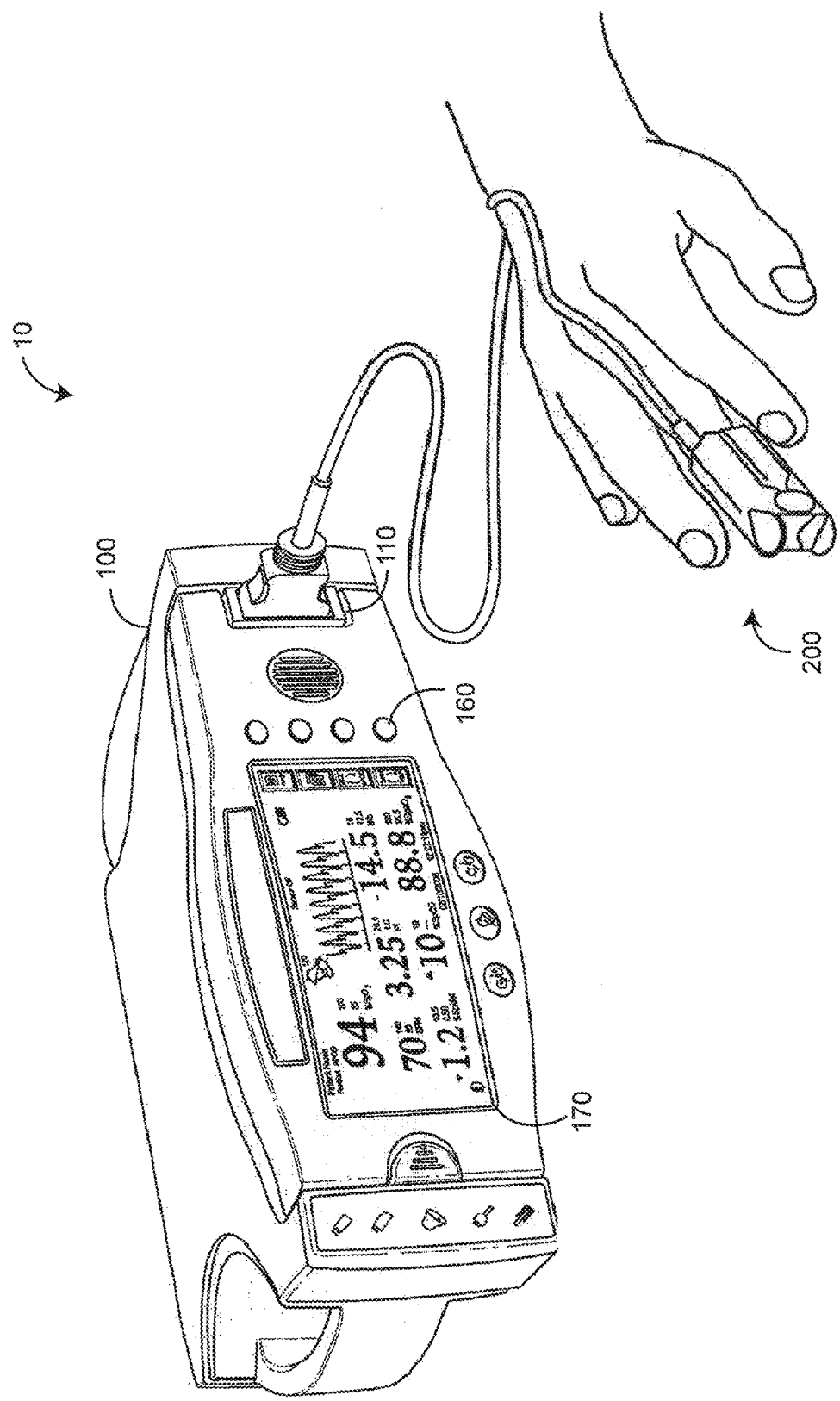
FIG. 1 is a perspective view of a physiological measurement system utilizing a multiple wavelength sensor.

FIG. 1 illustrates a physiological measurement system 10 having a monitor 100 and a multiple wavelength sensor assembly 200 with enhanced measurement capabilities as compared with conventional pulse oximetry. The physiological measurement system 10 allows the monitoring of a person, including a patient. In particular, the multiple wavelength sensor assembly 200 allows the measurement of blood constituent and related parameters in addition to oxygen saturation and pulse rate. Alternatively, the multiple wavelength sensor assembly 200 allows the measurement of oxygen saturation and pulse rate with increased accuracy or robustness as compared with conventional pulse oximetry.

In one embodiment, the sensor assembly 200 is configured to plug into a monitor sensor port 110. Monitor keys 160 provide control over operating modes and alarms, to name a few. A display 170 provides readouts of measured parameters, such as oxygen saturation, pulse rate, HbCO and HbMet to name a few.

Figure 2A:
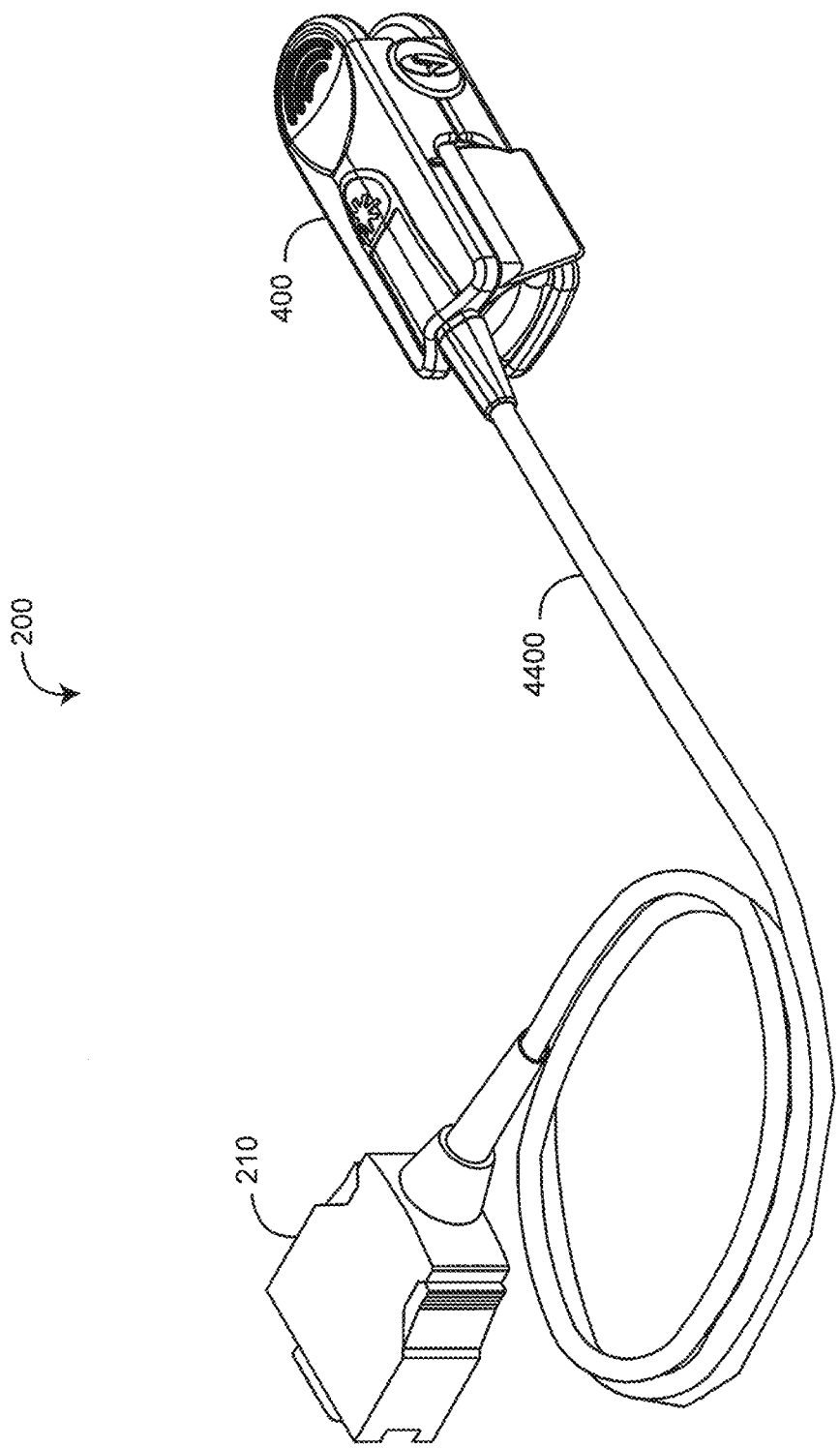
FIGS. 2A-C are perspective views of multiple wavelength sensor embodiments.

FIG. 2A illustrates a multiple wavelength sensor assembly 200 having a sensor 400 adapted to attach to a tissue site, a sensor cable 4400 and a monitor connector 210. In one embodiment, the sensor 400 is incorporated into a reusable finger clip adapted to removably attach to, and transmit light through, a fingertip. The sensor cable 4400 and monitor connector 210 are integral to the sensor 400, as shown. In alternative embodiments, the sensor 400 may be configured separately from the cable 440 and connector 210.

Figure 2B:
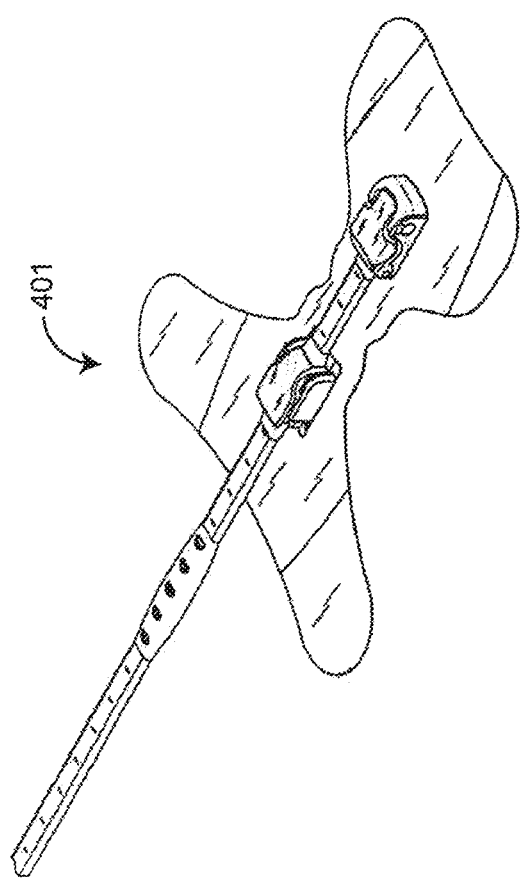
Figure 2C:
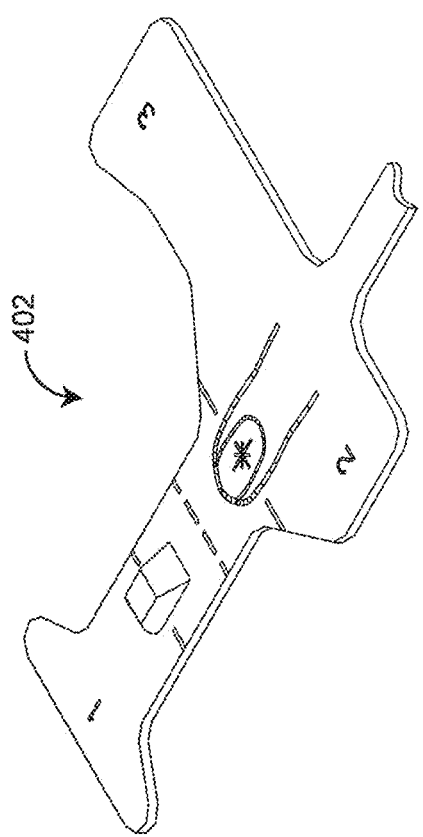

FIGS. 2B-C illustrate alternative sensor embodiments, including a sensor 401 (FIG. 2B) partially disposable and partially reusable (resposable) and utilizing an adhesive attachment mechanism. Also shown is a sensor 402 (FIG. 2C) being disposable and utilizing an adhesive attachment mechanism. In other embodiments, a sensor may be configured to attach to various tissue sites other than a finger, such as a foot or an ear. Also a sensor may be configured as a reflectance or transflectance device that attaches to a forehead or other tissue surface.

Figure 3:
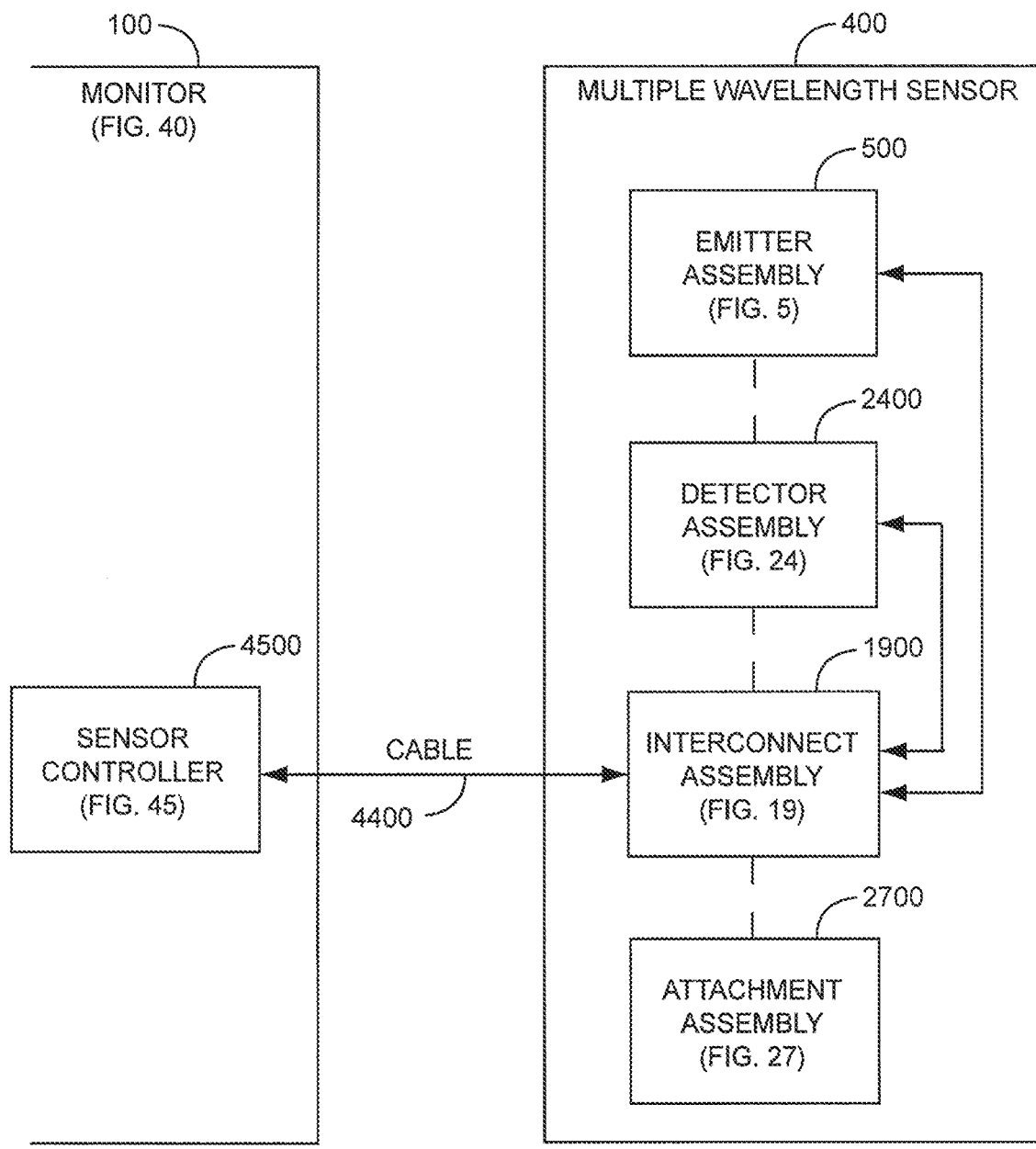
FIG. 3 is a general block diagram of a multiple wavelength sensor and sensor controller.

FIG. 3 illustrates a sensor assembly 400 having an emitter assembly 500, a detector assembly 2400, an interconnect assembly 1900 and an attachment assembly 2700. The emitter assembly 500 responds to drive signals received from a sensor controller 4500 in the monitor 100 via the cable 4400 so as to transmit optical radiation having a plurality of wavelengths into a tissue site. The detector assembly 2400 provides a sensor signal to the monitor 100 via the cable 4400 in response to optical radiation received after attenuation by the tissue site. The interconnect assembly 1900 provides electrical communication between the cable 4400 and both the emitter assembly 500 and the detector assembly 2400. The attachment assembly 2700 attaches the emitter assembly 500 and detector assembly 2400 to a tissue site, as described above. The emitter assembly 500 is described in further detail with respect to FIG. 5, below. The interconnect assembly 1900 is described in further detail with respect to FIG. 19, below. The detector assembly 2400 is described in further detail with respect to FIG. 24, below. The attachment assembly 2700 is described in further detail with respect to FIG. 27, below.

Figure 4:
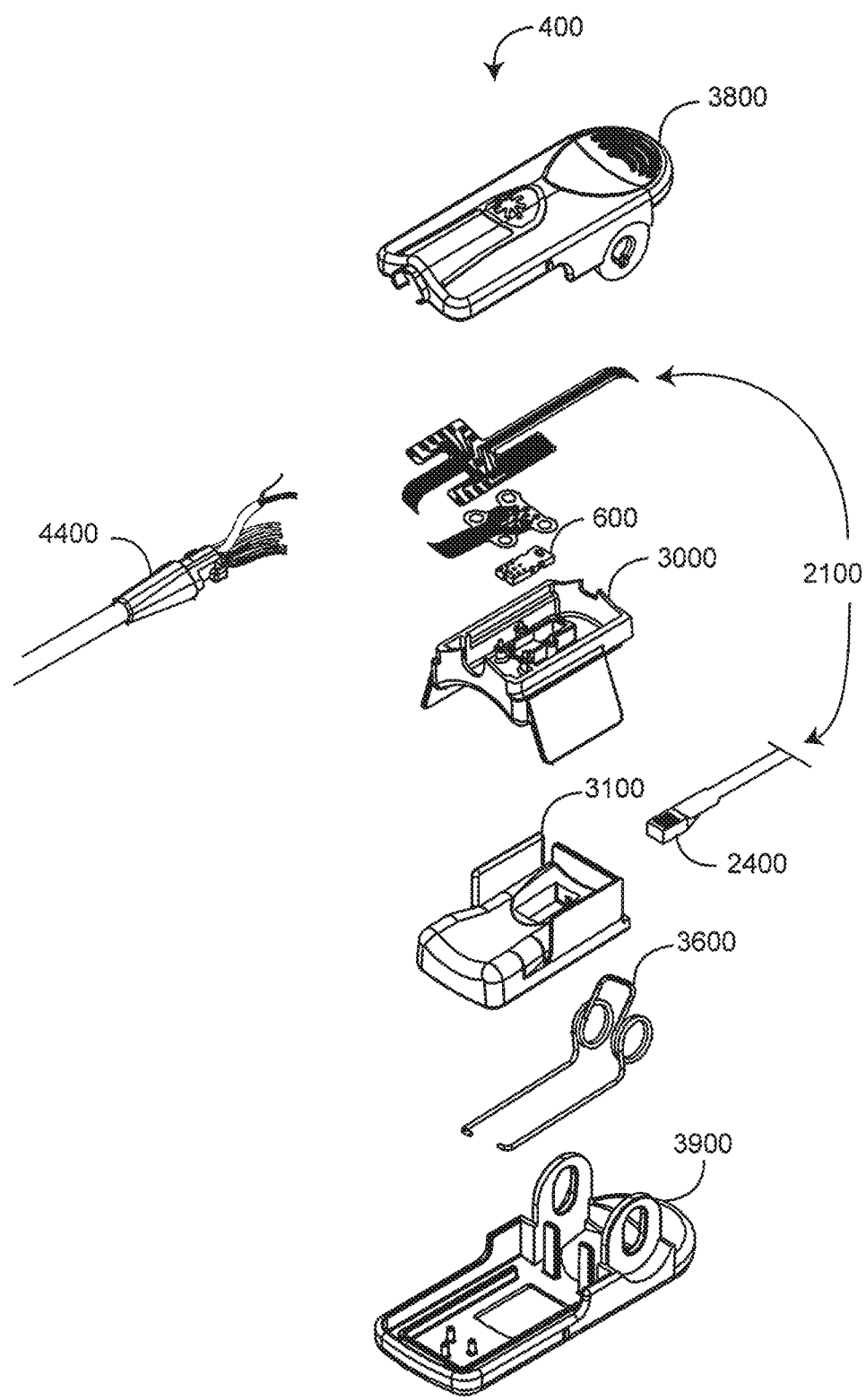
FIG. 4 is an exploded perspective view of a multiple wavelength sensor embodiment.

FIG. 4 illustrates a sensor 400 embodiment that removably attaches to a fingertip. The sensor 400 houses a multiple wavelength emitter assembly 500 and corresponding detector assembly 2400. A flex circuit assembly 1900 mounts the emitter and detector assemblies 500, 2400 and interconnects them to a multi-wire sensor cable 4400. Advantageously, the sensor 400 is configured in several respects for both wearer comfort and parameter measurement performance. The flex circuit assembly 1900 is configured to mechanically decouple the cable 4400 wires from the emitter and detector assemblies 500, 2400 to reduce pad stiffness and wearer discomfort. The pads 3000, 3100 are mechanically decoupled from shells 3800, 3900 to increase flexibility and wearer comfort. A spring 3600 is configured in hinged shells 3800, 3900 so that the pivot point of the finger clip is well behind the fingertip, improving finger attachment and more evenly distributing the clip pressure along the finger.

As shown in FIG. 4, the detector pad 3100 is structured to properly position a fingertip in relationship to the detector assembly 2400. The pads have flaps that block ambient light. The detector assembly 2400 is housed in an enclosure so as to reduce light piping from the emitter assembly to the detector assembly without passing through fingertip tissue. These and other features are described in detail below. Specifically, emitter assembly embodiments are described with respect to FIGS. 5-18. Interconnect assembly embodiments, including the flexible circuit assembly 1900, are described with respect to FIGS. 19-23. Detector assembly embodiments are described with respect to FIGS. 24-26. Attachment assembly embodiments are described with respect to FIGS. 27-39.

Emitter Assembly

Figure 5:
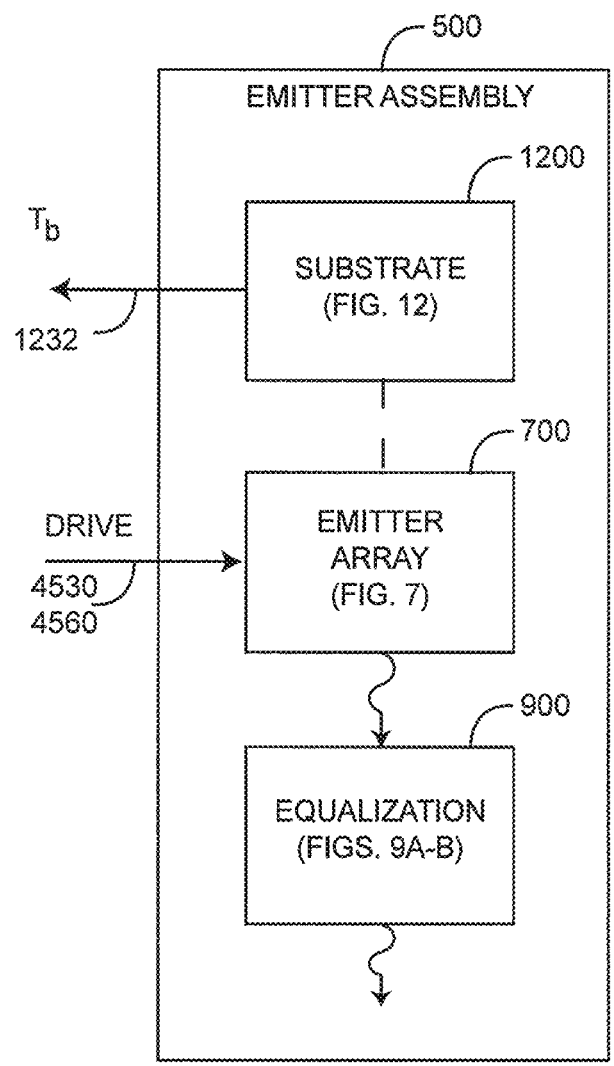
FIG. 5 is a general block diagram of an emitter assembly.

FIG. 5 illustrates an emitter assembly 500 having an emitter array 700, a substrate 1200 and equalization 900. The emitter array 700 has multiple light emitting sources, each activated by addressing at least one row and at least one column of an electrical grid. The light emitting sources are capable of transmitting optical radiation having multiple wavelengths. The equalization 900 accounts for differences in tissue attenuation of the optical radiation across the multiple wavelengths so as to at least reduce wavelength-dependent variations in detected intensity. The substrate 1200 provides a physical mount for the emitter array and emitter-related equalization and a connection between the emitter array and the interconnection assembly. Advantageously, the substrate 1200 also provides a bulk temperature measurement so as to calculate the operating wavelengths for the light emitting sources. The emitter array 700 is described in further detail with respect to FIG. 7, below. Equalization is described in further detail with respect to FIG. 9, below. The substrate 1200 is described in further detail with respect to FIG. 12, below.

Figure 6:
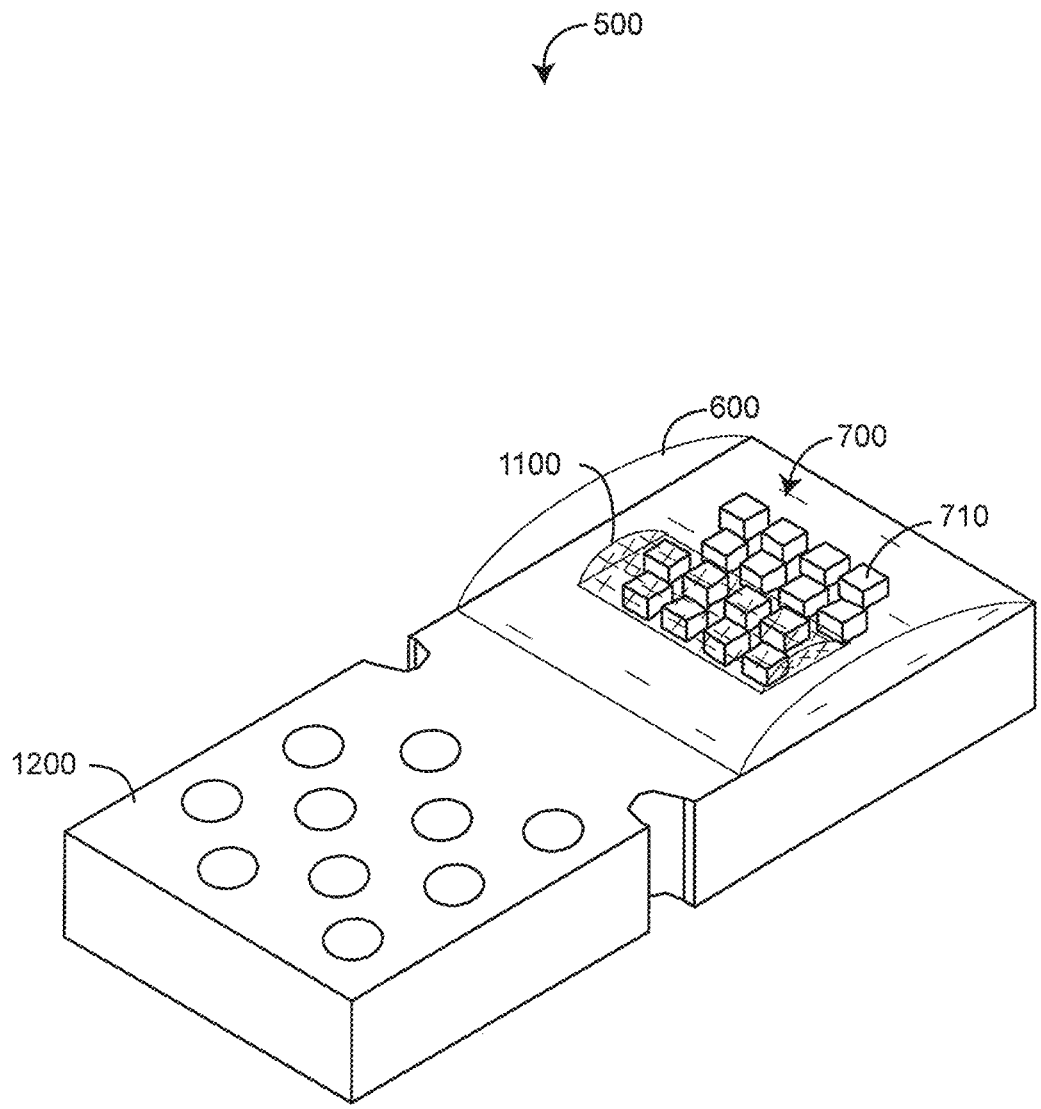
FIG. 6 is a perspective view of an emitter assembly embodiment.

FIG. 6 illustrates an emitter assembly 500 embodiment having an emitter array 700, an encapsulant 600, an optical filter 1100 and a substrate 1200. Various aspects of the emitter assembly 500 are described with respect to FIGS. 7-18, below. The emitter array 700 emits optical radiation having multiple wavelengths of predetermined nominal values, advantageously allowing multiple parameter measurements. In particular, the emitter array 700 has multiple light emitting diodes (LEDs) 710 that are physically arranged and electrically connected in an electrical grid to facilitate drive control, equalization, and minimization of optical pathlength differences at particular wavelengths. The optical filter 1100 is advantageously configured to provide intensity equalization across a specific LED subset. The substrate 1200 is configured to provide a bulk temperature of the emitter array 700 so as to better determine LED operating wavelengths.

Emitter Array

Figure 7:
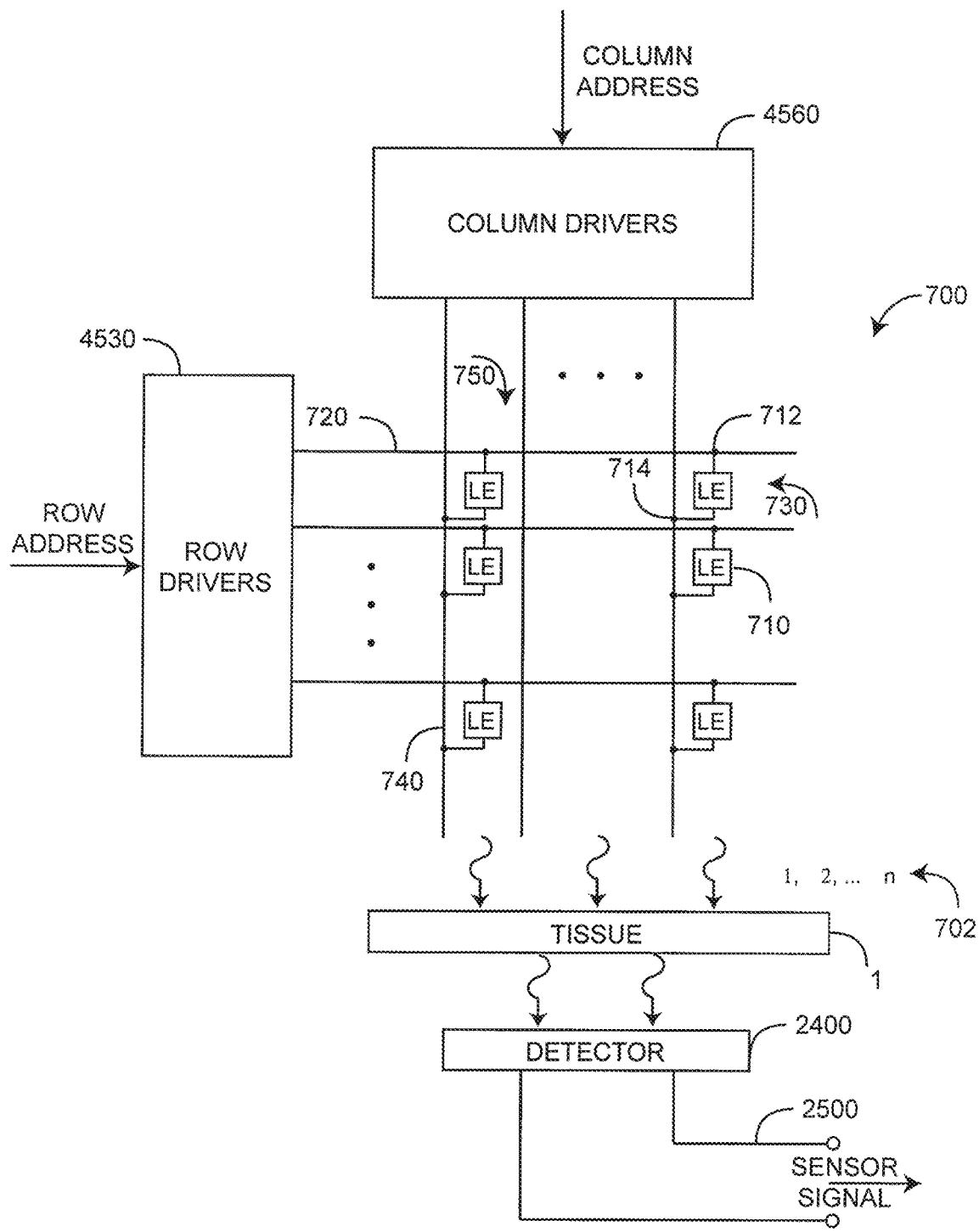
FIG. 7 is a general block diagram of an emitter array.

FIG. 7 illustrates an emitter array 700 having multiple light emitters (LE) 710 capable of emitting light 702 having multiple wavelengths into a tissue site 1. Row drivers 4530 and column drivers 4560 are electrically connected to the light emitters 710 and activate one or more light emitters 710 by addressing at least one row 720 and at least one column 740 of an electrical grid. In one embodiment, the light emitters 710 each include a first contact 712 and a second contact 714. The first contact 712 of a first subset 730 of light emitters is in communication with a first conductor 720 of the electrical grid. The second contact 714 of a second subset 750 of light emitters is in communication with a second conductor 740. Each subset comprises at least two light emitters, and at least one of the light emitters of the first and second subsets 730, 750 are not in common. A detector 2400 is capable of detecting the emitted light 702 and outputting a sensor signal 2500 responsive to the emitted light 702 after attenuation by the tissue site 1. As such, the sensor signal 2500 is indicative of at least one physiological parameter corresponding to the tissue site 1, as described above.

Figure 8:
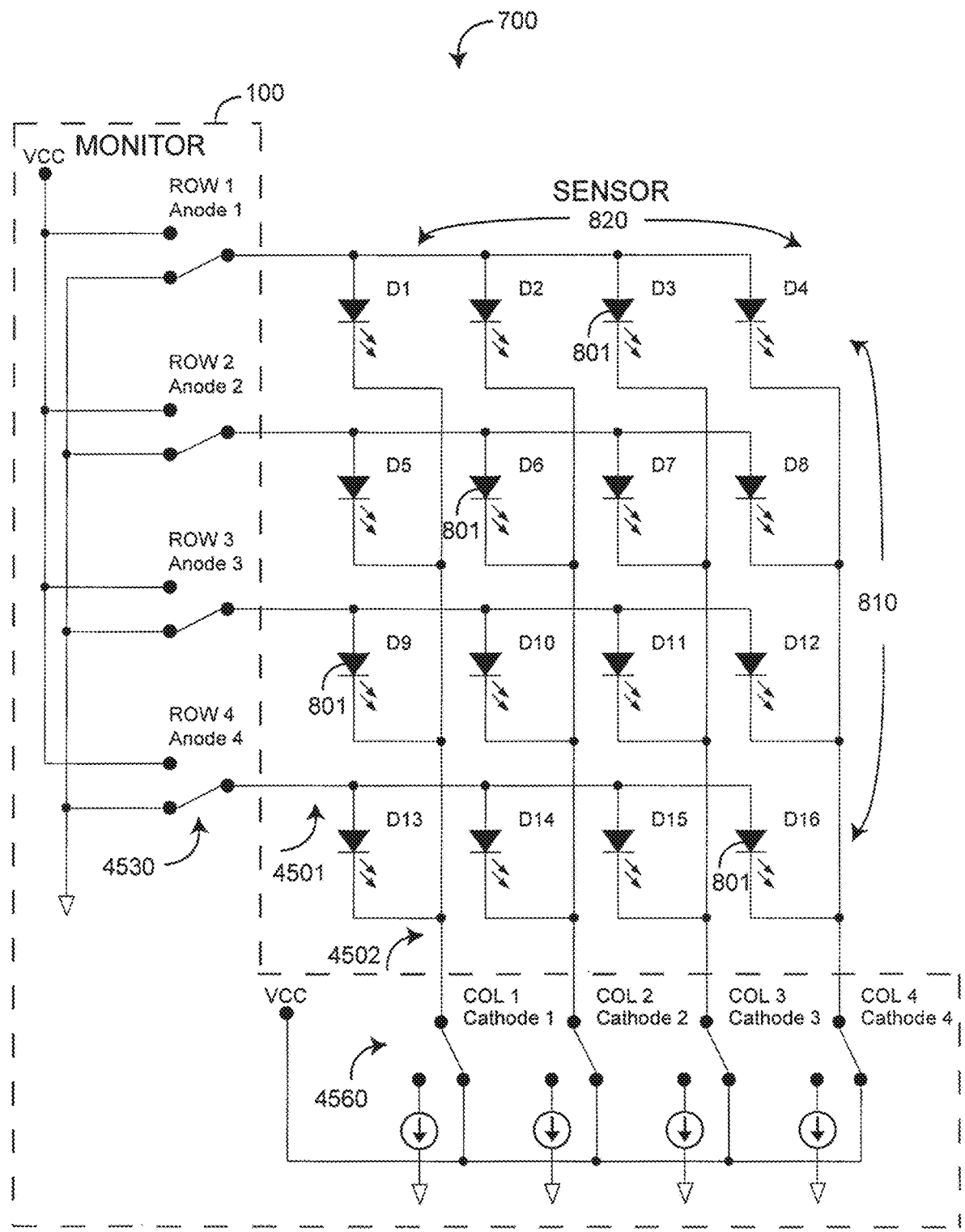
FIG. 8 is a schematic diagram of an emitter array embodiment.

FIG. 8 illustrates an emitter array 700 having LEDs 801 connected within an electrical grid of n rows and m columns totaling n+m drive lines 4501, 4502, where n and m integers greater than one. The electrical grid advantageously minimizes the number of drive lines required to activate the LEDs 801 while preserving flexibility to selectively activate individual LEDs 801 in any sequence and multiple LEDs 801 simultaneously. The electrical grid also facilitates setting LED currents so as to control intensity at each wavelength, determining operating wavelengths and monitoring total grid current so as to limit power dissipation. The emitter array 700 is also physically configured in rows 810. This physical organization facilitates clustering LEDs 801 according to wavelength so as to minimize pathlength variations and facilitates equalization of LED intensities.

As shown in FIG. 8, one embodiment of an emitter array 700 comprises up to sixteen LEDs 801 configured in an electrical grid of four rows 810 and four columns 820. Each of the four row drive lines 4501 provide a common anode connection to four LEDs 801, and each of the four column drive lines 4502 provide a common cathode connection to four LEDs 801. Thus, the sixteen LEDs 801 are advantageously driven with only eight wires, including four anode drive lines 812 and four cathode drive lines 822. This compares favorably to conventional common anode or cathode LED configurations, which require more drive lines. In a particular embodiment, the emitter array 700 is partially populated with eight LEDs having nominal wavelengths as shown in TABLE 1. Further, LEDs having wavelengths in the range of 610-630 nm are grouped together in the same row. The emitter array 700 is adapted to a physiological measurement system 10 (FIG. 1) for measuring $H_bCO$ and/or METHb in addition to $S_pO_2$ and pulse rate.

TABLE 1

Nominal LED Wavelengths

| LED | λ | Row | Col |
|---|---|---|---|
| D1 | 630 | 1 | 1 |
| D2 | 620 | 1 | 2 |
| D3 | 610 | 1 | 3 |
| D4 |  | 1 | 4 |
| D5 | 700 | 2 | 1 |
| D6 | 730 | 2 | 2 |
| D7 | 660 | 2 | 3 |
| D8 | 805 | 2 | 4 |
| D9 |  | 3 | 1 |
| D10 |  | 3 | 2 |
| D11 |  | 3 | 3 |
| D12 | 905 | 3 | 4 |
| D13 |  | 4 | 1 |
| D14 |  | 4 | 2 |
| D15 |  | 4 | 3 |
| D16 |  | 4 | 4 |

Also shown in FIG. 8, row drivers 4530 and column drivers 4560 located in the monitor 100 selectively activate the LEDs 801. In particular, row and column drivers 4530, 4560 function together as switches to Vcc and current sinks, respectively, to activate LEDs and as switches to ground and Vcc, respectively, to deactivate LEDs. This push-pull drive configuration advantageously prevents parasitic current flow in deactivated LEDs. In a particular embodiment, only one row drive line 4501 is switched to Vcc at a time. One to four column drive lines 4502, however, can be simultaneously switched to a current sink so as to simultaneously activate multiple LEDs within a particular row. Activation of two or more LEDs of the same wavelength facilitates intensity equalization, as described with respect to FIGS. 9-11, below. LED drivers are described in further detail with respect to FIG. 45, below.

Although an emitter assembly is described above with respect to an array of light emitters each configured to transmit optical radiation centered around a nominal wavelength, in another embodiment, an emitter assembly advantageously utilizes one or more tunable broadband light sources, including the use of filters to select the wavelength, so as to minimize wavelength-dependent pathlength differences from emitter to detector. In yet another emitter assembly embodiment, optical radiation from multiple emitters each configured to transmit optical radiation centered around a nominal wavelength is funneled to a tissue site point so as to minimize wavelength-dependent pathlength differences. This funneling may be accomplish with fiberoptics or mirrors, for example. In further embodiments, the LEDs 801 can be configured with alternative orientations with correspondingly different drivers among various other configurations of LEDs, drivers and interconnecting conductors.

Equalization

Figure 9:
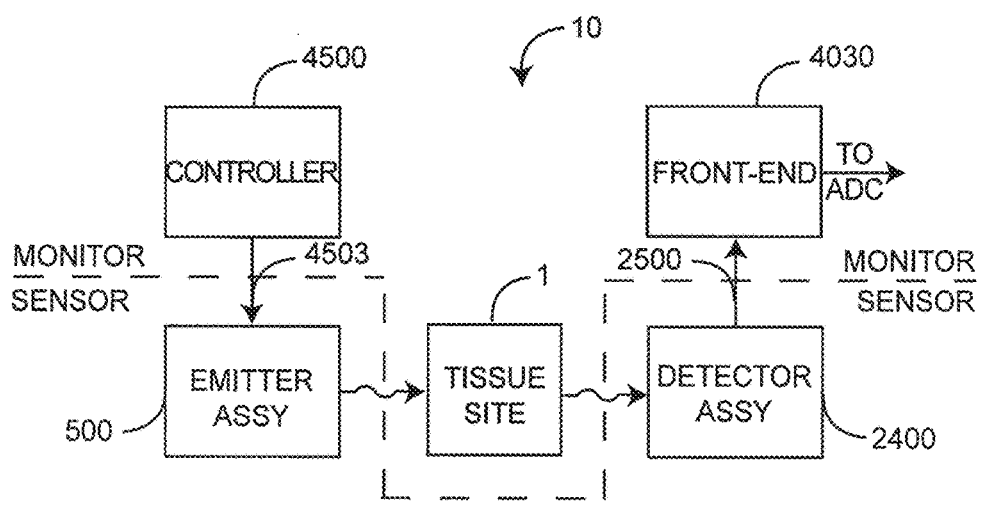
FIG. 9 is a general block diagram of equalization.
Figure 9:
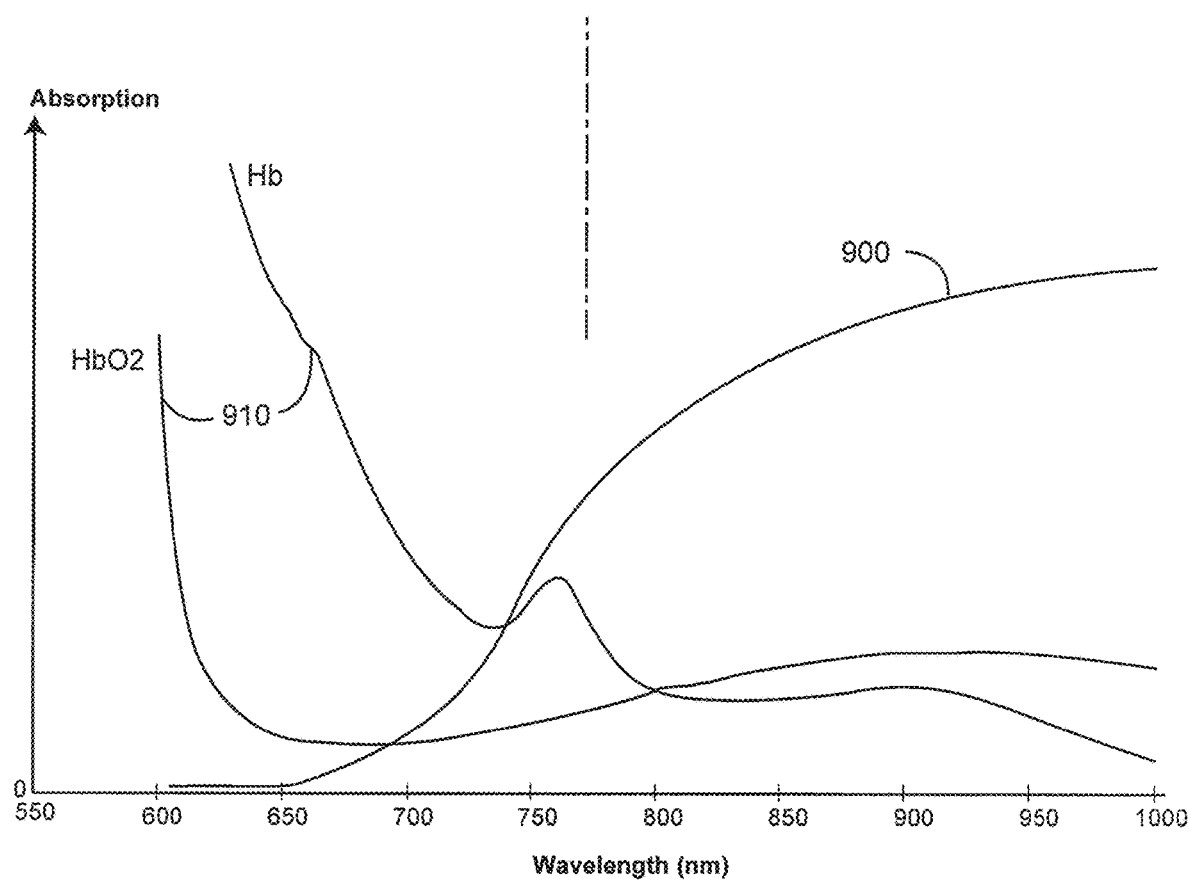

FIG. 9 illustrate a physiological parameter measurement system 10 having a controller 4500, an emitter assembly 500, a detector assembly 2400 and a front-end 4030. The emitter assembly 500 is configured to transmit optical radiation having multiple wavelengths into the tissue site 1. The detector assembly 2400 is configured to generate a sensor signal 2500 responsive to the optical radiation after tissue attenuation. The front-end 4030 conditions the sensor signal 2500 prior to analog-to-digital conversion (ADC).

FIG. 9 also generally illustrates equalization 900 in a physiological measurement system 10 operating on a tissue site 1. Equalization encompasses features incorporated into the system 10 in order to provide a sensor signal 2500 that falls well within the dynamic range of the ADC across the entire spectrum of emitter wavelengths. In particular, equalization compensates for the imbalance in tissue light absorption due to Hb and $HbO_2$ 910. Specifically, these blood constituents attenuate red wavelengths greater than IR wavelengths. Ideally, equalization 900 balances this unequal attenuation. Equalization 900 can be introduced anywhere in the system 10 from the controller 4500 to front-end 4000 and can include compensatory attenuation versus wavelength, as shown, or compensatory amplification versus or both.

Equalization can be achieved to a limited extent by adjusting drive currents from the controller 4500 and front-end 4030 amplification accordingly to wavelength so as to compensate for tissue absorption characteristics. Signal demodulation constraints, however, limit the magnitude of these adjustments. Advantageously, equalization 900 is also provided along the optical path from emitters 500 to detector 2400. Equalization embodiments are described in further detail with respect to FIGS. 10-11, below.

Figure 10A:
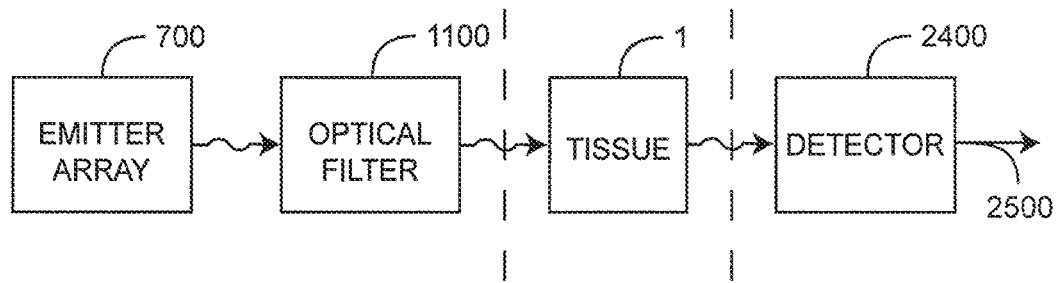
FIGS. 10A-D are block diagrams of various equalization embodiments.

FIGS. 10A-D illustrate various equalization embodiments having an emitter array 700 adapted to transmit optical radiation into a tissue site 1 and a detector assembly 2400 adapted to generate a sensor signal 2500 responsive to the optical radiation after tissue attenuation. FIG. 10A illustrates an optical filter 1100 that attenuates at least a portion of the optical radiation before it is transmitted into a tissue site 1. In particular, the optical filter 1100 attenuates at least a portion of the IR wavelength spectrum of the optical radiation so as to approximate an equalization curve 900 (FIG. 9).

Figure 10B:
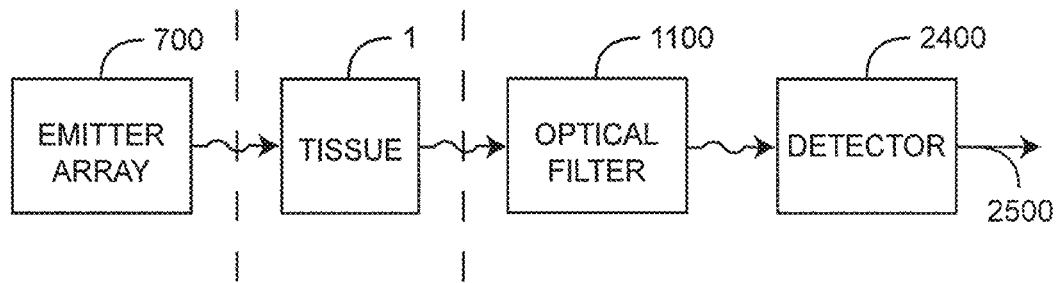

FIG. 10B illustrates an optical filter 1100 that attenuates at least a portion of the optical radiation after it is attenuated by a tissue site 1, where the optical filter 1100 approximates an equalization curve 900 (FIG. 9).

Figure 10C:
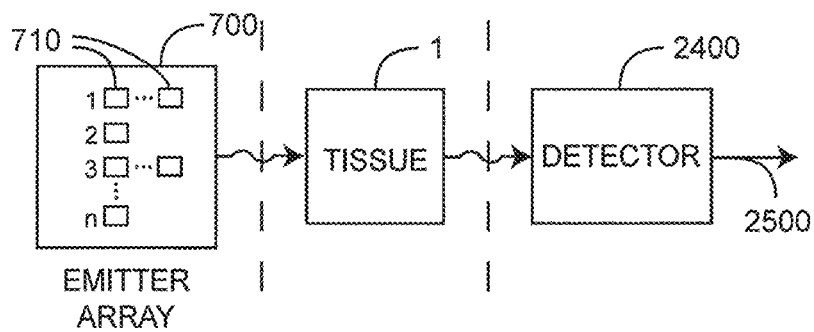
Figure 10D:
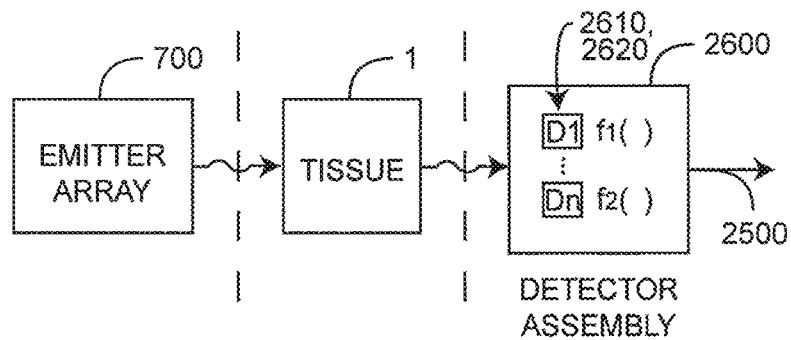

FIG. 10C illustrates an emitter array 700 where at least a portion of the emitter array generates one or more wavelengths from multiple light emitters 710 of the same wavelength. In particular, the same-wavelength light emitters 710 boost at least a portion of the red wavelength spectrum so as to approximately equalize the attenuation curves 910 (FIG. 9). FIG. 10D illustrates a detector assembly 2400 having multiple detectors 2610, 2620 selected so as to equalize the attenuation curves 910 (FIG. 9). To a limited extent, optical equalization can also be achieved by selection of particular emitter array 700 and detector 2400 components, e.g. LEDs having higher output intensities or detectors having higher sensitivities at red wavelengths. Although equalization embodiments are described above with respect to red and IR wavelengths, these equalization embodiments can be applied to equalize tissue characteristics across any portion of the optical spectrum.

Figure 11A:
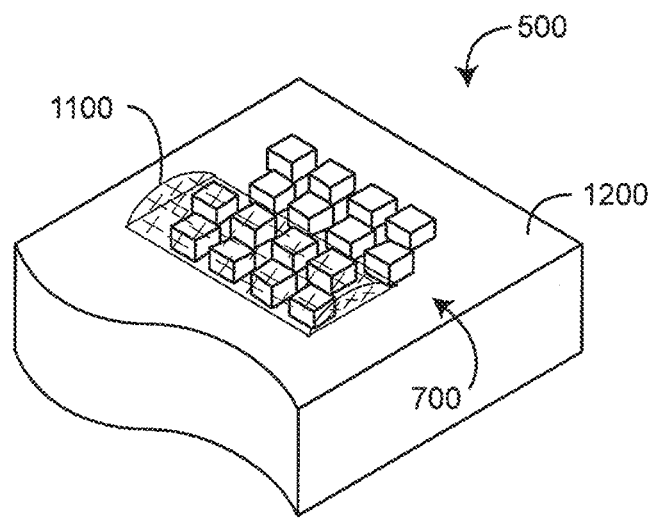
FIGS. 11A-C are perspective views of an emitter assembly incorporating various equalization embodiments.
Figure 11B:
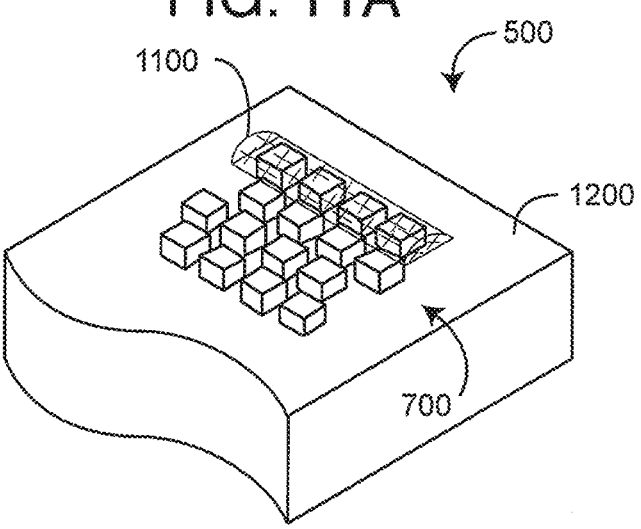
Figure 11C:
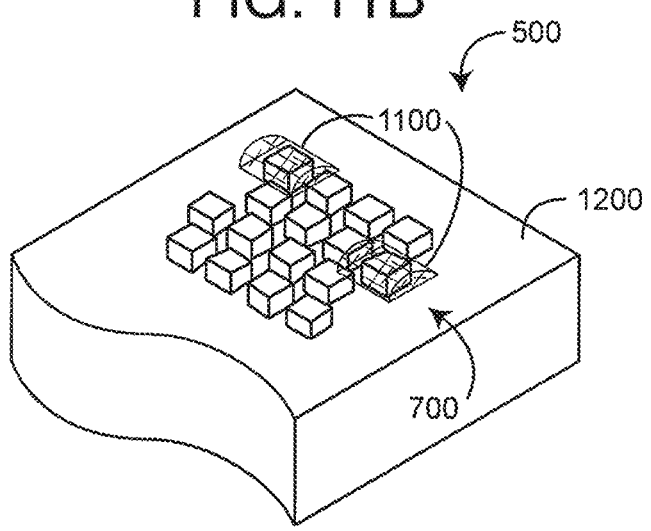

FIGS. 11A-C illustrates an optical filter 1100 for an emitter assembly 500 that advantageously provides optical equalization, as described above. LEDs within the emitter array 700 may be grouped according to output intensity or wavelength or both. Such a grouping facilitates equalization of LED intensity across the array. In particular, relatively low tissue absorption and/or relatively high output intensity LEDs can be grouped together under a relatively high attenuation optical filter. Likewise, relatively low tissue absorption and/or relatively low output intensity LEDs can be grouped together without an optical filter or under a relatively low or negligible attenuation optical filter. Further, high tissue absorption and/or low intensity LEDs can be grouped within the same row with one or more LEDs of the same wavelength being simultaneously activated, as described with respect to FIG. 10C, above. In general, there can be any number of LED groups and any number of LEDs within a group. There can also be any number of optical filters corresponding to the groups having a range of attenuation, including no optical filter and/or a "clear" filter having negligible attenuation.

As shown in FIGS. 11A-C, a filtering media may be advantageously added to an encapsulant that functions both as a cover to protect LEDs and bonding wires and as an optical filter 1100. In one embodiment, a filtering media 1100 encapsulates a select group of LEDs and a clear media 600 (FIG. 6) encapsulates the entire array 700 and the filtering media 1000 (FIG. 6). In a particular embodiment, corresponding to TABLE 1, above, five LEDs nominally emitting at 660-905 nm are encapsulated with both a filtering media 1100 and an overlying clear media 600 (FIG. 6), i.e. attenuated. In a particular embodiment, the filtering media 1100 is a 40:1 mixture of a clear encapsulant (EPO-TEK OG147-7) and an opaque encapsulate (EPO-TEK OG147) both available from Epoxy Technology, Inc., Billerica, Mass. Three LEDs nominally emitting at 610-630 nm are only encapsulated with the clear media 600 (FIG. 6), i.e. unattenuated. In alternative embodiments, individual LEDs may be singly or multiply encapsulated according to tissue absorption and/or output intensity. In other alternative embodiments, filtering media may be separately attachable optical filters or a combination of encapsulants and separately attachable optical filters. In a particular embodiment, the emitter assembly 500 has one or more notches along each side proximate the component end 1305 (FIG. 13) for retaining one or more clip-on optical filters.

Substrate

Figure 12:
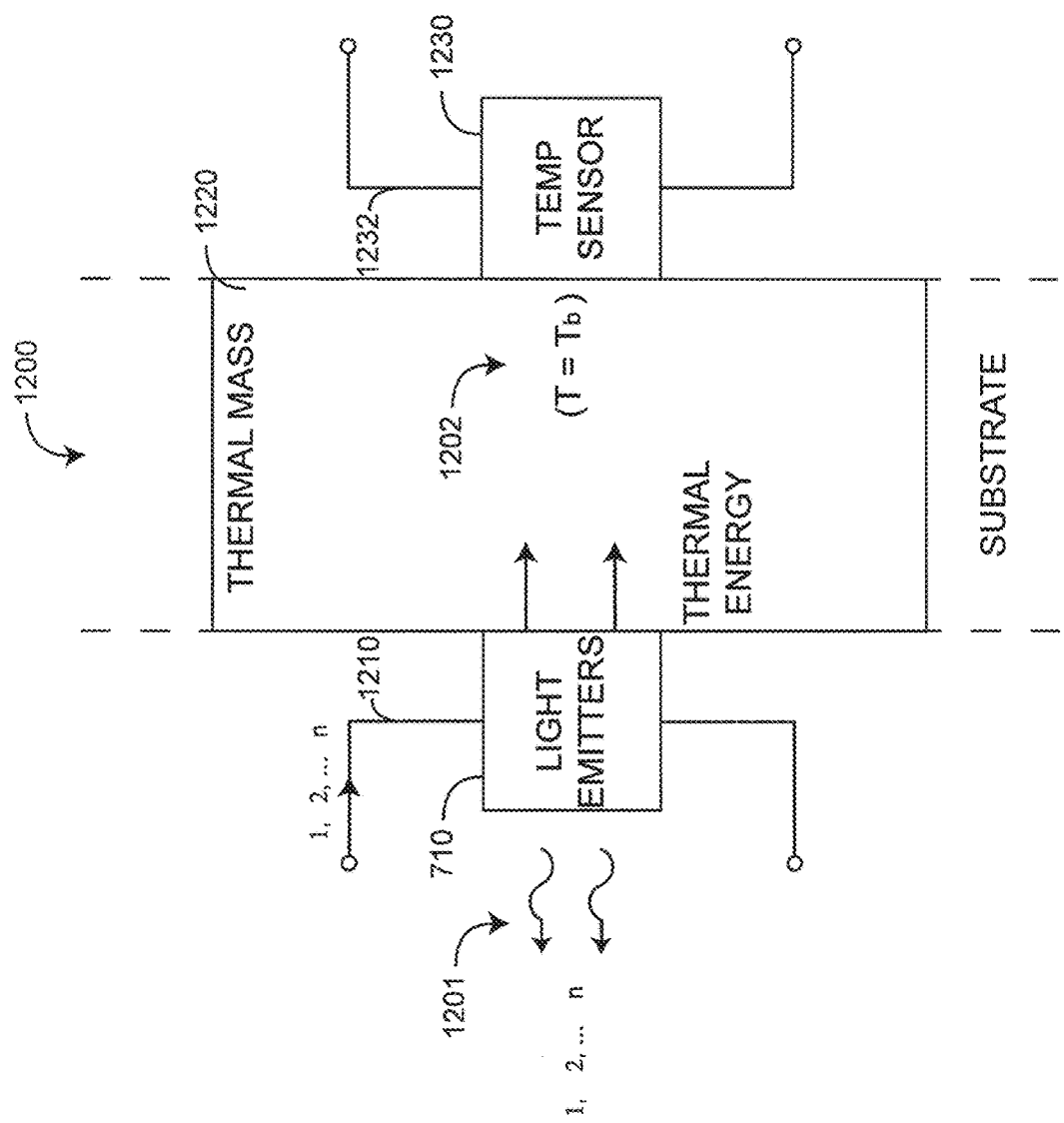
FIG. 12 is a general block diagram of an emitter substrate.

FIG. 12 illustrates light emitters 710 configured to transmit optical radiation 1201 having multiple wavelengths in response to corresponding drive currents 1210. A thermal mass 1220 is disposed proximate the emitters 710 so as to stabilize a bulk temperature 1202 for the emitters. A temperature sensor 1230 is thermally coupled to the thermal mass 1220, wherein the temperature sensor 1230 provides a temperature sensor output 1232 responsive to the bulk temperature 1202 so that the wavelengths are determinable as a function of the drive currents 1210 and the bulk temperature 1202.

In one embodiment, an operating wavelength $\lambda_a$ of each light emitter 710 is determined according to EQ. 3

$$\lambda_a = f(T_b, I_{drive}, \Sigma I_{drive}) \quad (3)$$

where $T_b$ is the bulk temperature, $I_{drive}$ is the drive current for a particular light emitter, as determined by the sensor controller 4500 (FIG. 45), described below, and $\Sigma I_{drive}$ is the total drive current for all light emitters. In another embodiment, temperature sensors are configured to measure the temperature of each light emitter 710 and an operating wavelength $\lambda_a$ of each light emitter 710 is determined according to EQ. 4

$$\lambda_a = f(T_a, I_{drive}, \Sigma I_{drive}) \quad (4)$$

where $T_a$ is the temperature of a particular light emitter, $I_{drive}$ is the drive current for that light emitter and $\Sigma I_{drive}$ is the total drive current for all light emitters.

In yet another embodiment, an operating wavelength for each light emitter is determined by measuring the junction voltage for each light emitter 710. In a further embodiment, the temperature of each light emitter 710 is controlled, such as by one or more Peltier cells coupled to each light emitter 710, and an operating wavelength for each light emitter 710 is determined as a function of the resulting controlled temperature or temperatures. In other embodiments, the operating wavelength for each light emitter 710 is determined directly, for example by attaching a charge coupled device (CCD) to each light emitter or by attaching a fiberoptic to each light emitter and coupling the fiberoptics to a wavelength measuring device, to name a few.

Figure 13:
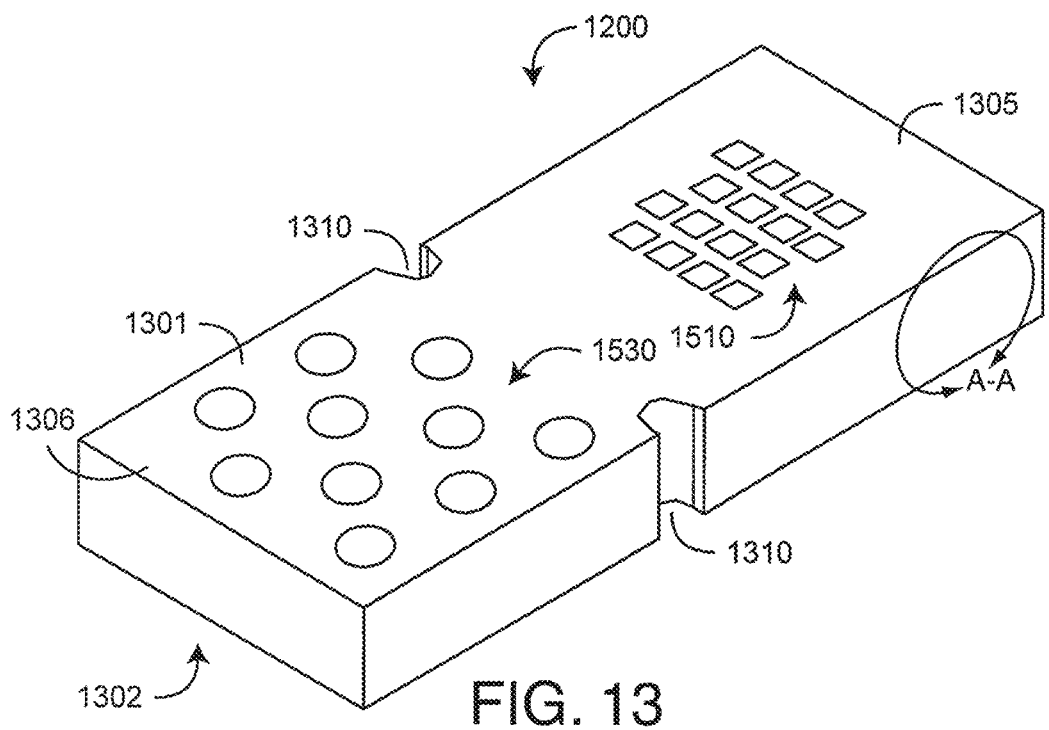
FIGS. 13-14 are top and detailed side views of an emitter substrate embodiment.
Figure 14:
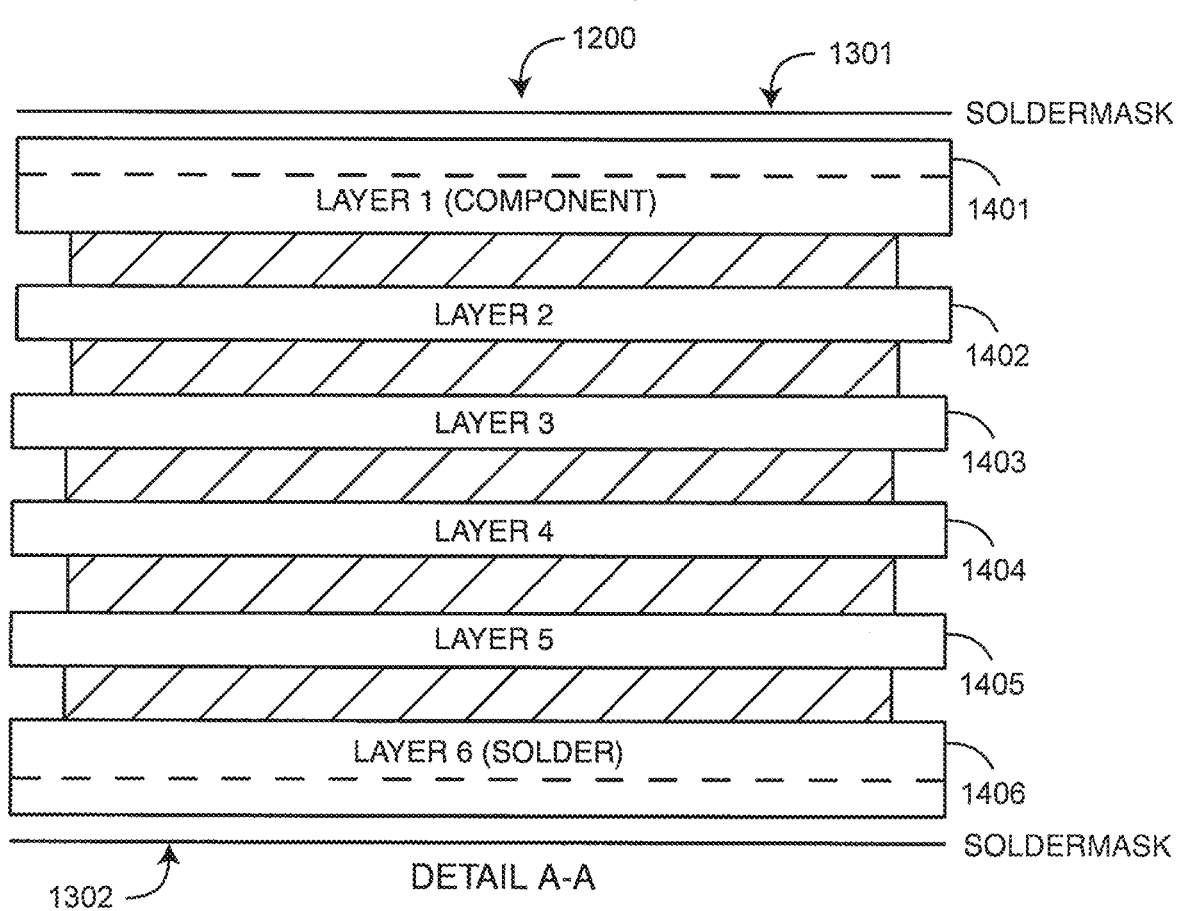
Figures 15, 16:
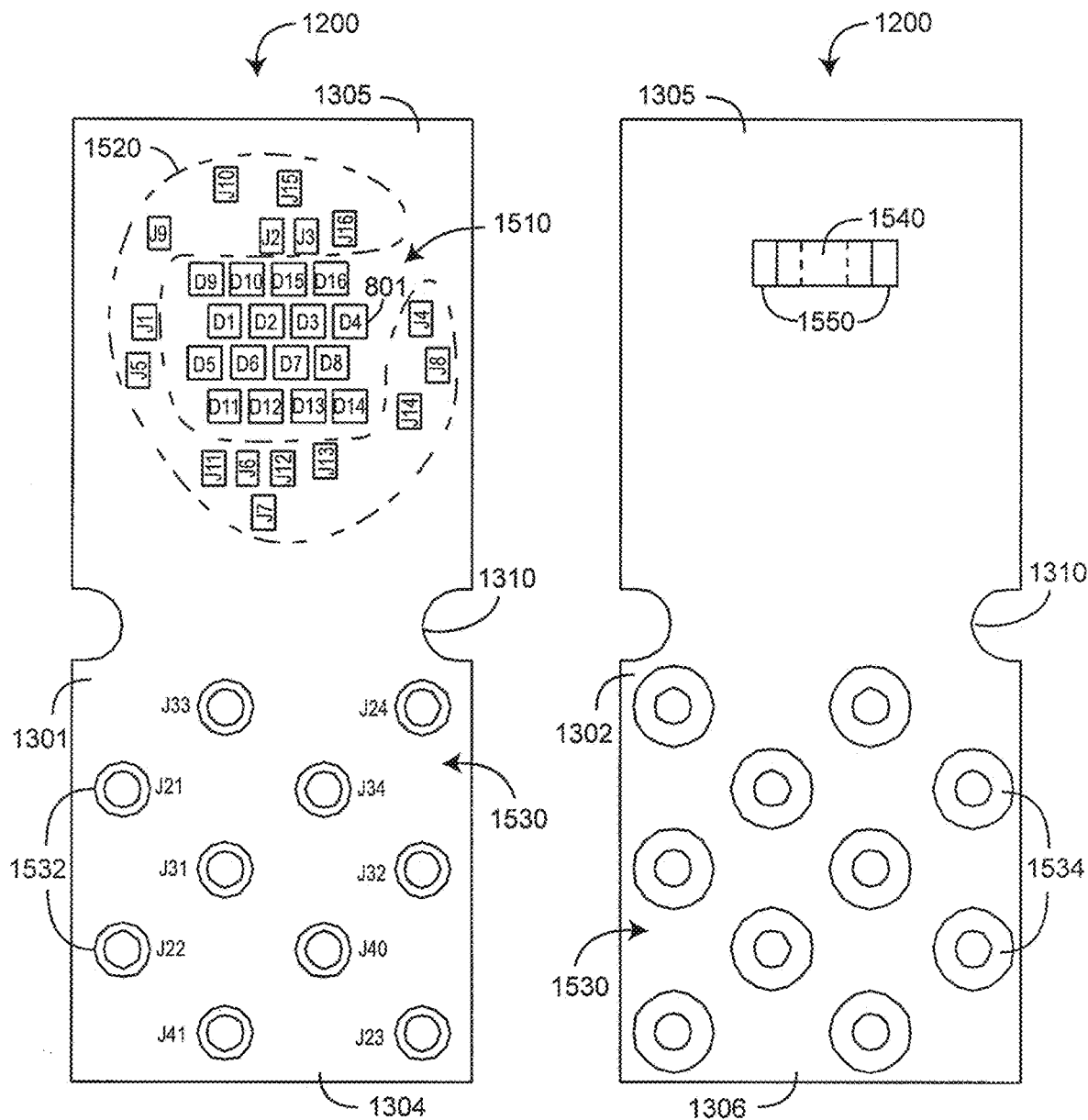
FIG. 15-16 are top and bottom component layout views of an emitter substrate embodiment.

FIGS. 13-18 illustrate one embodiment of a substrate 1200 configured to provide thermal conductivity between an emitter array 700 (FIG. 8) and a thermistor 1540 (FIG. 16). In this manner, the resistance of the thermistor 1540 (FIG. 16) can be measured in order to determine the bulk temperature of LEDs 801 (FIG. 8) mounted on the substrate 1200. The substrate 1200 is also configured with a relatively significant thermal mass, which stabilizes and normalizes the bulk temperature so that the thermistor measurement of bulk temperature is meaningful.

FIGS. 13-14 illustrate a substrate 1200 having a component side 1301, a solder side 1302, a component end 1305 and a connector end 1306. Alignment notches 1310 are disposed between the ends 1305, 1306. The substrate 1200 further has a component layer 1401, inner layers 1402-1405 and a solder layer 1406. The inner layers 1402-1405, e.g. inner layer 1402 (FIG. 18), have substantial metallized areas 1411 that provide a thermal mass 1220 (FIG. 12) to stabilize a bulk temperature for the emitter array 700 (FIG. 12). The metallized areas 1411 also function to interconnect component pads 1510 and wire bond pads 1520 (FIG. 15) to the connector 1530.

Figure 22:
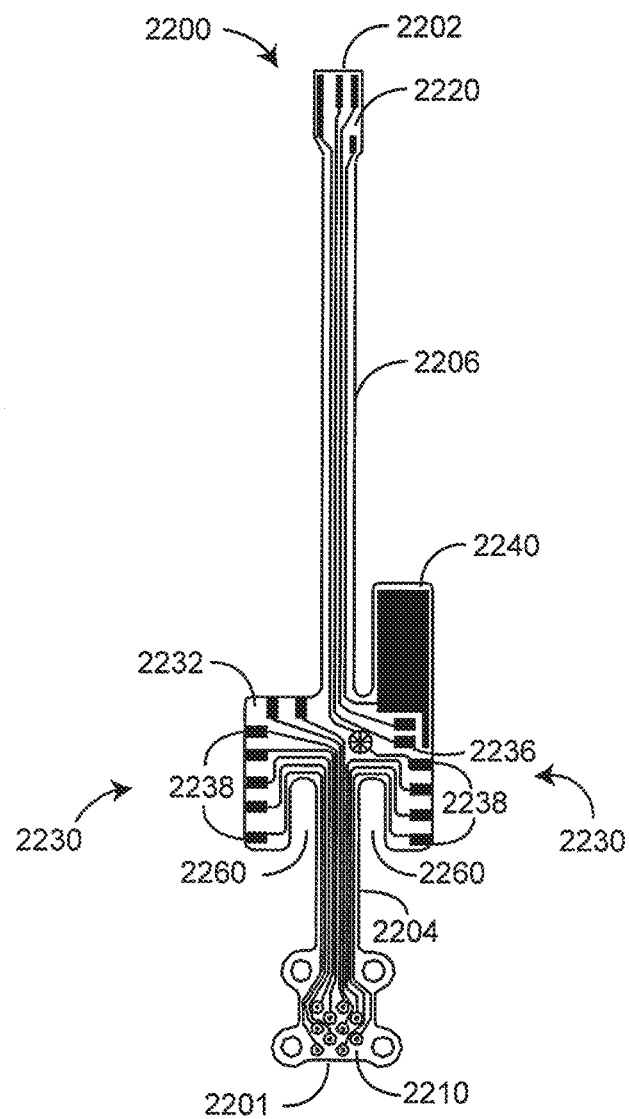
FIG. 22 is a top plan view of a flex circuit.

FIGS. 15-16 illustrate a substrate 1200 having component pads 1510 and wire bond pads 1520 at a component end 1305. The component pads 1510 mount and electrically connect a first side (anode or cathode) of the LEDs 801 (FIG. 8) to the substrate 1200. Wire bond pads 1520 electrically connect a second side (cathode or anode) of the LEDs 801 (FIG. 8) to the substrate 1200. The connector end 1306 has a connector 1530 with connector pads 1532, 1534 that mount and electrically connect the emitter assembly 500 (FIG. 23), including the substrate 1200, to the flex circuit 2200 (FIG. 22). Substrate layers 1401-1406 (FIG. 14) have traces that electrically connect the component pads 1510 and wire bond pads 1520 to the connector 1532-1534. A thermistor 1540 is mounted to thermistor pads 1550 at the component end 1305, which are also electrically connected with traces to the connector 1530. Plated thru holes electrically connect the connector pads 1532, 1534 on the component and solder sides 1301, 1302, respectively.

Figure 17:
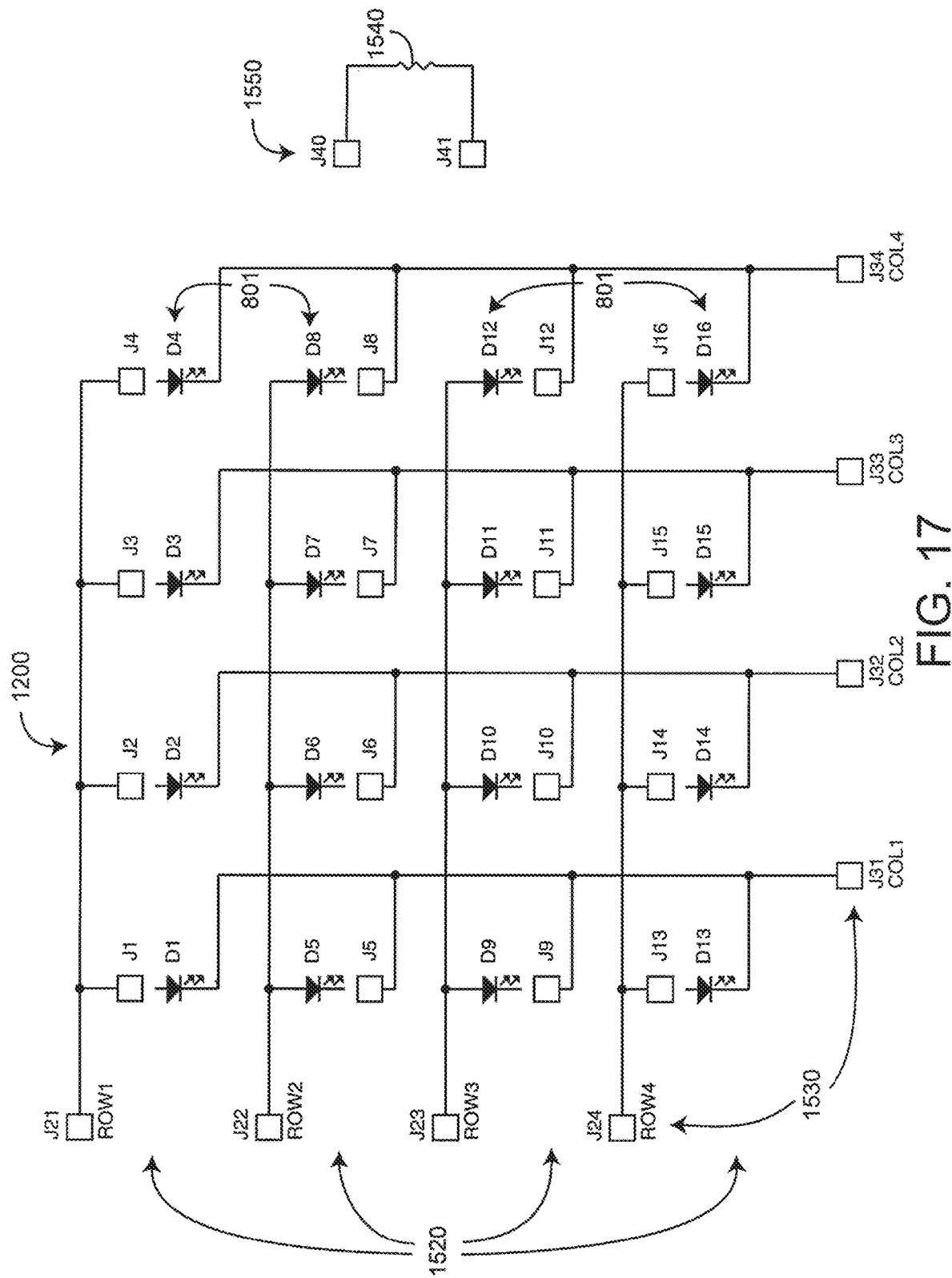
FIG. 17 is a schematic diagram of an emitter substrate embodiment.
Figure 18:
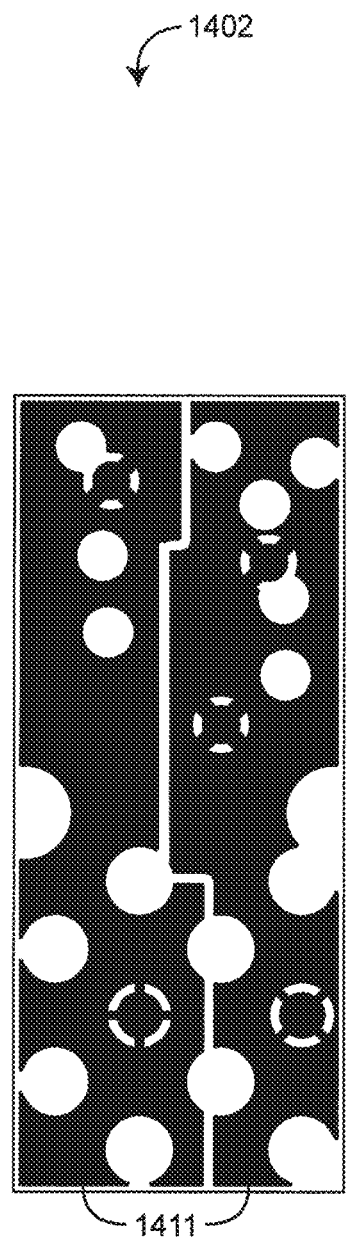
FIG. 18 is a plan view of an inner layer of an emitter substrate embodiment.

FIG. 17 illustrates the electrical layout of a substrate 1200. A portion of the LEDs 801, including D1-D4 and D13-D16 have cathodes physically and electrically connected to component pads 1510 (FIG. 15) and corresponding anodes wire bonded to wire bond pads 1520. Another portion of the LEDs 801, including D5-D8 and D9-D12, have anodes physically and electrically connected to component pads 1510 (FIG. 15) and corresponding cathodes wire bonded to wire bond pads 1520. The connector 1530 has row pinouts J21-J24, column pinouts J31-J34 and thermistor pinouts J40-J41 for the LEDs 801 and thermistor 1540.

Interconnect Assembly

Figure 19:
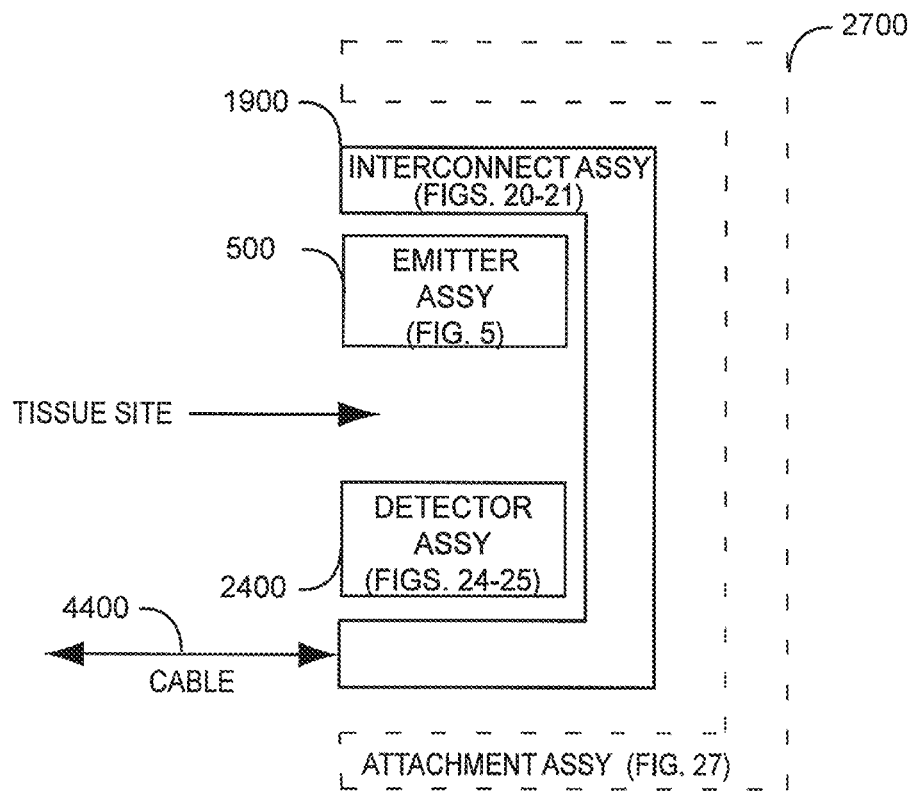
FIG. 19 is a general block diagram of an interconnect assembly in relationship to other sensor assemblies.

FIG. 19 illustrates an interconnect assembly 1900 that mounts the emitter assembly 500 and detector assembly 2400, connects to the sensor cable 4400 and provides electrical communications between the cable and each of the emitter assembly 500 and detector assembly 2400. In one embodiment, the interconnect assembly 1900 is incorporated with the attachment assembly 2700, which holds the emitter and detector assemblies to a tissue site. An interconnect assembly embodiment utilizing a flexible (flex) circuit is described with respect to FIGS. 20-24, below.

Figure 20:
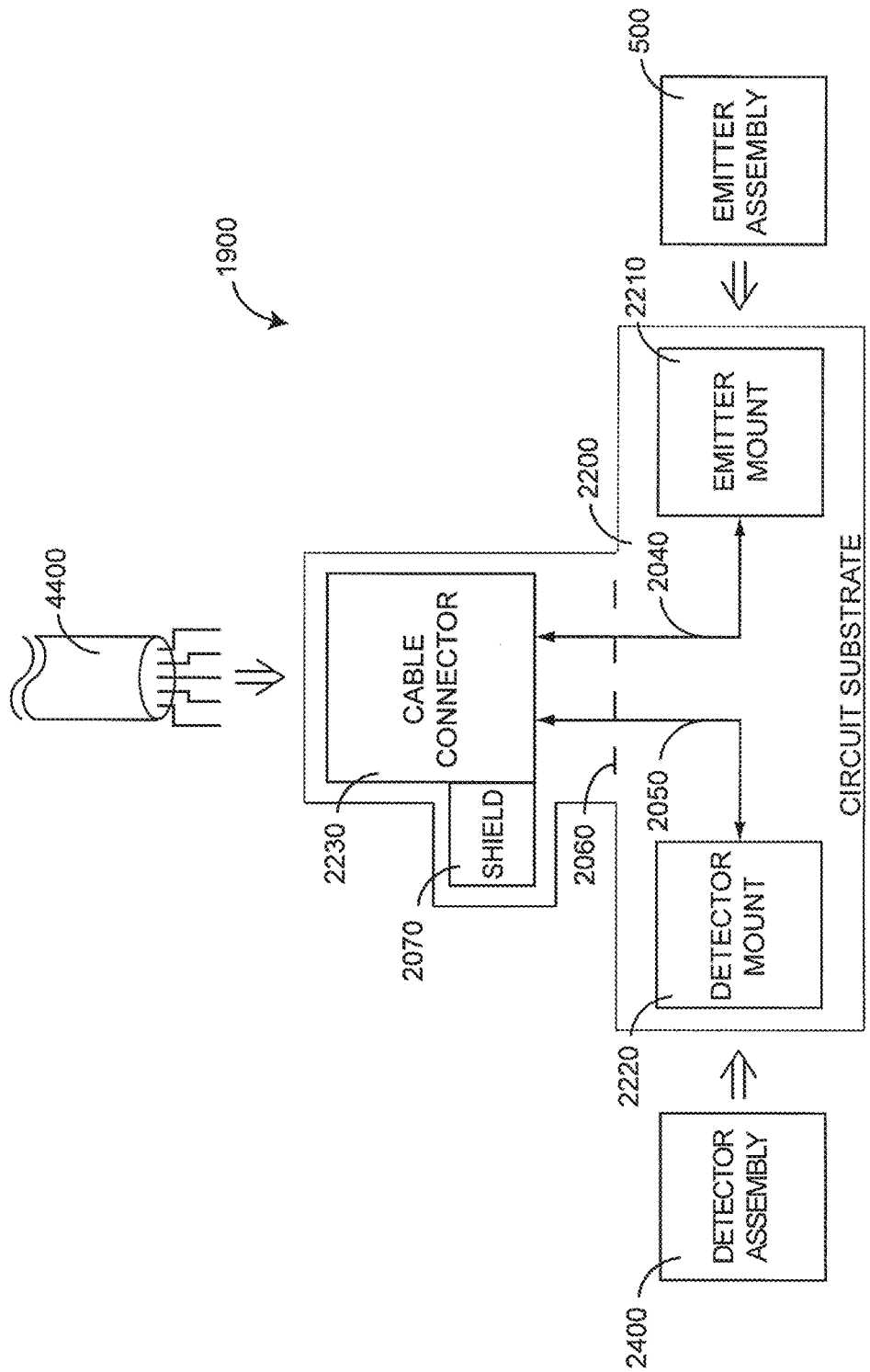
FIG. 20 is a block diagram of an interconnect assembly embodiment.

FIG. 20 illustrates an interconnect assembly 1900 embodiment having a circuit substrate 2200, an emitter mount 2210, a detector mount 2220 and a cable connector 2230. The emitter mount 2210, detector mount 2220 and cable connector 2230 are disposed on the circuit substrate 2200. The emitter mount 2210 is adapted to mount an emitter assembly 500 having multiple emitters. The detector mount 2220 is adapted to mount a detector assembly 2400 having a detector. The cable connector 2230 is adapted to attach a sensor cable 4400. A first plurality of conductors 2040 disposed on the circuit substrate 2200 electrically interconnects the emitter mount 2210 and the cable connector 2230. A second plurality of conductors 2050 disposed on the circuit substrate 2200 electrically interconnects the detector mount 2220 and the cable connector 2230. A decoupling 2060 disposed proximate the cable connector 2230 substantially mechanically isolates the cable connector 2230 from both the emitter mount 2210 and the detector mount 2220 so that sensor cable stiffness is not translated to the emitter assembly 500 or the detector assembly 2400. A shield 2070 is adapted to fold over and shield one or more wires or pairs of wires of the sensor cable 4400.

Figure 21:
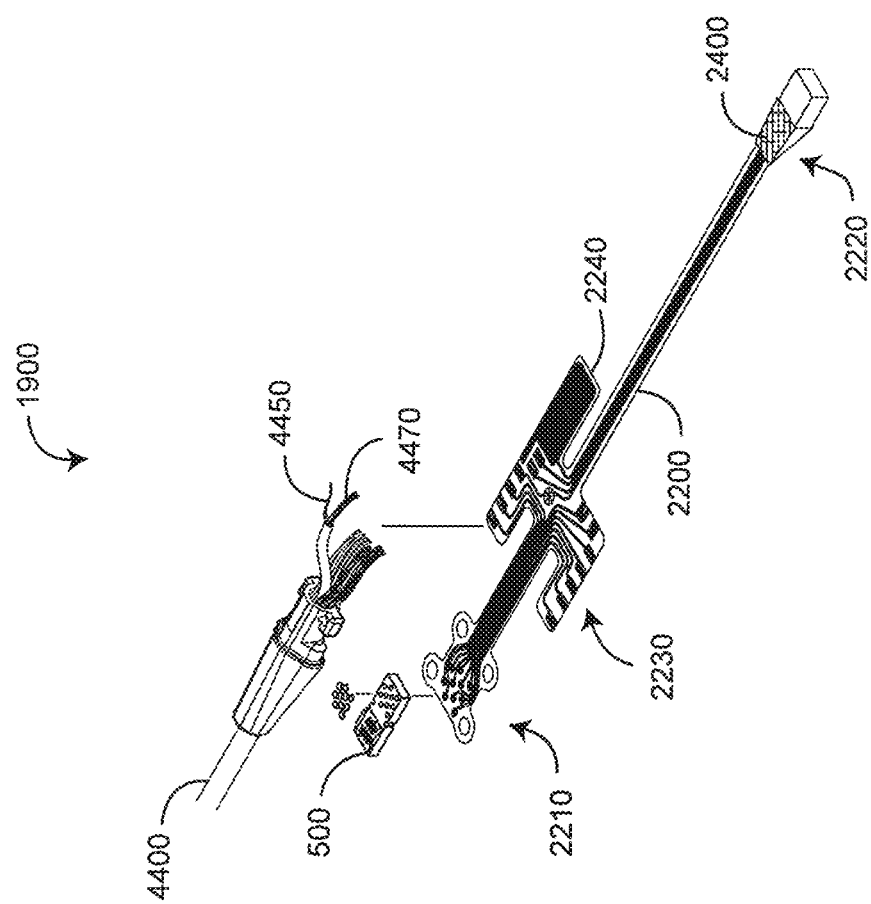
FIG. 21 is a partially-exploded perspective view of a flex circuit assembly embodiment of an interconnect assembly.

FIG. 21 illustrates a flex circuit assembly 1900 having a flex circuit 2200, an emitter assembly 500 and a detector assembly 2400, which is configured to terminate the sensor end of a sensor cable 4400. The flex circuit assembly 1900 advantageously provides a structure that electrically connects yet mechanically isolates the sensor cable 4400, the emitter assembly 500 and the detector assembly 2400. As a result, the mechanical stiffness of the sensor cable 4400 is not translated to the sensor pads 3000, 3100 (FIGS. 30-31), allowing a comfortable finger attachment for the sensor 200 (FIG. 1). In particular, the emitter assembly 500 and detector assembly 2400 are mounted to opposite ends 2201, 2202 (FIG. 22) of an elongated flex circuit 2200. The sensor cable 4400 is mounted to a cable connector 2230 extending from a middle portion of the flex circuit 2200. Detector wires 4470 are shielded at the flex circuit junction by a fold-over conductive ink flap 2240, which is connected to a cable inner shield 4450. The flex circuit 2200 is described in further detail with respect to FIG. 22. The emitter portion of the flex circuit assembly 1900 is described in further detail with respect to FIG. 23. The detector assembly 2400 is described with respect to FIG. 24. The sensor cable 4400 is described with respect to FIGS. 44A-B, below.

Figure 24:
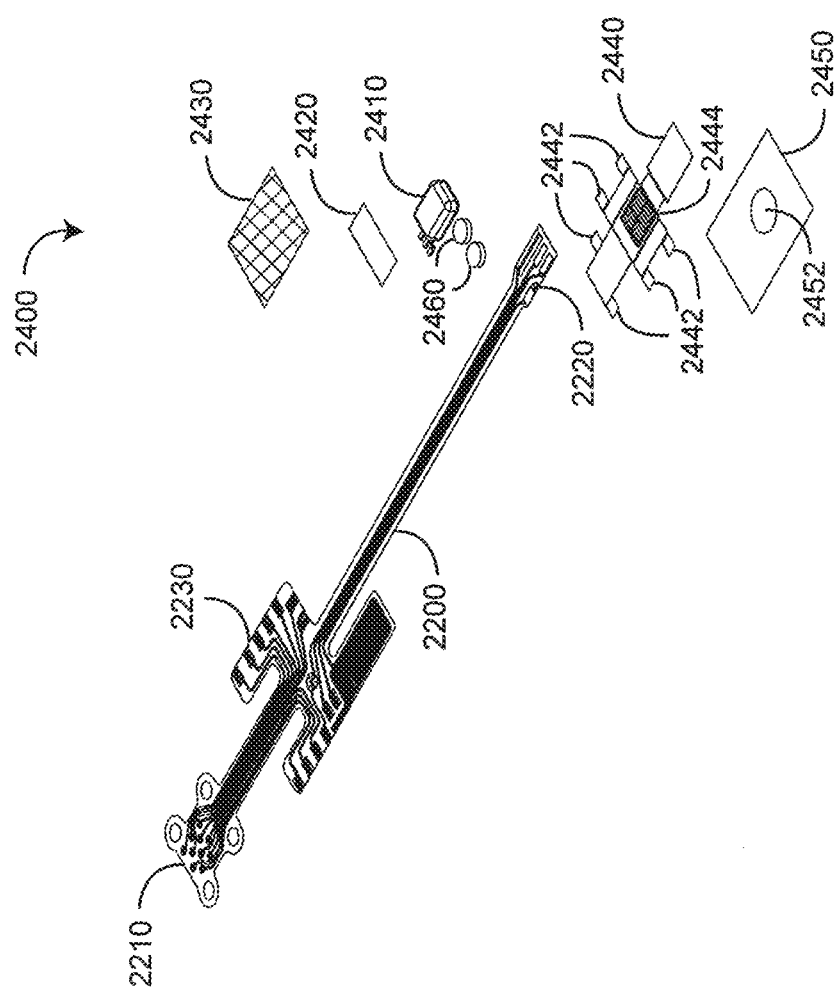
FIG. 24 is an exploded perspective view of a detector assembly embodiment.
Figures 44A, 44B:
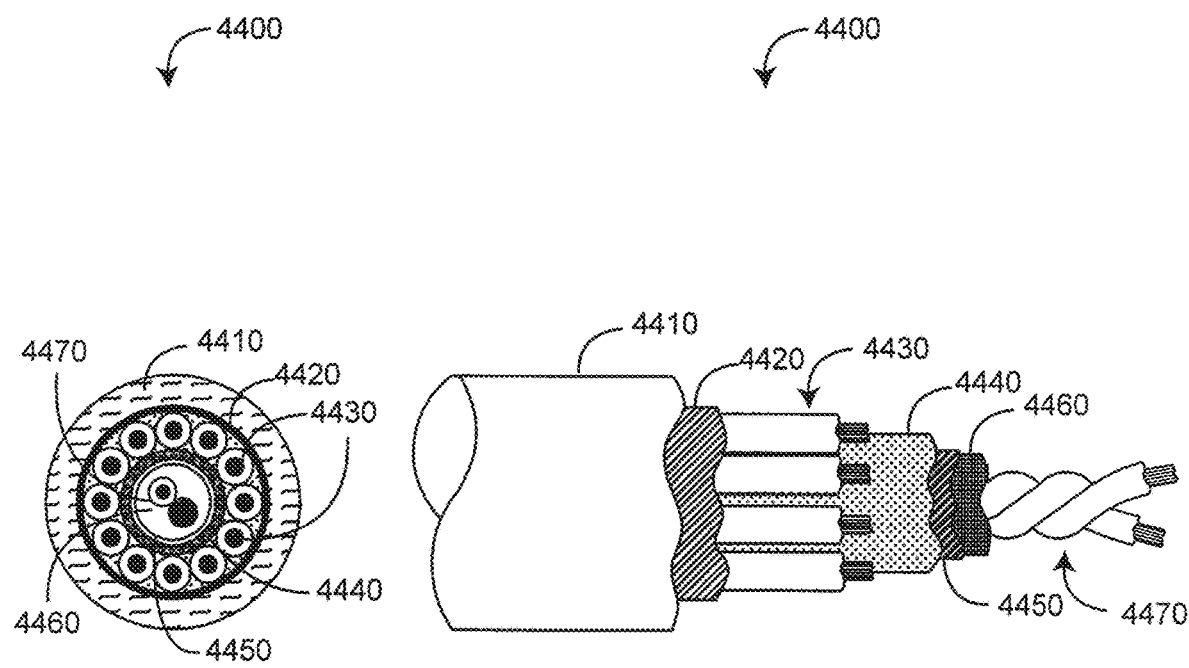
FIGS. 44A-B are cross sectional and side cut away views of a sensor cable.

FIG. 22 illustrates a sensor flex circuit 2200 having an emitter end 2201, a detector end 2202, an elongated interconnect 2204, 2206 between the ends 2201, 2202 and a cable connector 2230 extending from the interconnect 2204, 2206. The emitter end 2201 forms a "head" having emitter solder pads 2210 for attaching the emitter assembly 500 (FIG. 6) and mounting ears 2214 for attaching to the emitter pad 3000 (FIG. 30B), as described below. The detector end 2202 has detector solder pads for attaching the detector 2410 (FIG. 24). The interconnect 2204 between the emitter end 2201 and the cable connector 2230 forms a "neck," and the interconnect 2206 between the detector end 2202 and the cable connector 2230 forms a "tail." The cable connector 2230 forms "wings" that extend from the interconnect 2204, 2206 between the neck 2204 and tail 2206. A conductive ink flap 2240 connects to the cable inner shield 4450 (FIGS. 44A-B) and folds over to shield the detector wires 4470 (FIGS. 44A-B) soldered to the detector wire pads 2236. The outer wire pads 2238 connect to the remaining cable wires 4430 (FIGS. 44A-B). The flex circuit 2200 has top coverlay, top ink, inner coverlay, trace, trace base, bottom ink and bottom coverlay layers.

The flex circuit 2200 advantageously provides a connection between a multiple wire sensor cable 4400 (FIGS. 44A-B), a multiple wavelength emitter assembly 500 (FIG. 6) and a detector assembly 2400 (FIG. 24) without rendering the emitter and detector assemblies unwieldy and stiff. In particular, the wings 2230 provide a relatively large solder pad area 2232 that is narrowed at the neck 2204 and tail 2206 to mechanically isolate the cable 4400 (FIGS. 44A-B) from the remainder of the flex circuit 2200. Further, the neck 2206 is folded (see FIG. 4) for installation in the emitter pad 3000 (FIGS. 30A-H) and acts as a flexible spring to further mechanically isolate the cable 4400 (FIGS. 44A-B) from the emitter assembly 500 (FIG. 4). The tail 2206 provides an integrated connectivity path between the detector assembly 2400 (FIG. 24) mounted in the detector pad 3100 (FIGS. 31A-H) and the cable connector 2230 mounted in the opposite emitter pad 3000 (FIGS. 30A-H).

Figure 23:
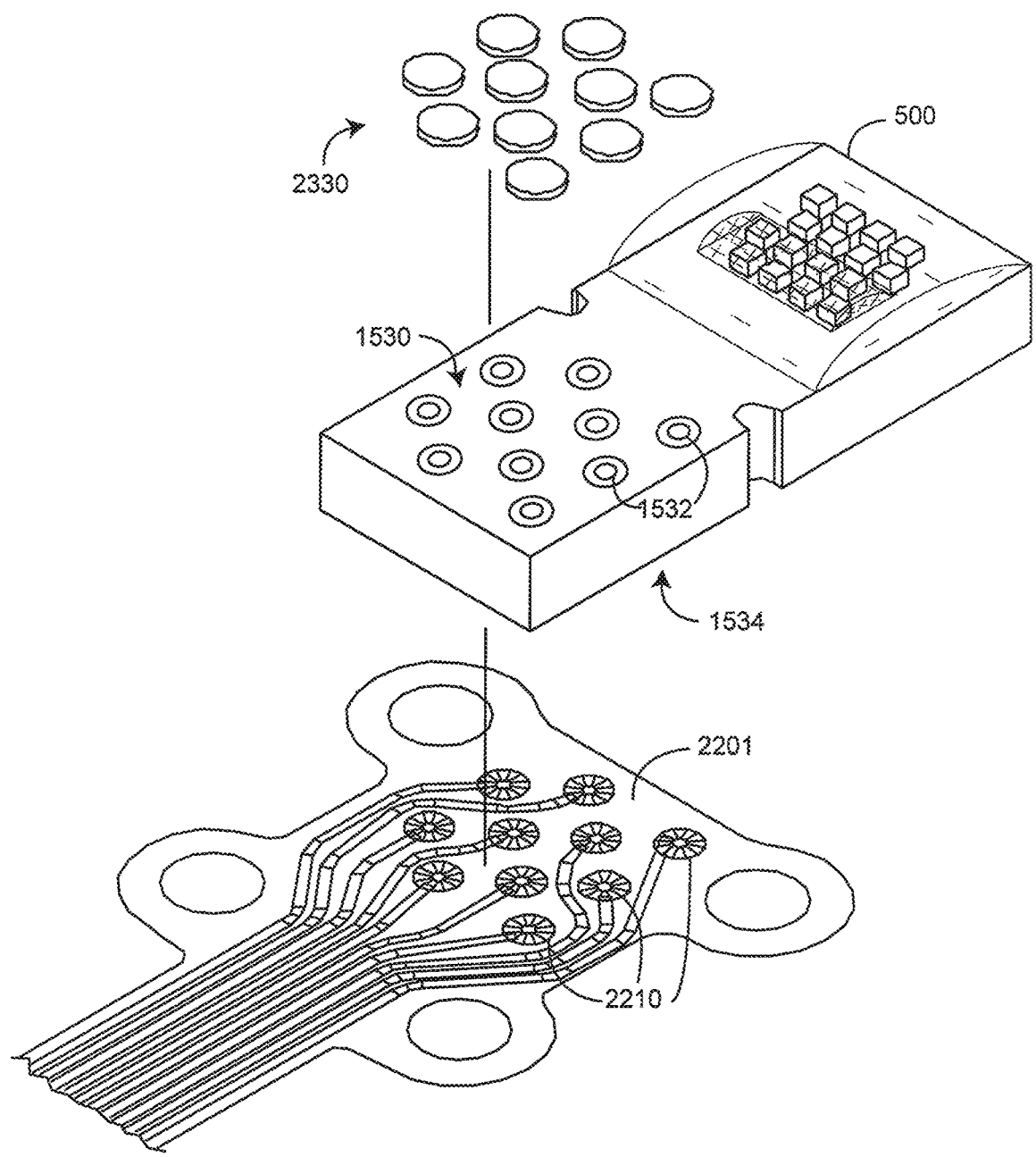
FIG. 23 is an exploded perspective view of an emitter portion of a flex circuit assembly.

FIG. 23 illustrates the emitter portion of the flex circuit assembly 1900 (FIG. 21) having the emitter assembly 500. The emitter assembly connector 1530 is attached to the emitter end 2210 of the flex circuit 2200 (FIG. 22). In particular, reflow solder 2330 connects thru hole pads 1532, 1534 of the emitter assembly 500 to corresponding emitter pads 2310 of the flex circuit 2200 (FIG. 22).

FIG. 24 illustrates a detector assembly 2400 including a detector 2410, solder pads 2420, copper mesh tape 2430, an EMI shield 2440 and foil 2450. The detector 2410 is soldered 2460 chip side down to detector solder pads 2420 of the flex circuit 2200. The detector solder joint and detector ground pads 2420 are wrapped with the Kapton tape 2470. EMI shield tabs 2442 are folded onto the detector pads 2420 and soldered. The EMI shield walls are folded around the detector 2410 and the remaining tabs 2442 are soldered to the back of the EMI shield 2440. The copper mesh tape 2430 is cut to size and the shielded detector and flex circuit solder joint are wrapped with the copper mesh tape 2430. The foil 2450 is cut to size with a predetermined aperture 2452. The foil 2450 is wrapped around shielded detector with the foil side in and the aperture 2452 is aligned with the EMI shield grid 2444.

Detector Assembly

Figure 25:
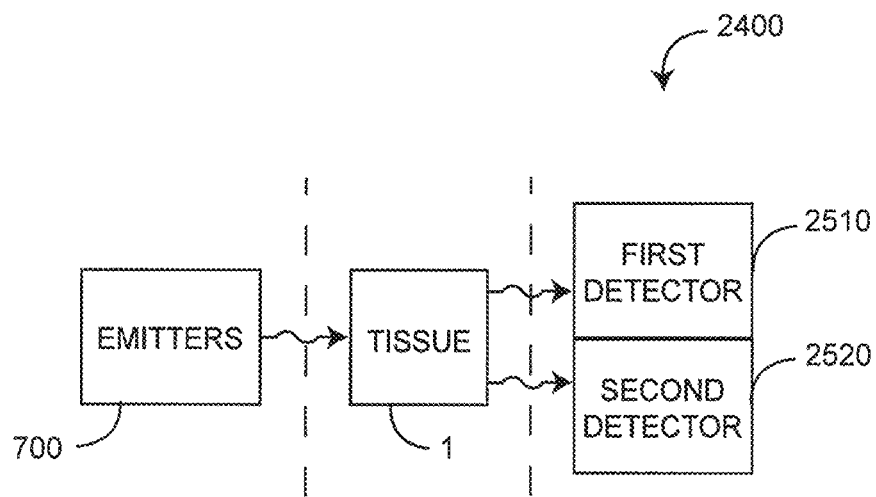
FIGS. 25-26 are block diagrams of adjacent detector and stacked detector embodiments.

FIG. 25 illustrates an alternative detector assembly 2400 embodiment having adjacent detectors. Optical radiation having multiple wavelengths generated by emitters 700 is transmitted into a tissue site 1. Optical radiation at a first set of wavelengths is detected by a first detector 2510, such as, for example, a Si detector. Optical radiation at a second set of wavelengths is detected by a second detector 2520, such as, for example, a GaAs detector.

Figure 26:
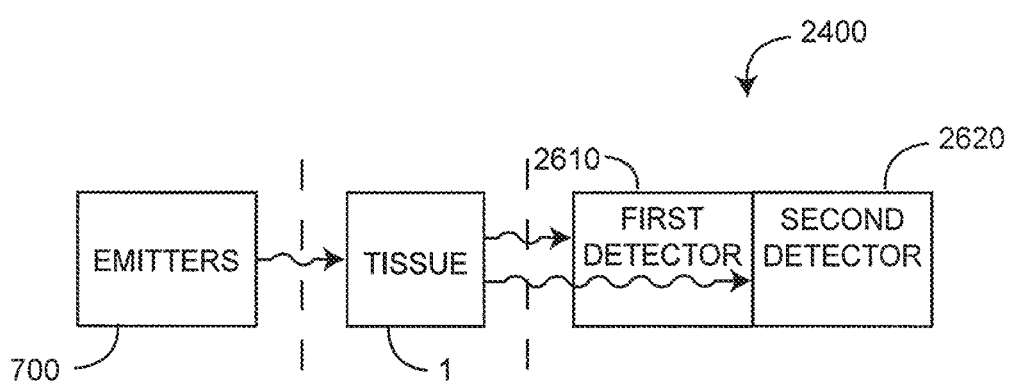

FIG. 26 illustrates another alternative detector assembly 2400 embodiment having stacked detectors coaxial along a light path. Optical radiation having multiple wavelengths generated by emitters 700 is transmitted into a tissue site 1. Optical radiation at a first set of wavelengths is detected by a first detector 2610. Optical radiation at a second set of wavelengths passes through the first detector 2610 and is detected by a second detector 2620. In a particular embodiment, a silicon (Si) detector and a gallium arsenide (GaAs) detector are used. The Si detector is placed on top of the GaAs detector so that light must pass through the Si detector before reaching the GaAs detector. The Si detector can be placed directly on top of the GaAs detector or the Si and GaAs detector can be separated by some other medium, such as a transparent medium or air. In another particular embodiment, a germanium detector is used instead of the GaAs detector. Advantageously, the stacked detector arrangement minimizes error caused by pathlength differences as compared with the adjacent detector embodiment.

Finger Clip

Figure 27:
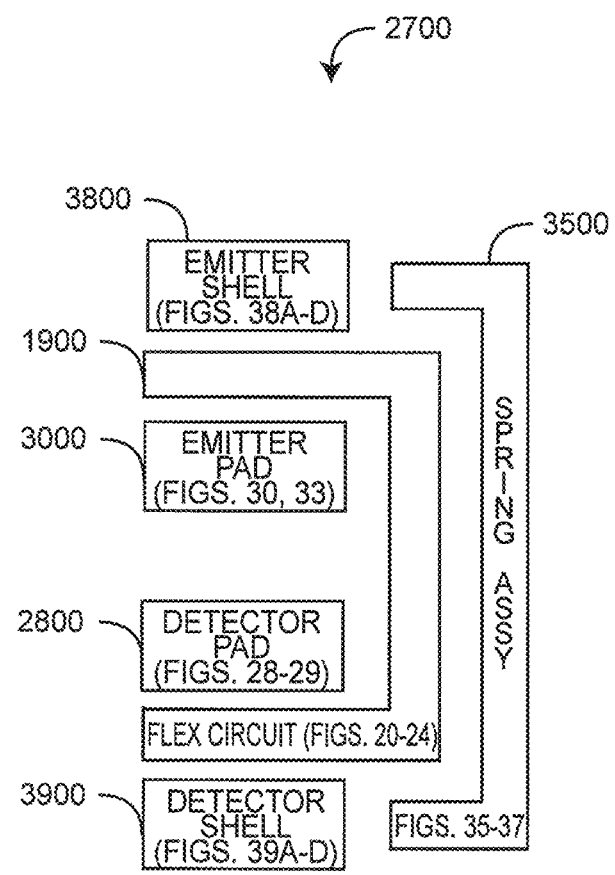
FIG. 27 is a block diagram of a finger clip embodiment of an attachment assembly.

FIG. 27 illustrates a finger clip embodiment 2700 of a physiological sensor attachment assembly. The finger clip 2700 is configured to removably attach an emitter assembly 500 (FIG. 6) and detector assembly 2400 (FIG. 24), interconnected by a flex circuit assembly 1900, to a fingertip. The finger clip 2700 has an emitter shell 3800, an emitter pad 3000, a detector pad 2800 and a detector shell 3900. The emitter shell 3800 and the detector shell 3900 are rotatably connected and urged together by the spring assembly 3500. The emitter pad 3000 is fixedly retained by the emitter shell. The emitter assembly 500 (FIG. 6) is mounted proximate the emitter pad 3000 and adapted to transmit optical radiation having a plurality of wavelengths into fingertip tissue. The detector pad 2800 is fixedly retained by the detector shell 3900. The detector assembly 3500 is mounted proximate the detector pad 2800 and adapted to receive the optical radiation after attenuation by fingertip tissue.

Figure 28:
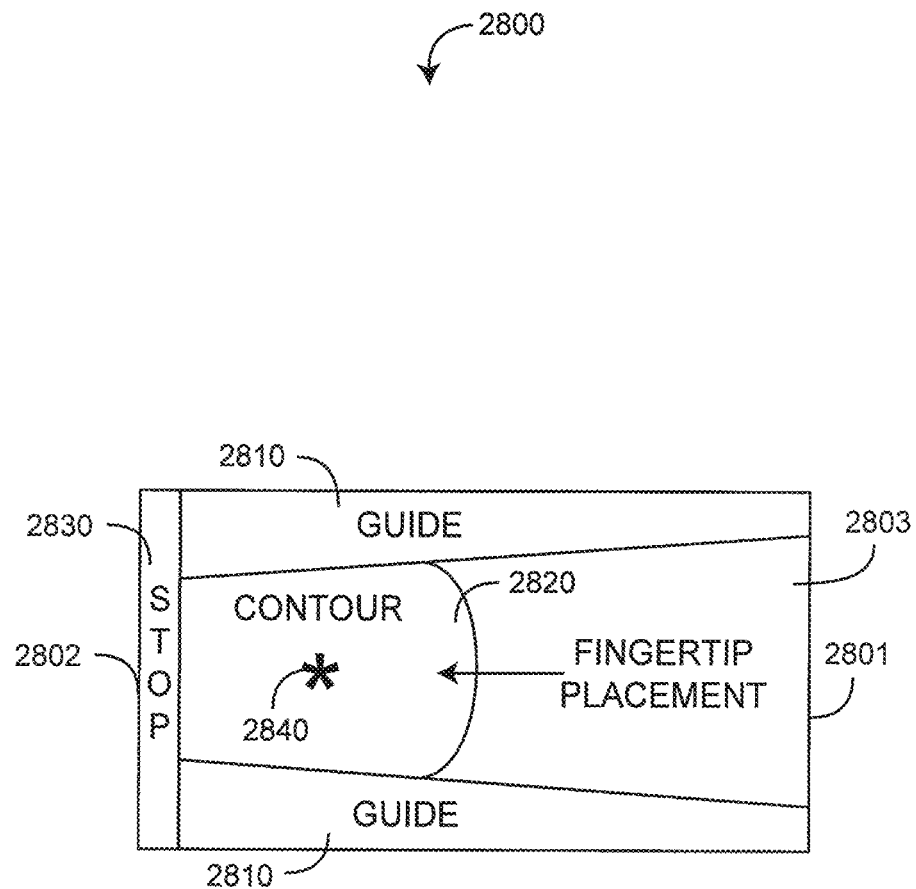
FIG. 28 is a general block diagram of a detector pad.
Figure 29A:
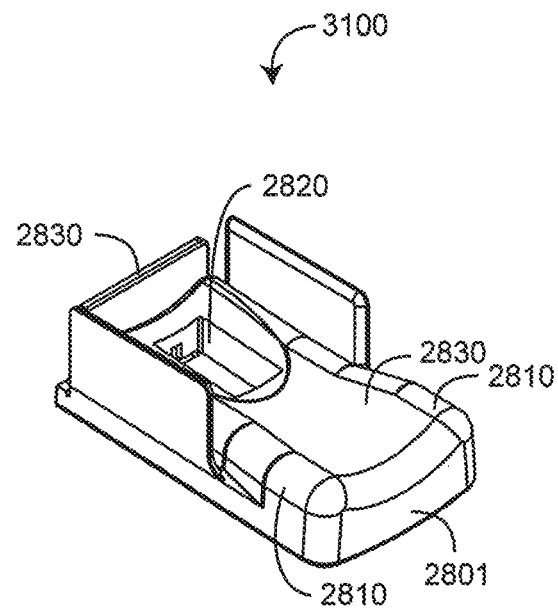
FIGS. 29A-B are perspective views of detector pad embodiments.
Figure 29B:
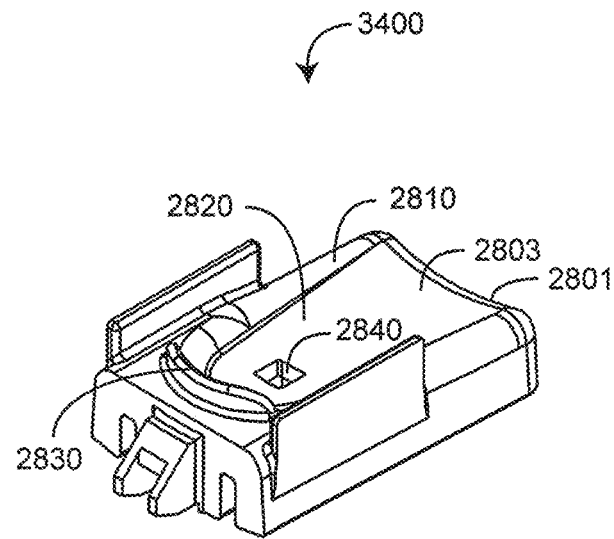
Figure 30A:
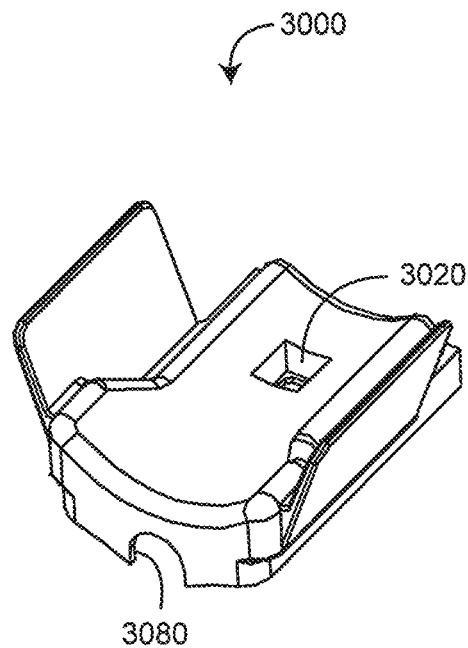
FIGS. 30A-H are perspective bottom, perspective top, bottom, back, top, side cross sectional, side, and front cross sectional views of an emitter pad embodiment.
Figure 30B:
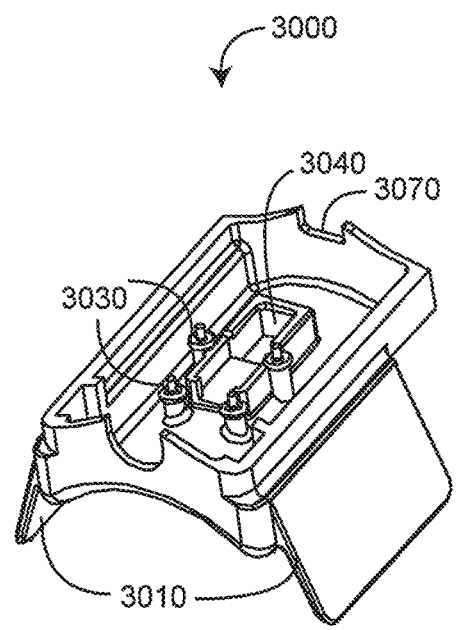
Figure 30C:
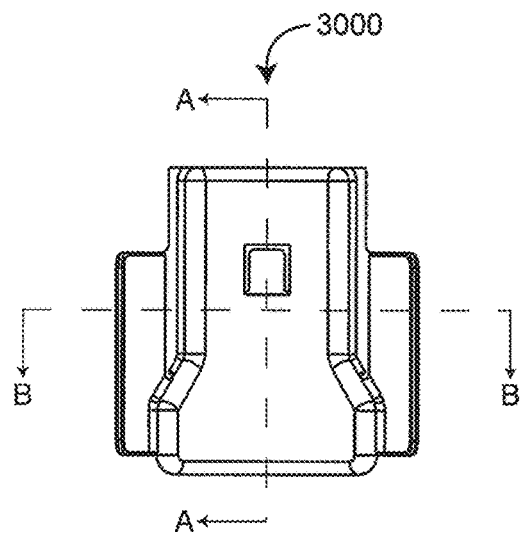
Figure 30F:
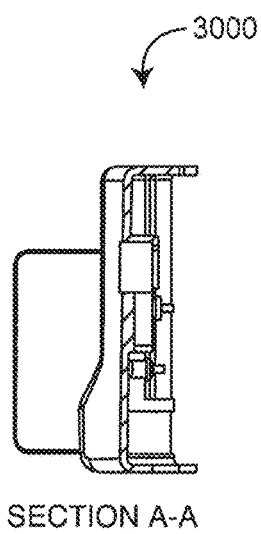
Figure 30D:
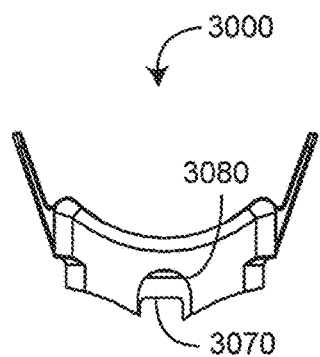
Figure 30G:
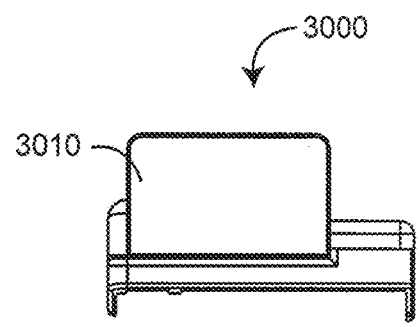
Figure 30E:
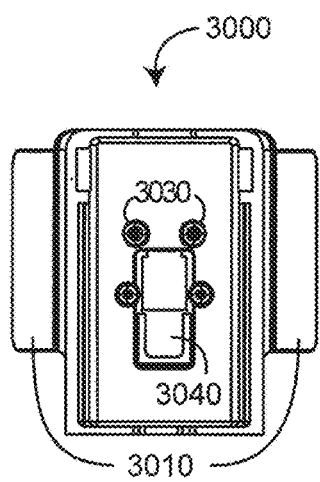
Figure 30H:
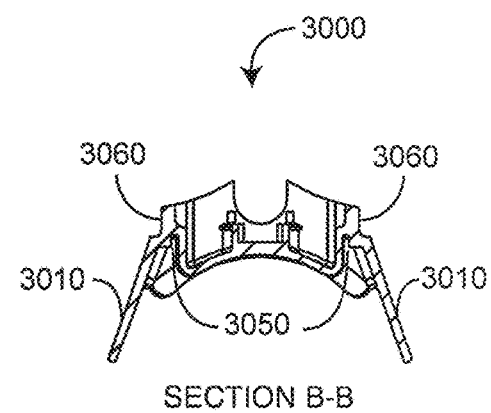
Figure 31A:
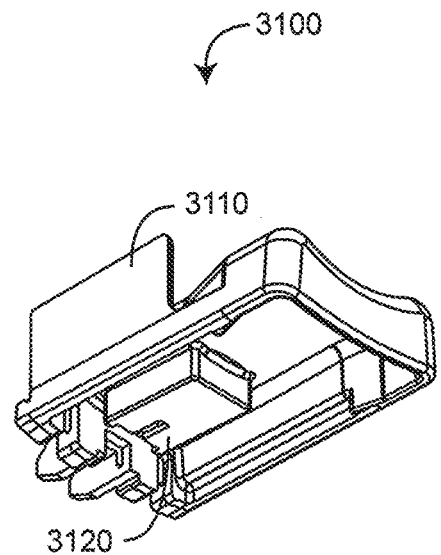
FIGS. 31A-H are perspective bottom, perspective top, top, back, bottom, side cross sectional, side, and front cross sectional views of a detector pad embodiment.
Figure 31B:
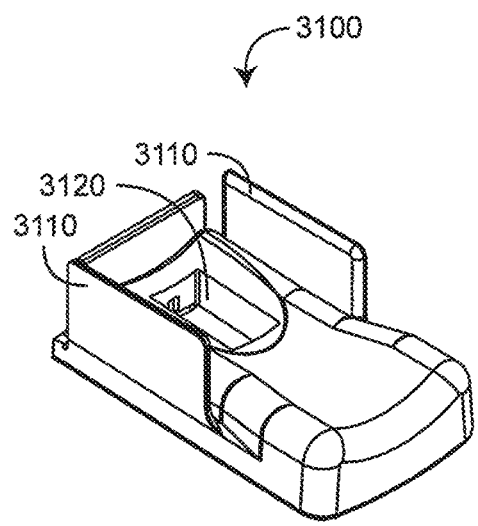
Figure 31C:
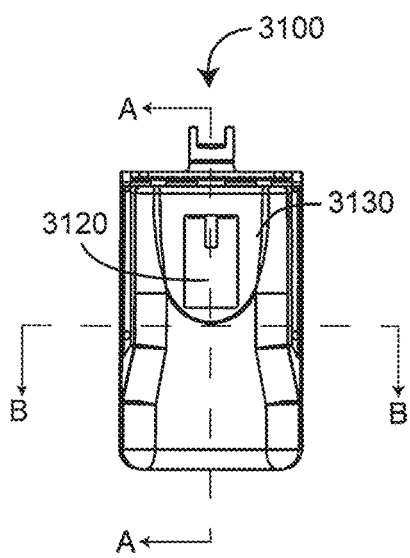
Figure 31F:
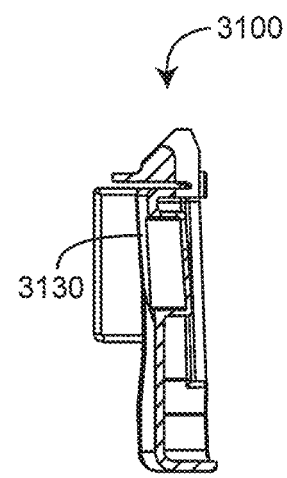
Figure 31D:
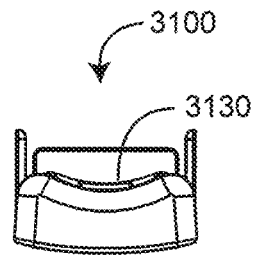
Figure 31G:
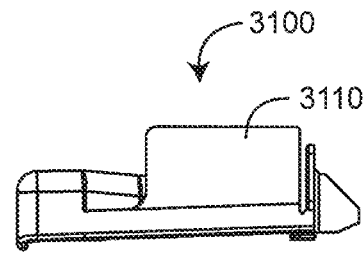
Figure 31E:
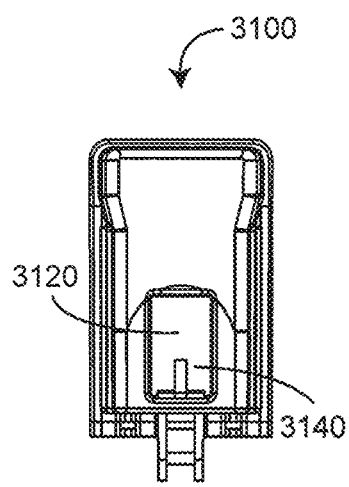
Figure 31H:
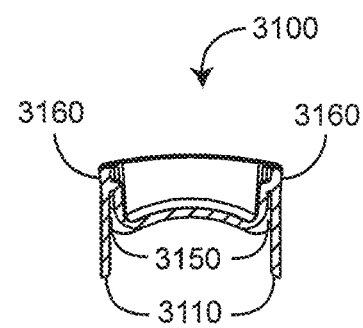
Figure 32A:
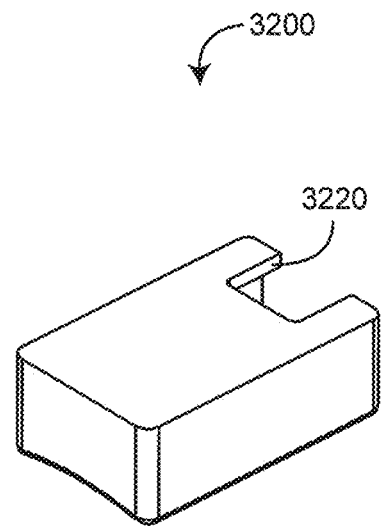
FIGS. 32A-H are perspective bottom, perspective top, top, back, bottom, side cross sectional, side, and front cross sectional views of a shoe box.
Figure 32B:
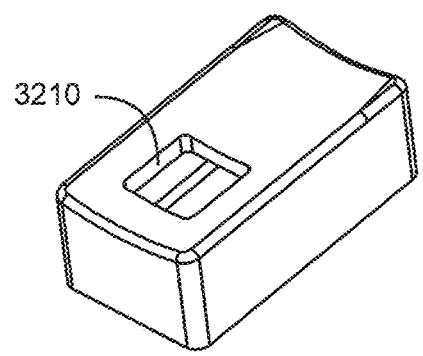
Figure 32C:
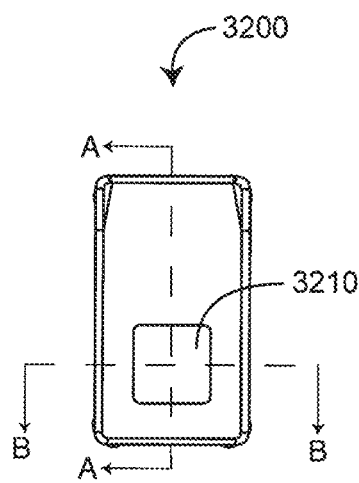
Figure 32F:
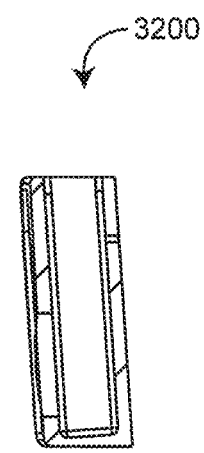
Figure 32D:
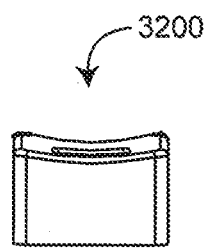
Figure 32G:
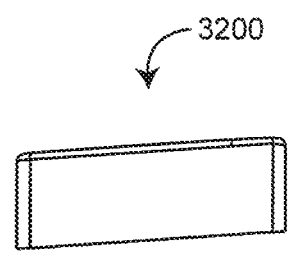
Figure 32E:
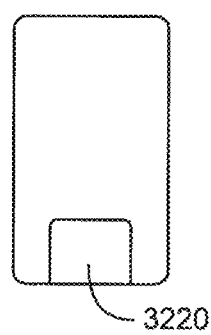
Figure 32H:
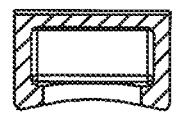
Figure 33A:
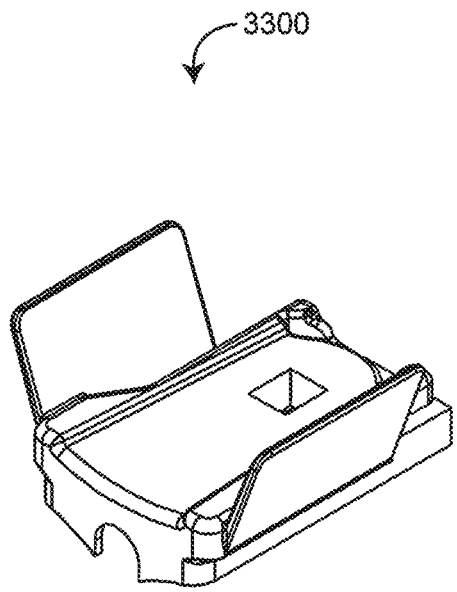
FIGS. 33A-H are perspective bottom, perspective top, top, back, bottom, side cross sectional, side, and front cross sectional views of a slim-finger emitter pad embodiment.
Figure 33B:
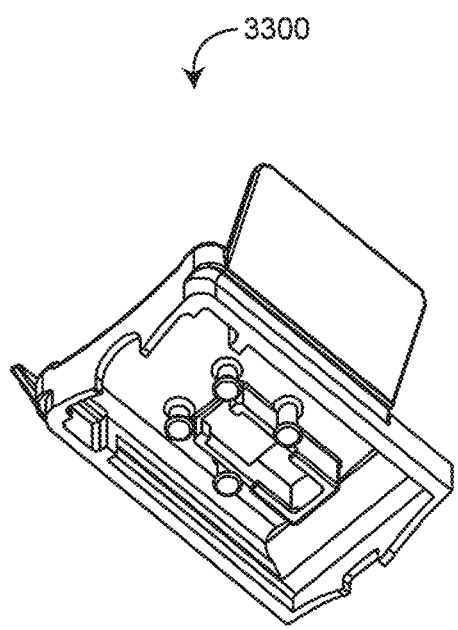
Figure 33C:
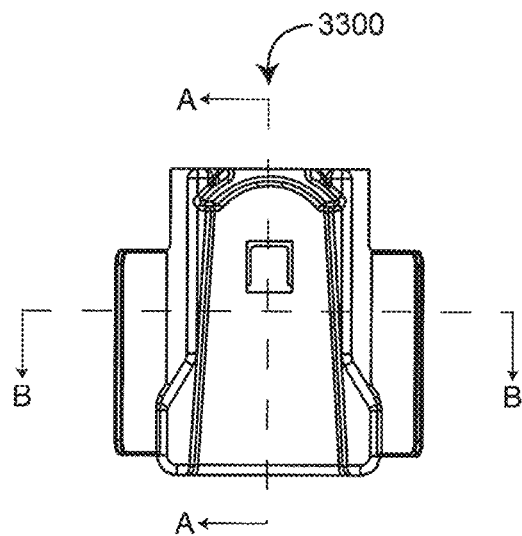
Figure 33F:
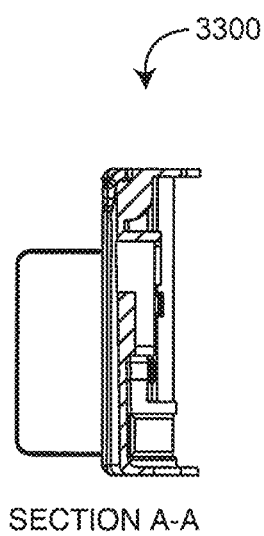
Figure 33D:
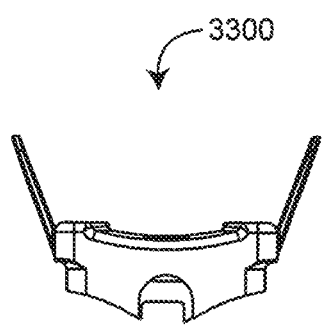
Figure 33G:
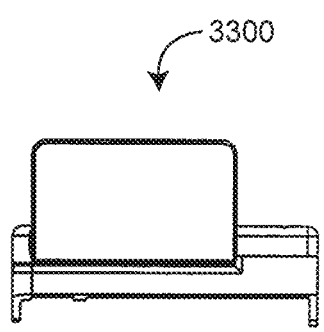
Figure 33E:
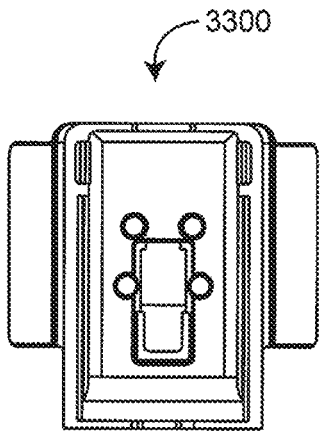
Figure 33H:
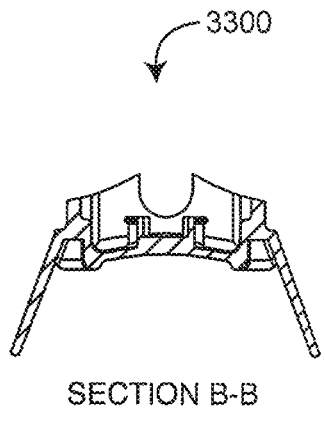
Figure 34A:
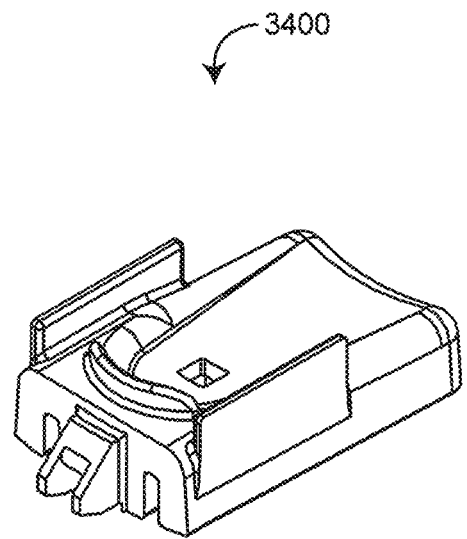
FIGS. 34A-H are perspective bottom, perspective top, top, back, bottom, side cross sectional, side, and front cross sectional views of a slim-finger detector pad embodiment.
Figure 34B:
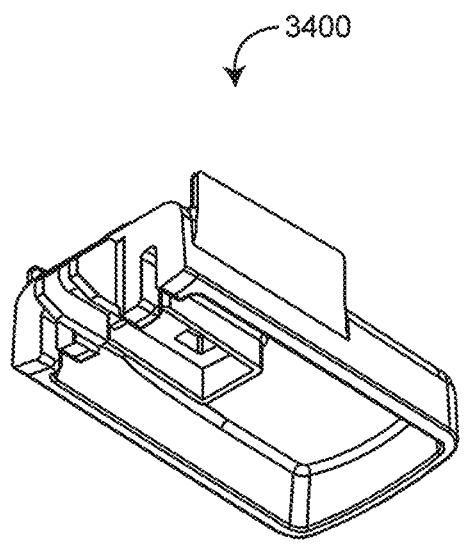
Figure 34C:
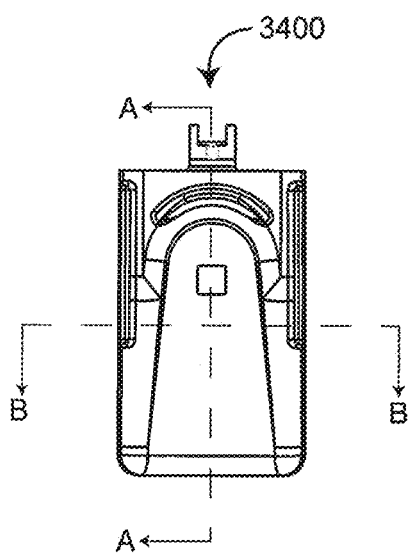
Figure 34D:
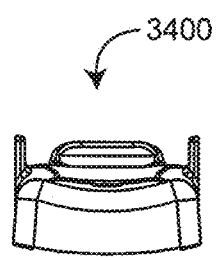
Figure 34E:
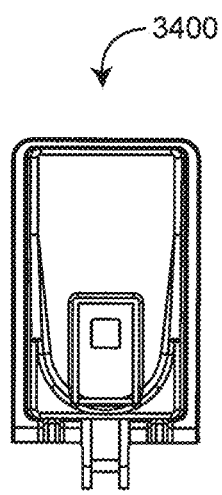
Figure 34F:
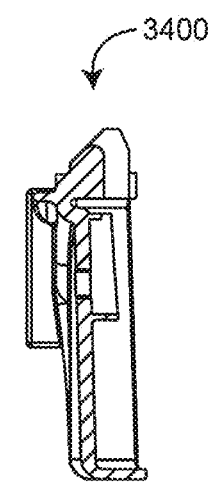
Figure 34G:
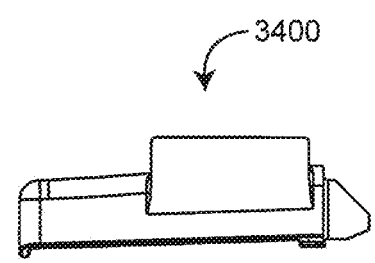
Figure 34H:
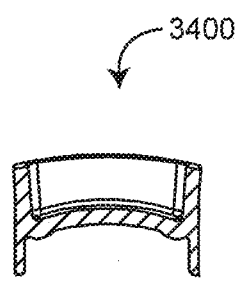

FIG. 28 illustrates a detector pad 2800 advantageously configured to position and comfortably maintain a fingertip relative to a detector assembly for accurate sensor measurements. In particular, the detector pad has fingertip positioning features including a guide 2810, a contour 2820 and a stop 2830. The guide 2810 is raised from the pad surface 2803 and narrows as the guide 2810 extends from a first end 2801 to a second end 2802 so as to increasingly conform to a fingertip as a fingertip is inserted along the pad surface 2803 from the first end 2801. The contour 2820 has an indentation defined along the pad surface 2803 generally shaped to conform to a fingertip positioned over a detector aperture 2840 located within the contour 2820. The stop 2830 is raised from the pad surface 2803 so as to block the end of a finger from inserting beyond the second end 2802. FIGS. 29A-B illustrate detector pad embodiments 3100, 3400 each having a guide 2810, a contour 2820 and a stop 2830, described in further detail with respect to FIGS. 31 and 34, respectively.

FIGS. 30A-H illustrate an emitter pad 3000 having emitter pad flaps 3010, an emitter window 3020, mounting pins 3030, an emitter assembly cavity 3040, isolation notches 3050, a flex circuit notch 3070 and a cable notch 3080. The emitter pad flaps 3010 overlap with detector pad flaps 3110 (FIGS. 31A-H) to block ambient light. The emitter window 3020 provides an optical path from the emitter array 700 (FIG. 8) to a tissue site. The mounting pins 3030 accommodate apertures in the flex circuit mounting ears 2214 (FIG. 22), and the cavity 3040 accommodates the emitter assembly 500 (FIG. 21). Isolation notches 3050 mechanically decouple the shell attachment 3060 from the remainder of the emitter pad 3000. The flex circuit notch 3070 accommodates the flex circuit tail 2206 (FIG. 22) routed to the detector pad 3100 (FIGS. 31A-H). The cable notch 3080 accommodates the sensor cable 4400 (FIGS. 44A-B). FIGS. 33A-H illustrate an alternative slim finger emitter pad 3300 embodiment.

FIGS. 31A-H illustrate a detector pad 3100 having detector pad flaps 3110, a shoe box cavity 3120 and isolation notches 3150. The detector pad flaps 3110 overlap with emitter pad flaps 3010 (FIGS. 30A-H), interleaving to block ambient light. The shoe box cavity 3120 accommodates a shoe box 3200 (FIG. 32A-H) described below. Isolation notches 3150 mechanically decouple the attachment points 3160 from the remainder of the detector pad 3100. FIGS. 34A-H illustrate an alternative slim finger detector pad 3400 embodiment.

FIGS. 32A-H illustrate a shoe box 3200 that accommodates the detector assembly 2400 (FIG. 24). A detector window 3210 provides an optical path from a tissue site to the detector 2410 (FIG. 24). A flex circuit notch 3220 accommodates the flex circuit tail 2206 (FIG. 22) routed from the emitter pad 3000 (FIGS. 30A-H). In one embodiment, the shoe box 3200 is colored black or other substantially light absorbing color and the emitter pad 3000 and detector pad 3100 are each colored white or other substantially light reflecting color.

FIGS. 35-37 illustrate a spring assembly 3500 having a spring 3600 configured to urge together an emitter shell 3800 (FIG. 46) and a detector shell 3900. The detector shell is rotatably connected to the emitter shell. The spring is disposed between the shells 3800, 3900 and adapted to create a pivot point along a finger gripped between the shells that is substantially behind the fingertip. This advantageously allows the shell hinge 3810, 3910 (FIGS. 38-39) to expand so as to distribute finger clip force along the inserted finger, comfortably keeping the fingertip in position over the detector without excessive force.

Figure 36A:
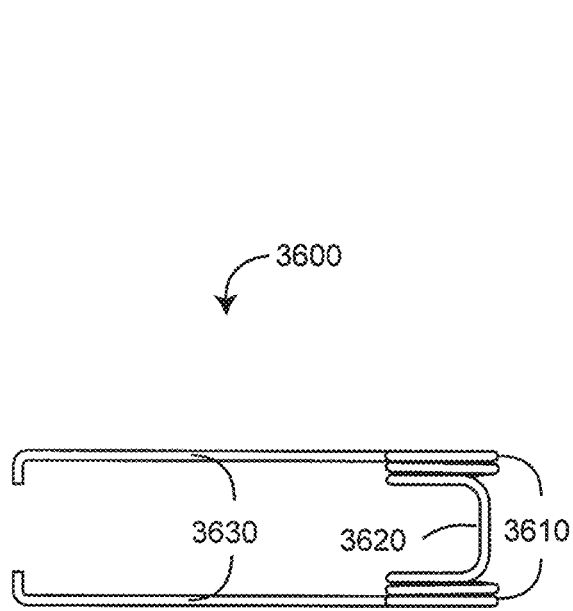
FIGS. 36A-C are top, perspective and side views of a finger clip spring.
Figure 36B:
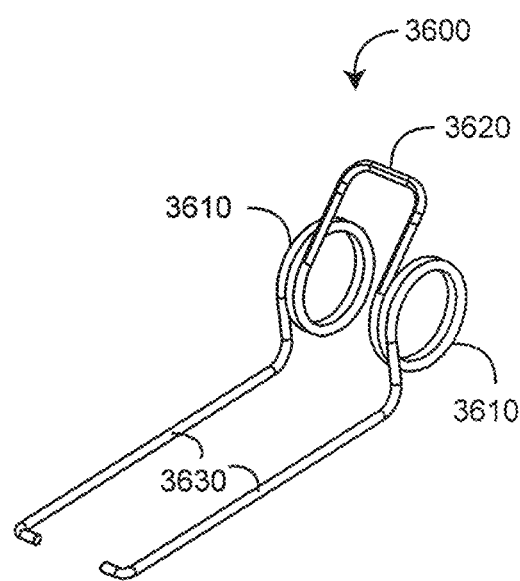
Figure 36C:
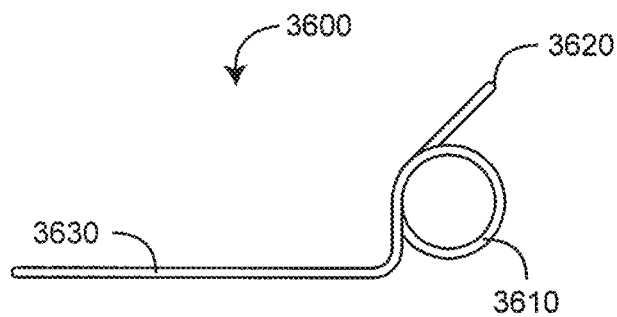
Figure 37A:
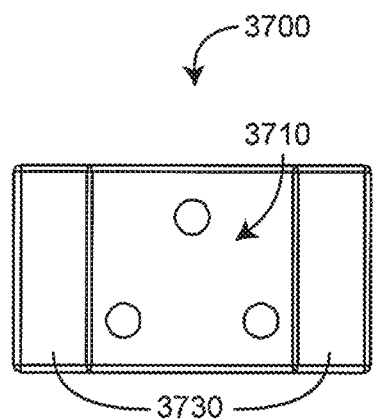
FIGS. 37A-D are top, back, bottom, and side views of a spring plate.
Figure 37B:
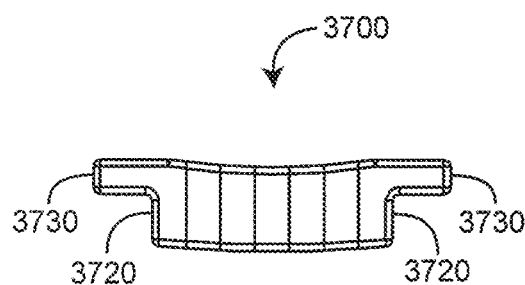
Figure 37D:
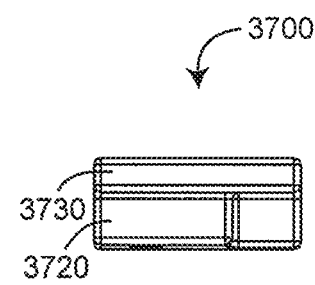
Figure 37C:
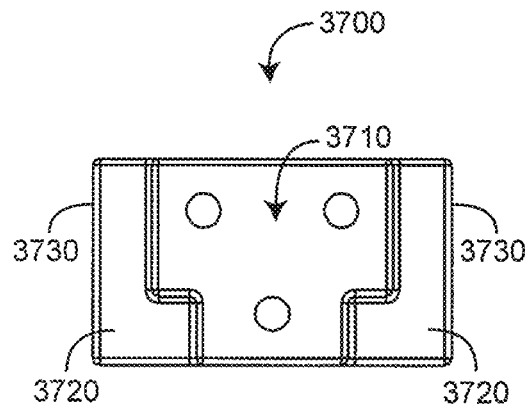
Figure 38A:
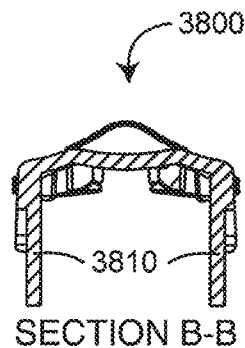
FIGS. 38A-D are front cross sectional, bottom, front and side cross sectional views of an emitter-pad shell.
Figure 38B:
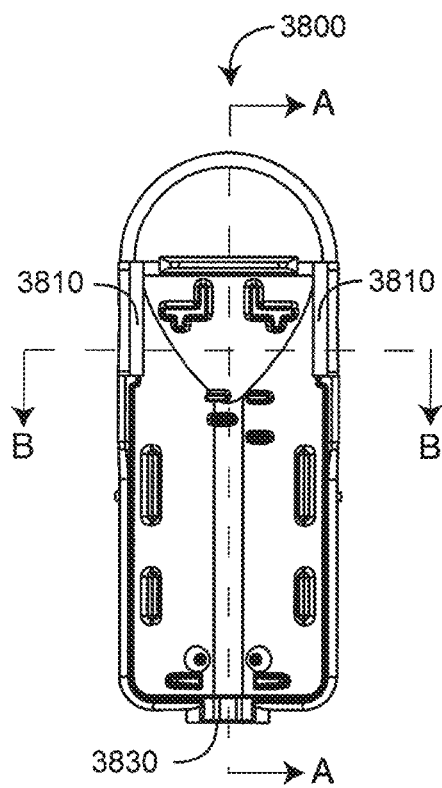
Figure 38D:
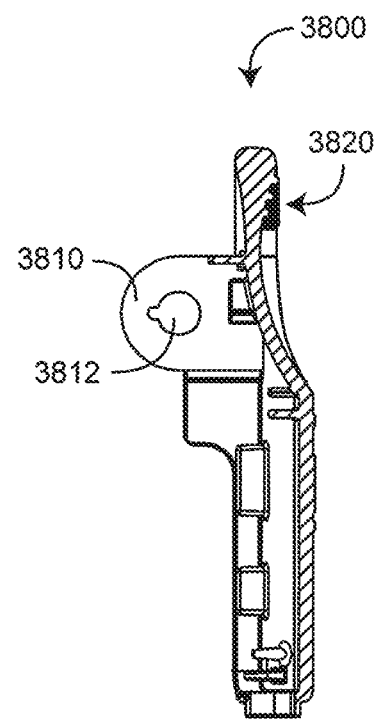
Figure 38C:
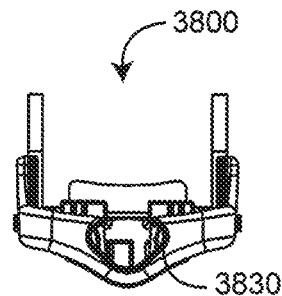
Figure 39A:
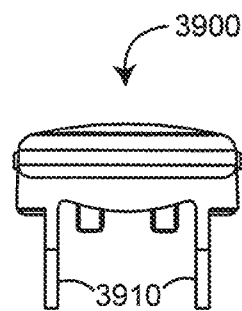
FIGS. 39A-D are back, top, front and side cross sectional views of a detector-pad shell.
Figure 39B:
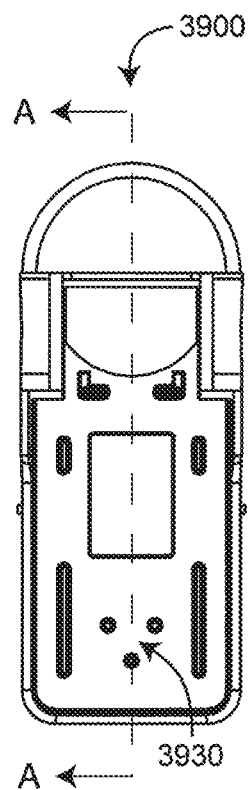
Figure 39D:
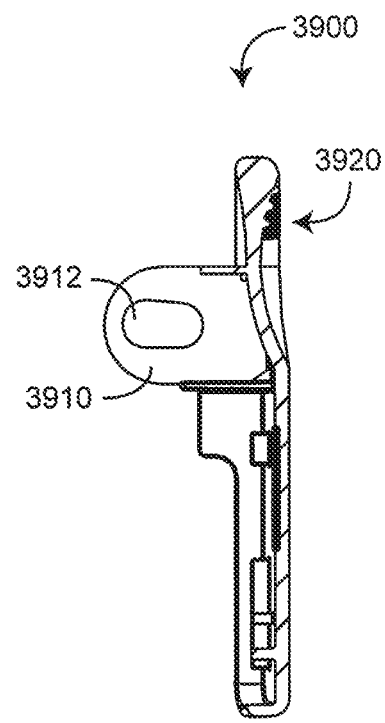
Figure 39C:
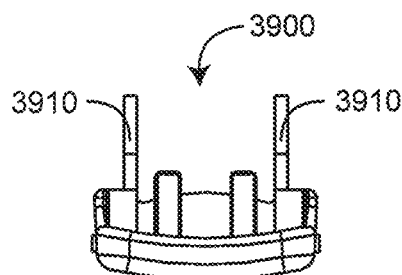

As shown in FIGS. 36A-C, the spring 3600 has coils 3610, an emitter shell leg 3620 and a detector shell leg 3630. The emitter shell leg 3620 presses against the emitter shell 3800 (FIGS. 38A-D) proximate a grip 3820 (FIGS. 38A-D). The detector shell legs 3630 extend along the detector shell 3900 (FIGS. 39A-D) to a spring plate 3700 (FIGS. 37A-D) attachment point. The coil 3610 is secured by hinge pins 410 (FIG. 46) and is configured to wind as the finger clip is opened, reducing its diameter and stress accordingly.

As shown in FIGS. 37A-D the spring plate 3700 has attachment apertures 3710, spring leg slots 3720, and a shelf 3730. The attachment apertures 3710 accept corresponding shell posts 3930 (FIGS. 39A-D) so as to secure the spring plate 3700 to the detector shell 3900 (FIG. 39A-D). Spring legs 3630 (FIG. 36A-C) are slidably anchored to the detector shell 3900 (FIG. 39A-D) by the shelf 3730, advantageously allowing the combination of spring 3600, shells 3800, 3900 and hinges 3810, 3910 to adjust to various finger sizes and shapes.

FIGS. 38-39 illustrate the emitter and detector shells 3800, 3900, respectively, having hinges 3810, 3910 and grips 3820, 3920. Hinge apertures 3812, 3912 accept hinge pins 410 (FIG. 46) so as to create a finger clip. The detector shell hinge aperture 3912 is elongated, allowing the hinge to expand to accommodate a finger.

Monitor And Sensor

Figure 40:
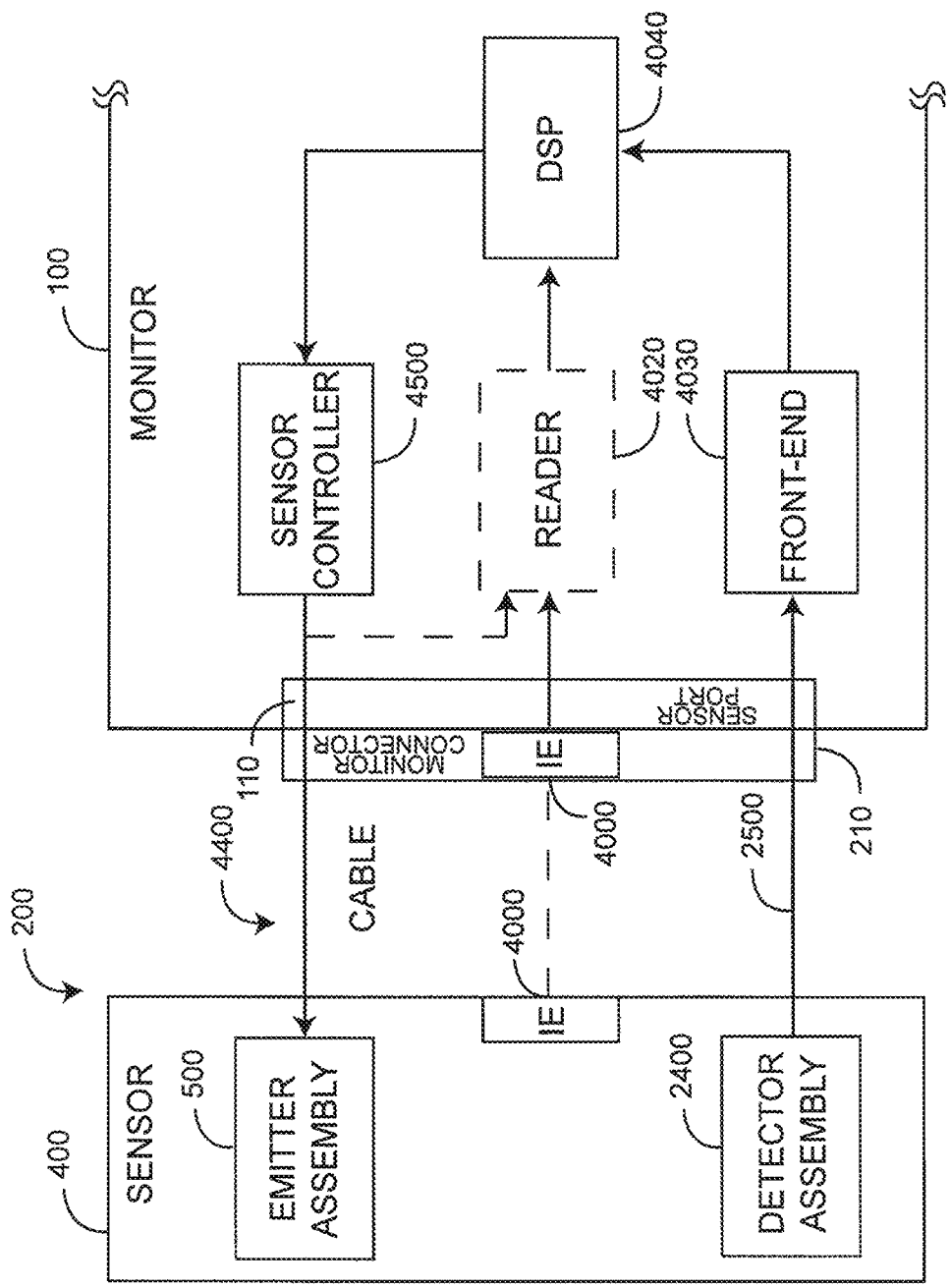
FIG. 40 is a general block diagram of a monitor and a sensor.

FIG. 40 illustrates a monitor 100 and a corresponding sensor assembly 200, as described generally with respect to FIGS. 1-3, above. The sensor assembly 200 has a sensor 400 and a sensor cable 4400. The sensor 400 houses an emitter assembly 500 having emitters responsive to drivers within a sensor controller 4500 so as to transmit optical radiation into a tissue site. The sensor 400 also houses a detector assembly 2400 that provides a sensor signal 2500 responsive to the optical radiation after tissue attenuation. The sensor signal 2500 is filtered, amplified, sampled and digitized by the front-end 4030 and input to a DSP (digital signal processor) 4040, which also commands the sensor controller 4500. The sensor cable 4400 electrically communicates drive signals from the sensor controller 4500 to the emitter assembly 500 and a sensor signal 2500 from the detector assembly 2400 to the front-end 4030. The sensor cable 4400 has a monitor connector 210 that plugs into a monitor sensor port 110.

In one embodiment, the monitor 100 also has a reader 4020 capable of obtaining information from an information element (IE) in the sensor assembly 200 and transferring that information to the DSP 4040, to another processor or component within the monitor 100, or to an external component or device that is at least temporarily in communication with the monitor 100. In an alternative embodiment, the reader function is incorporated within the DSP 4040, utilizing one or more of DSP I/O, ADC, DAC features and corresponding processing routines, as examples.

In one embodiment, the monitor connector 210 houses the information element 4000, which may be a memory device or other active or passive electrical component. In a particular embodiment, the information element 4000 is an EPROM, or other programmable memory, or an EEPROM, or other reprogrammable memory, or both. In an alternative embodiment, the information element 4000 is housed within the sensor 400, or an information element 4000 is housed within both the monitor connector 4000 and the sensor 400. In yet another embodiment, the emitter assembly 500 has an information element 4000, which is read in response to one or more drive signals from the sensor controller 4500, as described with respect to FIGS. 41-43, below. In a further embodiment, a memory information element is incorporated into the emitter array 700 (FIG. 8) and has characterization information relating to the LEDs 801 (FIG. 8). In one advantageous embodiment, trend data relating to slowly varying parameters, such as perfusion index, HbCO or METHb, to name a few, are stored in an IE memory device, such as EEPROM.

Back-to-Back LEDs

Figure 41A:
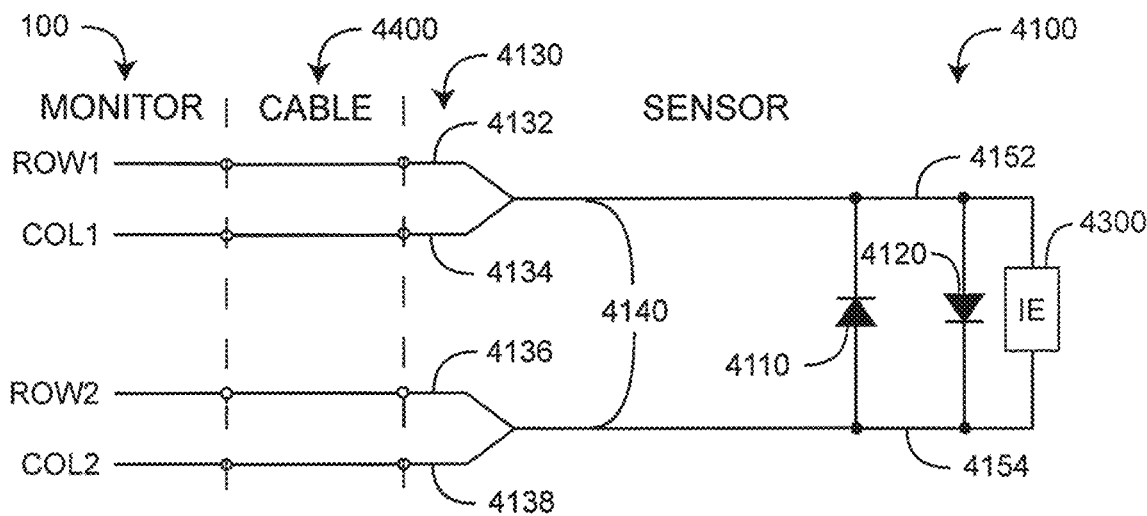
FIGS. 41A-C are schematic diagrams of grid drive embodiments for a sensor having back-to-back diodes and an information element.
Figure 41B:
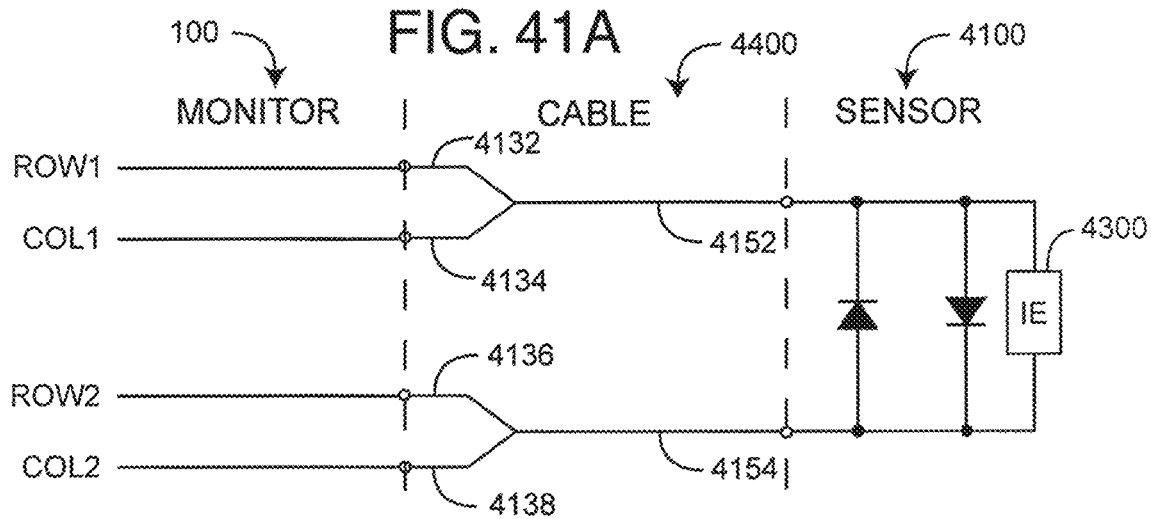
Figure 41C:
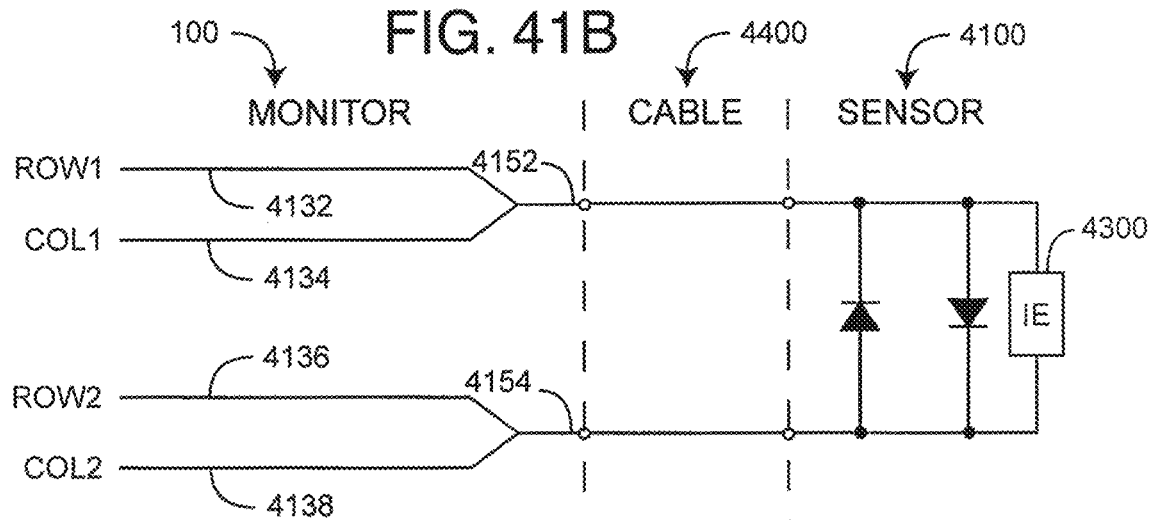
Figure 42:
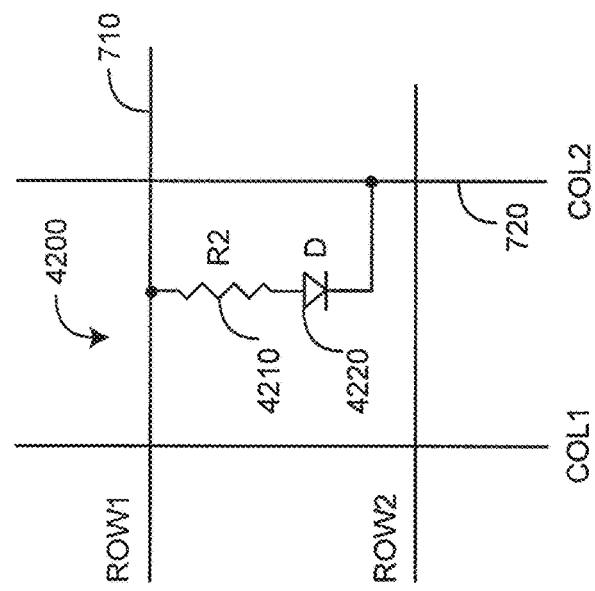
FIG. 42 is a schematic diagrams of a grid drive embodiment for an information element.

FIGS. 41-43 illustrate alternative sensor embodiments. A sensor controller 4500 configured to activate an emitter array 700 (FIG. 7) arranged in an electrical grid, is described with respect to FIG. 7, above. Advantageously, a sensor controller 4500 so configured is also capable of driving a conventional two-wavelength (red and IR) sensor 4100 having back-to-back LEDs 4110, 4120 or an information element 4300 or both.

FIG. 41A illustrates a sensor 4100 having an electrical grid 4130 configured to activate light emitting sources by addressing at least one row conductor and at least one column conductor. A first LED 4110 and a second LED 4120 are configured in a back-to-back arrangement so that a first contact 4152 is connected to a first LED 4110 cathode and a second LED 4120 anode and a second contact 4154 is connected to a first LED 4110 anode and a second LED 4120 cathode. The first contact 4152 is in communications with a first row conductor 4132 and a first column conductor 4134. The second contact is in communications with a second row conductor 4136 and a second column conductor 4138. The first LED 4110 is activated by addressing the first row conductor 4132 and the second column conductor 4138. The second LED 4120 is activated by addressing the second row conductor 4136 and the first column conductor 4134.

FIG. 41B illustrates a sensor cable 4400 embodiment capable of communicating signals between a monitor 100 and a sensor 4100. The cable 4400 has a first row input 4132, a first column input 4134, a second row input 4136 and a second column input 4138. A first output 4152 combines the first row input 4132 and the first column input 4134. A second output 4154 combines a second row input 4136 and second column input 4138.

FIG. 41C illustrates a monitor 100 capable of communicating drive signals to a sensor 4100. The monitor 4400 has a first row signal 4132, a first column signal 4134, a second row signal 4136 and a second column signal 4138. A first output signal 4152 combines the first row signal 4132 and the first column signal 4134. A second output signal 4154 combines a second row signal 4136 and second column signal 4138.

Information Elements

FIGS. 42-43 illustrate information element 4200-4300 embodiments in communications with emitter array drivers configured to activate light emitters connected in an electrical grid. The information elements are configured to provide information as DC values, AC values or a combination of DC and AC values in response corresponding DC, AC or combination DC and AC electrical grid drive signals. FIG. 42 illustrates information element embodiment 4200 advantageously driven directly by an electrical grid having rows 710 and columns 720. In particular, the information element 4200 has a series connected resistor $R_2$ 4210 and diode 4220 connected between a row line 710 and a column line 720 of an electrical grid. In this manner, the resistor $R_2$ value can be read in a similar manner that LEDs 810 (FIG. 8) are activated. The diode 4220 is oriented, e.g. anode to row and cathode to column as the LEDs so as to prevent parasitic currents from unwanted activation of LEDs 810 (FIG. 8).

Figure 43C:
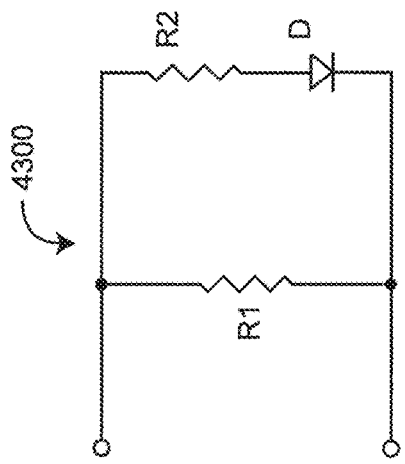
FIGS. 43A-C are schematic diagrams for grid drive readable information elements.
Figure 43B:
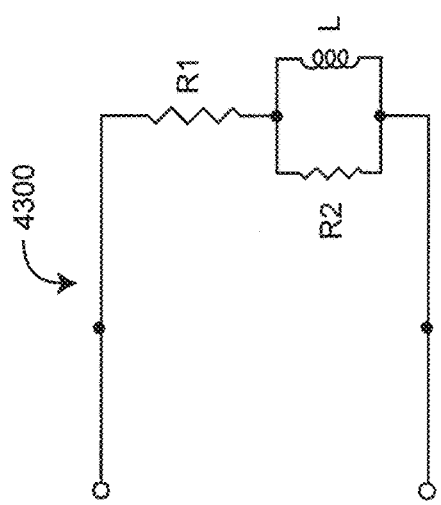
Figure 43A:
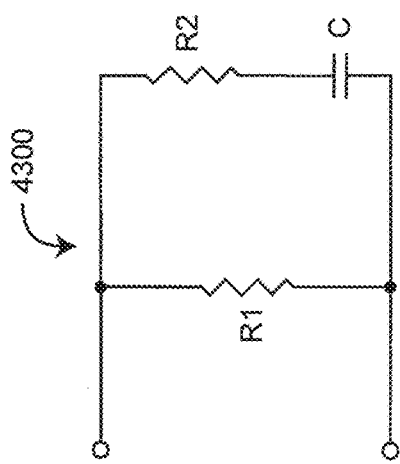

FIGS. 43A-C illustrate other embodiments where the value of $R_1$ is read with a DC grid drive current and a corresponding grid output voltage level. In other particular embodiments, the combined values of $R_1$, $R_2$ and C or, alternatively, $R_1$, $R_2$ and L are read with a varying (AC) grid drive currents and a corresponding grid output voltage waveform. As one example, a step in grid drive current is used to determine component values from the time constant of a corresponding rise in grid voltage. As another example, a sinusoidal grid drive current is used to determine component values from the magnitude or phase or both of a corresponding sinusoidal grid voltage. The component values determined by DC or AC electrical grid drive currents can represent sensor types, authorized suppliers or manufacturers, emitter wavelengths among others. Further, a diode D (FIG. 43C) can be used to provide one information element reading $R_1$ at one drive level or polarity and another information element reading, combining $R_1$ and $R_2$, at a second drive level or polarity, i.e. when the diode is forward biased.

Passive information element 4300 embodiments may include any of various combinations of resistors, capacitors or inductors connected in series and parallel, for example. Other information element 4300 embodiments connected to an electrical grid and read utilizing emitter array drivers incorporate other passive components, active components or memory components, alone or in combination, including transistor networks, PROMs, ROMs, EPROMs, EEPROMs, gate arrays and PLAs to name a few.

Sensor Cable

FIGS. 44A-B illustrate a sensor cable 4400 having an outer jacket 4410, an outer shield 4420, multiple outer wires 4430, an inner jacket 4440, an inner shield 4450, a conductive polymer 4460 and an inner twisted wire pair 4470. The outer wires 4430 are advantageously configured to compactly carry multiple drive signals to the emitter array 700 (FIG. 7). In one embodiment, there are twelve outer wires 4430 corresponding to four anode drive signals 4501 (FIG. 45), four cathode drive signals 4502 (FIG. 45), two thermistor pinouts 1450 (FIG. 15) and two spares. The inner twisted wire pair 4470 corresponds to the sensor signal 2500 (FIG. 25) and is extruded within the conductive polymer 4460 so as to reduce triboelectric noise. The shields 4420, 4450 and the twisted pair 4470 boost EMI and crosstalk immunity for the sensor signal 2500 (FIG. 25).

Controller

Figure 45:
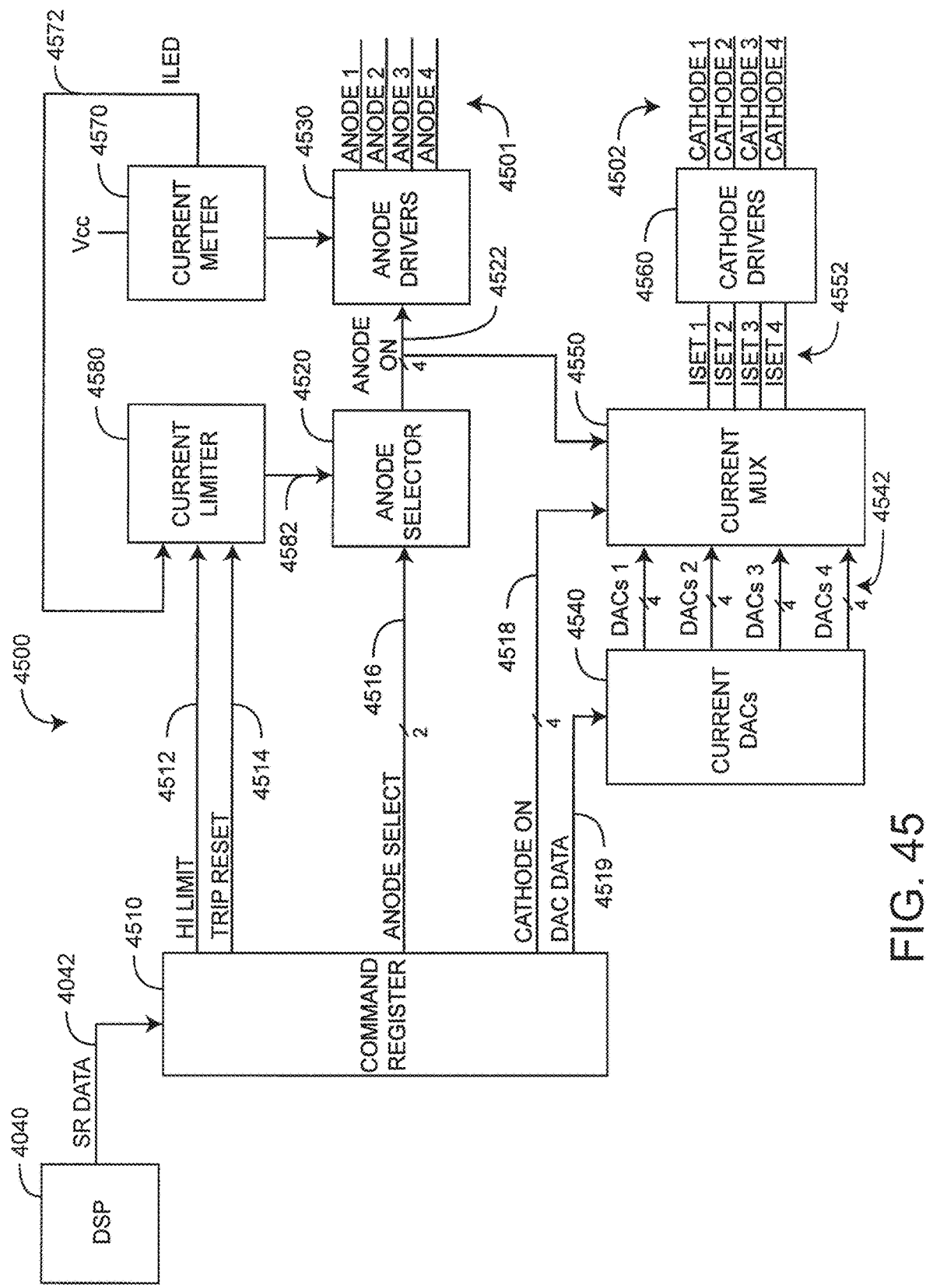
FIG. 45 is a block diagram of a sensor controller embodiment.

FIG. 45 illustrates a sensor controller 4500 located in the monitor 100 (FIG. 1) and configured to provide anode drive signals 4501 and cathode drive signals 4502 to the emitter array 700 (FIG. 7). The DSP (digital signal processor) 4040, which performs signal processing functions for the monitor, also provides commands 4042 to the sensor controller 4500. These commands determine drive signal 4501, 4502 levels and timing. The sensor controller 4500 has a command register 4510, an anode selector 4520, anode drivers 4530, current DACs (digital-to-analog converters) 4540, a current multiplexer 4550, cathode drivers 4560, a current meter 4570 and a current limiter 4580. The command register 4510 provides control signals responsive to the DSP commands 4042. In one embodiment, the command register 4510 is a shift register that loads serial command data 4042 from the DSP 4040 and synchronously sets output bits that select or enable various functions within the sensor controller 4500, as described below.

As shown in FIG. 45, the anode selector 4520 is responsive to anode select 4516 inputs from the command register 4510 that determine which emitter array row 810 (FIG. 8) is active. Accordingly, the anode selector 4520 sets one of the anode on 4522 outputs to the anode drivers 4530, which pulls up to Vcc one of the anode outputs 4501 to the emitter array 700 (FIG. 8).

Also shown in FIG. 45, the current DACs 4540 are responsive to command register data 4519 that determines the currents through each emitter array column 820 (FIG. 8). In one embodiment, there are four, 12-bit DACs associated with each emitter array column 820 (FIG. 8), sixteen DACs in total. That is, there are four DAC outputs 4542 associated with each emitter array column 820 (FIG. 8) corresponding to the currents associated with each row 810 (FIG. 8) along that column 820 (FIG. 8). In a particular embodiment, all sixteen DACs 4540 are organized as a single shift register, and the command register 4510 serially clocks DAC data 4519 into the DACs 4540. A current multiplexer 4550 is responsive to cathode on 4518 inputs from the command register 4510 and anode on 4522 inputs from the anode selector 4520 so as to convert the appropriate DAC outputs 4542 to current set 4552 inputs to the cathode drivers 4560. The cathode drivers 4560 are responsive to the current set 4552 inputs to pull down to ground one to four of the cathode outputs 4502 to the emitter array 700 (FIG. 8).

The current meter 4570 outputs a current measure 4572 that indicates the total LED current driving the emitter array 700 (FIG. 8). The current limiter 4580 is responsive to the current measure 4572 and limits specified by the command register 4510 so as to prevent excessive power dissipation by the emitter array 700 (FIG. 8). The current limiter 4580 provides an enable 4582 output to the anode selector 4520. A Hi Limit 4512 input specifies the higher of two preset current limits. The current limiter 4580 latches the enable 4582 output in an off condition when the current limit is exceeded, disabling the anode selector 4520. A trip reset 4514 input resets the enable 4582 output to re-enable the anode selector 4520.

Sensor Assembly

Figure 46:
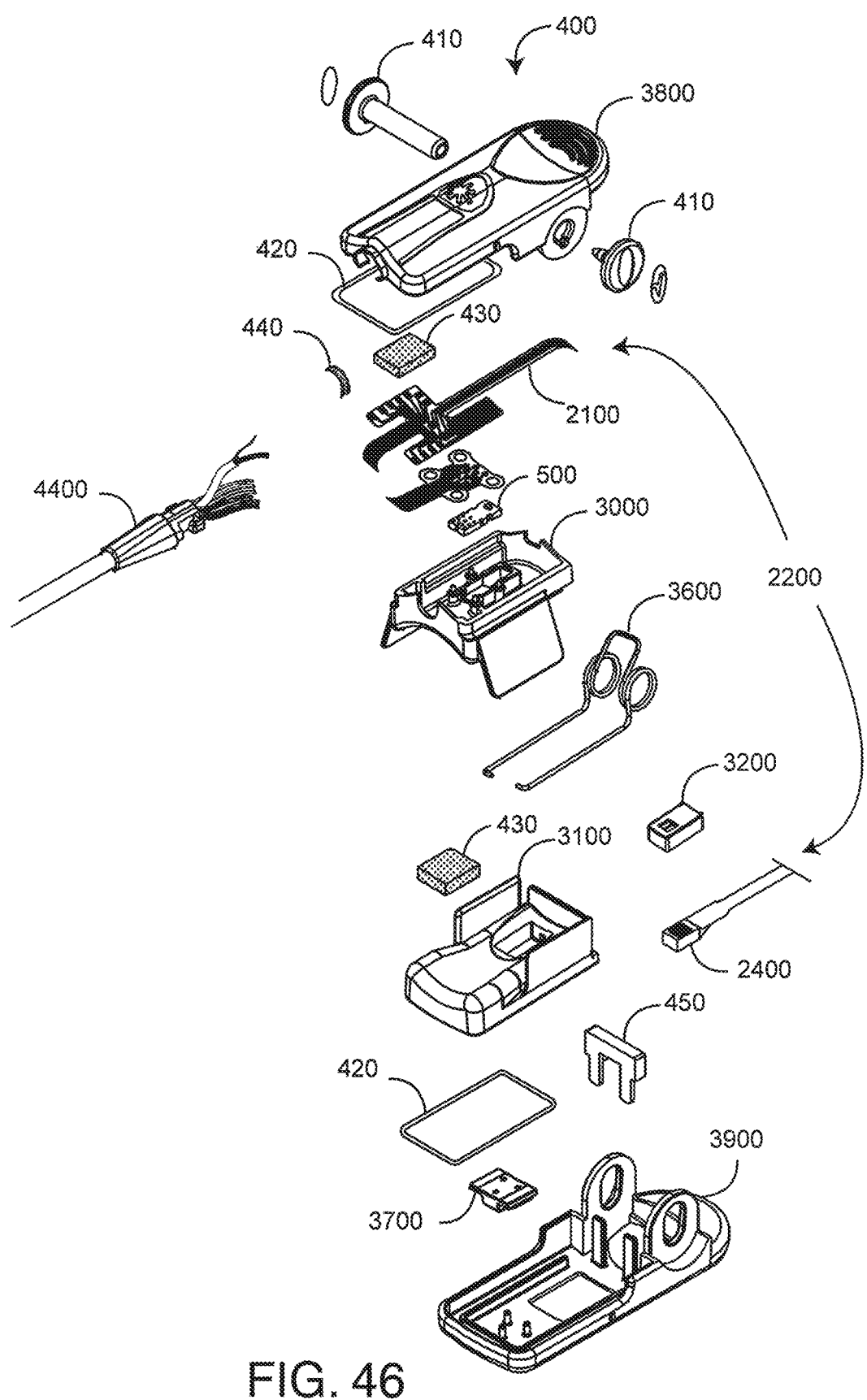
FIG. 46 is a detailed exploded perspective view of a multiple wavelength sensor embodiment.

As shown in FIG. 46, the sensor 400 has an emitter shell 3800, an emitter pad 3000, a flex circuit assembly 2200, a detector pad 3100 and a detector shell 3900. A sensor cable 4400 attaches to the flex circuit assembly 2200, which includes a flex circuit 2100, an emitter assembly 500 and a detector assembly 2400. The portion of the flex circuit assembly 2200 having the sensor cable 4400 attachment and emitter assembly 500 is housed by the emitter shell 3800 and emitter pad 3000. The portion of the flex circuit assembly 2200 having the detector assembly 2400 is housed by the detector shell 3900 and detector pad 3100. In particular, the detector assembly 2400 inserts into a shoe 3200, and the shoe 3200 inserts into the detector pad 3100. The emitter shell 3800 and detector shell 3900 are fastened by and rotate about hinge pins 410, which insert through coils of a spring 3600. The spring 3600 is held to the detector shell 3900 with a spring plate 3700. A finger stop 450 attaches to the detector shell. In one embodiment, a silicon adhesive 420 is used to attach the pads 3000, 3100 to the shells 3800, 3900, a silicon potting compound 430 is used to secure the emitter and detector assemblies 500, 2400 within the pads 3000, 3100, and a cyanoacrylic adhesive 440 secures the sensor cable 4400 to the emitter shell 3800.

A multiple wavelength sensor has been disclosed in detail in connection with various embodiments. These embodiments are disclosed by way of examples only and are not to limit the scope of the claims that follow. One of ordinary skill in art will appreciate many variations and modifications.

What is claimed is:

1. A physiological monitoring device comprising:
    at least two LEDs, the at least two LEDs configured to emit light of at least two different wavelengths;
    at least one detector configured to detect at least a portion of the light emitted from the at least two LEDs after at least a portion of the light has been attenuated by tissue, the at least one detector configured to output at least one signal responsive to the detected light;
    a light block surrounding the at least one detector and configured to be disposed within a housing of the physiological monitoring device, the light block forming a cavity, the light block comprising a light-absorbing material, the light block including only one opening through which light is configured to pass, an area of the opening being smaller than a surface area of a facing surface of the at least one detector, the light absorbing material forming at least an edge of the only one opening; and a processor configured to receive and process one or more signals responsive to the outputted at least one signal and determine a physiological parameter of a user responsive to the one or more signals.

2. The physiological monitoring device of claim 1, wherein the at least two LEDs comprises at least eight LEDs.

3. The physiological monitoring device of claim 2, wherein the at least eight LEDs comprises at least two LEDs of the same wavelength.

4. The device of claim 2, wherein the at least eight LEDs comprises at least two LEDs of the same wavelength.

5. The physiological monitoring device of claim 1, wherein the at least two LEDs comprises at least twelve LEDs.

6. The physiological monitoring device of claim 1, wherein multiple LEDs of the at least two LEDs are configured for concurrent activation.

7. The physiological monitoring device of claim 1, wherein the at least one detector comprises at least two detectors.

8. The physiological monitoring device of claim 1, further comprising an electromagnetic interference shield positioned between the at least two LEDs and the at least one detector.

9. The physiological monitoring device of claim 1, wherein the light block is a substantially rectangular enclosure.

10. The physiological monitoring device of claim 1, wherein the light block comprises a base, a plurality of side walls, and a top.

11. The physiological monitoring device of claim 1, wherein the area of the opening is less than half a surface area of a top of the light block.

12. The physiological monitoring device of claim 1, wherein the opening is screen-less.

13. The physiological monitoring device of claim 1, wherein the light block comprises an aperture sized to accept the at least one detector, wherein the aperture is different from the opening.

14. A method for determining a physiological parameter of a living patient, the method comprising:

positioning a sensor with respect to body tissue of a living patient, the sensor comprising at least two LEDs, at least one detector, a light block surrounding the at least one detector, the at least two LEDs configured to emit light of at least two different wavelengths, the light block forming a cavity, the light block comprising a light-absorbing material, the light block including only one opening through which light is configured to pass, an area of the opening being smaller than a surface area of a facing surface of the at least one detector, the light absorbing material forming at least an edge of the only one opening;

activating the at least two LEDs;

detecting, at the at least one detector, at least a portion of the light emitted from the at least two LEDs after at least a portion of the light has been attenuated by the body tissue, passed through a transparent medium, and passed through the opening of the light block, wherein the at least one detector outputs at least one signal responsive to the detected light, wherein the transparent medium is positioned in an optical path between the at least two LEDs and the at least one detector; and determining a physiological parameter of the living patient responsive to the outputted at least one signal.

15. The method of claim 14, wherein the at least two LEDs comprises at least eight LEDs.

16. The method of claim 15, wherein the at least eight LEDs comprises at least two LEDs of the same wavelength.

17. The method of claim 14, wherein the at least two LEDs comprises at least twelve LEDs.

18. The method of claim 14, wherein said activating the at least two LEDs comprises concurrently activating multiple LEDs of the at least two LEDs.

19. The method of claim 14, wherein the at least one detector comprises at least two detectors.

20. The method of claim 14, wherein the sensor further comprises an electromagnetic interference shield positioned between the at least two LEDs and the at least one detector.

21. The method of claim 14, wherein the light block is a substantially rectangular enclosure.

22. The method of claim 14, wherein the light block comprises a shoebox structure.

23. The method of claim 14, wherein the opening is screen-less.

24. The method of claim 14, wherein the light block comprises an aperture sized to accept the at least one detector, wherein the aperture is different from the opening.

25. The method of claim 14, wherein the at least a portion of the light passes through the transparent medium after the at least a portion of the light has been attenuated by the body tissue.

26. The method of claim 14, wherein the light block is configured to be disposed within a housing of the physiological monitoring device.

27. A physiological sensor comprising:

a housing;

at least two LEDs, the at least two LEDs configured to emit light of at least two different wavelengths;

at least one detector configured to detect at least a portion of the light emitted from the at least two LEDs after at least a portion of the light has been attenuated by tissue, the at least one detector configured to output at least one signal responsive to the detected light; and a light block that is at least partially enclosed, the light block surrounding the at least one detector, the light block forming a cavity, the light block comprising a light-absorbing material, the light block including only one opening through which light is configured to pass, an area of the opening being smaller than a surface area of a facing surface of the at least one detector, the light absorbing material forming at least an edge of the only one opening, and_the light block configured to be disposed within the housing.

28. The sensor of claim 27, wherein the at least two LEDs comprises at least eight LEDs.

29. The sensor of claim 27, further comprising an electromagnetic interference shield positioned between the at least two LEDs and the at least one detector.

30. The sensor of claim 27, wherein the light block comprises a shoebox structure.

* * * * *